United States Patent [19]

Ok et al.

[11] Patent Number: 5,208,241
[45] Date of Patent: May 4, 1993

[54] N-HETEROARYL, N-ALKYLHETEROARYL, N-ALKENYLHETEROARYL AND N-ALKYNYLHETEROARYLMACROLIDES HAVING IMMUNOSUPPRESSIVE ACTIVITY

[75] Inventors: Hyun O. Ok, Edison; Joung Goulet, Westfield; Peter J. Sinclair, Highland Park, all of N.J.

[73] Assignee: Merck & Co., Inc., Rahway, N.J.

[21] Appl. No.: 756,660

[22] Filed: Sep. 9, 1991

[51] Int. Cl.$^5$ ................. C07D 521/00; A61K 31/395
[52] U.S. Cl. .................... 514/291; 514/183; 514/411; 540/456
[58] Field of Search ............... 540/456; 514/183, 291, 514/411

[56] References Cited

U.S. PATENT DOCUMENTS

| | | | |
|---|---|---|---|
| 4,650,803 | 3/1987 | Stella et al. | 514/291 |
| 4,894,366 | 1/1990 | Okuhara et al. | 514/63 |
| 4,916,138 | 4/1990 | Ueda et al. | 514/294 |

(List continued on next page.)

FOREIGN PATENT DOCUMENTS

| | | | |
|---|---|---|---|
| 0315978 | 5/1989 | European Pat. Off. | 514/291 |
| 0323042 | 7/1989 | European Pat. Off. | 514/291 |
| 0349061 | 1/1990 | European Pat. Off. | 514/291 |
| 0353678 | 2/1990 | European Pat. Off. | 514/291 |
| 0356399 | 2/1990 | European Pat. Off. | 514/291 |
| 0369344 | 5/1990 | European Pat. Off. | 514/291 |

(List continued on next page.)

OTHER PUBLICATIONS

Tanaka, et al., J. Am. Chem. Soc., 1987, 109 5031–5033.
Bierer, et al., Science, 1990, 250, 556–559.
Donald, et al., Tetrahedron Lett., 1991, 32, 1375–1378.

(List continued on next page.)

*Primary Examiner*—Robert T. Bond
*Attorney, Agent, or Firm*—Charles M. Caruso; J. Eric Thies

[57] ABSTRACT

N-Heteroaryl, N-alkylheteroaryl, N-alkenylheteroaryl and N-alkynylheteroaryl macrolides of the general structural Formula I:

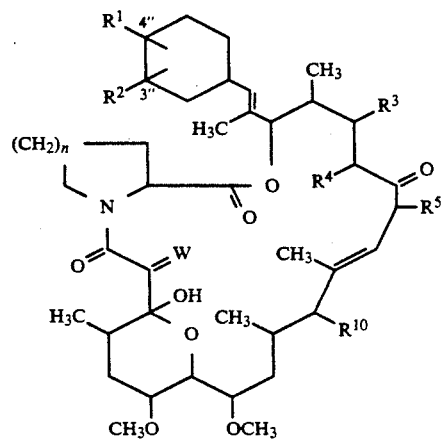

have been prepared from suitable precursors by amination, alkylation and/or arylation at C-3" and/or C-4" of the cyclohexyl ring. These macrolide immunosuppressants are useful in a mammalian host for the treatment of autoimmune diseases, infectious diseases and/or the prevention of rejection of foreign organ transplants. In addition, these macrolide immunosuppressants are useful in the topical treatment of inflammatory and hyperproliferative skin diseases and cutaneous manifestations of immunologically-mediated illnesses. Also, these macrolides are useful in the treatment of reversible obstructive airways disease, particularly asthma. Furthermore, these macrolides are useful as hair revitalizing agents, especially in the treatment of male pattern alopecia or alopecia senilis.

32 Claims, No Drawings

U.S. PATENT DOCUMENTS

| | | | |
|---|---|---|---|
| 4,929,611 | 5/1990 | Okuhara et al. | 514/183 |
| 4,956,352 | 9/1990 | Okuhara et al. | 514/63 |
| 4,981,792 | 1/1991 | Inamine et al. | 435/119 |
| 4,987,139 | 1/1991 | Chen et al. | 514/321 |
| 5,011,844 | 4/1991 | Fehr | 514/291 |

FOREIGN PATENT DOCUMENTS

| | | | |
|---|---|---|---|
| 0388152 | 9/1990 | European Pat. Off. | 514/291 |
| 0388153 | 9/1990 | European Pat. Off. | 514/291 |
| 0402931 | 12/1990 | European Pat. Off. | 514/291 |
| 0413532 | 2/1991 | European Pat. Off. | 514/291 |
| 0423714 | 4/1991 | European Pat. Off. | 514/291 |
| 0427680 | 5/1991 | European Pat. Off. | 514/291 |
| 0428169 | 5/1991 | European Pat. Off. | 514/291 |
| 0428365 | 5/1991 | European Pat. Off. | 514/291 |
| 0444659 | 9/1991 | European Pat. Off. | 514/291 |
| 0444829 | 9/1991 | European Pat. Off. | 514/291 |
| 0445975 | 9/1991 | European Pat. Off. | 514/2911 |
| WO89/05304 | 6/1989 | World Int. Prop. O. | 514/291 |
| WO90/14826 | 12/1990 | World Int. Prop. O. | 514/291 |
| WO91/02736 | 3/1991 | World Int. Prop. O. | 514/291 |
| WO91/04025 | 4/1991 | World Int. Prop. O. | 514/291 |
| WO91/13889 | 9/1991 | World Int. Prop. O. | 514/291 |
| WO91/13899 | 9/1991 | World Int. Prop. O. | 514/291 |

OTHER PUBLICATIONS

C. Arita, et al., Clin. exp Immunol, 1990, 82, 456–461.

N. Murase, et al., Diabetes, 1990, 39, 1584–86.

J. McCauley, et al., Lancet, 1990, 335, 674.

K. Takabayashi, et al., Clin. Immunol. Immunopathol., 1989, 51, 110–117.

M. Sakr, et al. Life Sciences, 1990, 47, 687–691.

N-HETEROARYL, N-ALKYLHETEROARYL, N-ALKENYLHETEROARYL AND N-ALKYNYLHETEROARYLMACROLIDES HAVING IMMUNOSUPPRESSIVE ACTIVITY

SUMMARY OF THE INVENTION

The present invention is related to N-heteroaryl, N-alkylheteroaryl, N-alkenylheteroaryl and N-alkynylheteroarylmacrolides which are useful in a mammalian host for the treatment of autoimmune diseases (such as juvenile-onset or recent-onset diabetes mellitus, multiple sclerosis, rheumatoid arthritis, liver disease, posterior uveitis, allergic encephalomyelitis, and glomerulonephritis), immunodepression, infectious diseases, the prevention of rejection of foreign organ transplants, e.g. bone marrow, kidney, liver, heart, skin, small-bowel, and pancreatic-islet-cell transplants, the topical treatment of inflammatory and hyperproliferative skin diseases, cutaneous manifestations of immunologically-mediated illnesses (such as psoriasis, atopical dermatitiis, contact dermatitis and further eczematous dermatitises, seborrhoeic dermatitis, Lichen planus, Pemphigus, bullous Pemphigoid, Epidermolysis bullosa, urticaria, angioedemas, vasculitides, erythemas, cutaneous eosinophilias, Lupus erythematosus or Alopecia areata), male pattern alopecia, alopecia senilis, reversible obstructive airways disease, particularly asthma, and/or hepatic injury associated with ischemia. In addition, some of the compounds of this invention may have antagonistic properties and so have utility in the reversal of immunosuppressive activity and/or diminishing the toxicity of other immunosuppressive agents.

More particularly, this invention relates to compounds of the general structural Formula I:

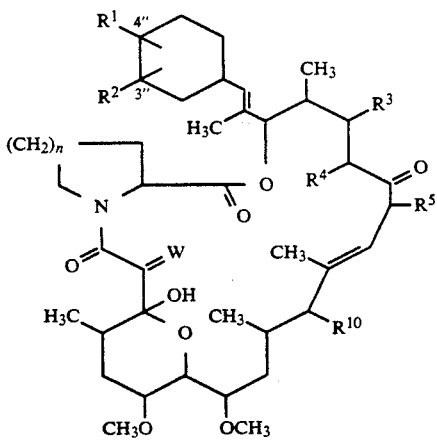

wherein R, $R^1$, $R^2$, $R^3$, $R^4$, $R^5$, $R^{10}$, W, and n are hereinafter defined.

This invention also relates to pharmaceutical compositions containing the compounds and to a method of use of the present compounds and other agents for the treatment of autoimmune diseases, immunodepression, infectious diseases, the rejection of foreign organ transplants, inflammatory and hyperproliferative skin diseases, cutaneous manifestations of immunologically-mediated illnesses, male pattern alopecia, alopecia senilis, reversible obstructive airways disease, and further for modifying the activity and/or toxicity of other immunosuppressive agents.

BRIEF DESCRIPTION OF DISCLOSURES IN THE ART

Fujisawa United States, European and Japanese patents and applications (U.S. Pat. No. 4,894,366, issued Jan. 16, 1990, EPO Publication No. 0,184,162 and PBJ Disclosure 63-17884) and publications (J. Am. Chem. Soc., 1987, 109, 5031 and J. Antibiotics 1987, 40, 1249) disclose 17-allyl-1,14-dihydroxy-12-[2'-(4"-hydroxy-3"-methoxycyclohexyl)-1'-methylvinyl]-23,25-dimethoxy-13,19,21,27-tetramethyl-11,28-dioxa-4-azatricyclo-[22.3.1.0$^{4,9}$]octacos-18-ene-2,3,10,16-tetraone (FR-900506), (FK-506), (L-679,934), 17-ethyl-1,14-dihydroxy-12-[2'-(4"-hydroxy-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone (FR-900520) and related compounds which are the starting materials for the preparation of the compounds described. The synthetic preparation of the aforementioned starting material (FR-900506) has recently been reported (J. Am. Chem. Soc., 1989, 111, 1157). A Sandoz European patent application (EPO Publication No. 0,356,399) discloses stereoisomers of FR-900506 and derivatives at the 17-position. Fisons European and WIPO patent applications (EPO Publication No. 0,323,042 and PCT Publication No. WO 89/05304) discloses various derivatives of FR-900506, FR-900520 and related compounds. A Sandoz European Patent application (EPO Publication No. 0,437,680) discloses chloro, bromo, iodo and azido derivatives of FR-900506, FR-900520 and related compounds. A Merck European Patent application (EPO Publication No. 0,428,365) discloses various amino derivatives of FR-900506, FR-900520 and related compounds.

Fujisawa United States patents (U.S. Pat. No. 4,929,611, issued May 29, 1990 and U.S. Pat. No. 4,956,352, issued Sept. 11, 1990) discloses the use of FK-506-type compounds in treating resistance to transplantation. A Sandoz European patent application (EPO Publication No. 0,315,978) discloses the use of FR-900506 and related compounds in the topical treatment of inflammatory and hyperproliferative skin diseases and of cutaneous manifestations of immunologically-mediated illness. A Fisons WIPO patent application (PCT Publication No. WO 91/04025) discloses the use of various derivatives of FR-900506 in the treatment of immunodepression. A Fisons WIPO patent application (PCT Publication WO 90/14826) discloses the use of FR-900506 and related compounds in the treatment of reversible obstructive airways disease, particularly asthma. A Fujisawa European patent application (EPO Publication No. 0,423,714) discloses the use of FK-506 and derivatives as hair revitalizing agents. Various studies have suggested the efficacy of FK-506 in the treatment of a number of ailments, including rheumatoid arthritis (C. Arita, et al., Clincial exp. Immunol., 1990, 82, 456-461; N. Inamura, et al., Clin. Immunol. Immunopathol. 1988, 46, 82-90), recent-onset diabetes (N. Murase, et al., Diabetes, 1990, 39, 1584-86; N. Murase, et al., Lancet, 1990, 336, 373-74), posterior uveitis (H. Kawashima, Invest. Ophthalmol. Vis. Sci., 1988, 29, 1265-71), hepatic injury associated with ischemia (M. Sakr, et al., Life Sci., 1990, 47, 687-91) allergic encephalomyelitis (K, Deguchi, et al., Brain Nerve, 1990, 42, 391-97), glomeralonephritis (J. McCauley, et al., Lancet, 1990, 335, 674) and systemic lupus erythematosus (K.

Takabayashi, et al., *Clin. Immunol. Immunopathol.*, 1989, 51, 110-117).

BACKGROUND OF THE INVENTION

Immunoregulatory abnormalities have been shown to exist in a wide variety of "autoimmune" and chronic inflammatory diseases, including systemic lupus erythematosis, chronic rheumatoid arthritis, type 1 diabetes mellitus, inflammatory bowel disease, biliary cirrhosis, uveitis, multiple sclerosis and other disorders such as Chrons disease, ulcerative colitis, bullous pemphigoid, sarcoidosis, psoriasis, ichthyosis, and Graves ophthalmopathy. Although the underlying pathogenesis of each of these conditions may be quite different, they have in common the appearance of a variety of autoantibodies and self-reactive lymphocytes. Such self-reactivity may be due, in part, to a loss of the homeostatic controls under which the normal immune system operates.

Similarly, following a bone-marrow or an organ transplantation, the host lymphocytes recognize the foreign tissue antigens and begin to produce antibodies which lead to graft rejection.

One end result of an autoimmune or a rejection process is tissue destruction caused by inflammatory cells and the mediators they release. Antiinflammatory agents such as NSAIDs and corticosteroids act principally by blocking the effect or secretion of these mediators but do nothing to modify the immunologic basis of the disease. On the other hand, cytotoxic agents such as cyclophosphamide, act in such a nonspecific fashion that both the normal and autoimmune responses are shut off. Indeed, patients treated with such nonspecific immunosuppressive agents are as likely to succumb from infection as they are from their autoimmune disease.

Cyclosporin A which was approved by the U.S. FDA in 1983 is currently the leading drug used to prevent rejection of transplanted organs. The drug acts by inhibiting the body's immune system from mobilizing its vast arsenal of natural protecting agents to reject the transplant's foreign protein. Though cyclosporin A is effective in fighting transplant rejection, it is nephrotoxic and is known to cause several undesirable side effects including kidney failure, abnormal liver function and gastrointestinal discomfort.

Newer, safer drugs exhibiting less side effects are constantly being searched for in the field.

The 23-membered tricyclo-macrolide immunosuppressant, FR-900506, FK-506,

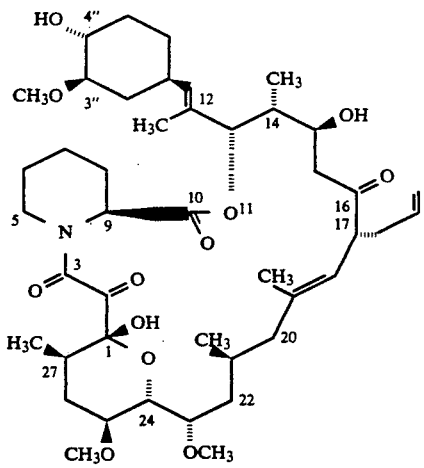

(17-allyl-1,14-dihydroxy-12-[2'-(4"-hydroxy-3"-methoxycyclohexyl)-1'-methylvinyl]-23,25-dimethoxy-13,19,21,27-tetramethyl-11,28-dioxa-4-azatricyclo-[22.3.1.0$^{4,9}$]-octacos-18-ene-2,3,10,16-tetraone) and related compounds which were isolated and characterized by Tanaka, Kuroda, and co-workers at Fujisawa Pharmaceutical Co. in Japan, see *J. Am. Chem. Soc.*, 1987, 109, 5031, and U.S. Pat. No. 4,894,366, issued Jan. 16, 1990) have been shown to possess exceptional immunosuppressive activity. Fujisawa U.S. patents (U.S. Pat. Nos. 4,929,611, issued May 29, 1990 and 4,956,352, issued Sep. 11, 1990) disclose the use of FK-506-type compounds in treating resistance to transplantation. In particular, the compound FR-900506 has been reported to be 100 times more effective than cyclosporin in the supression of in vitro immune systems (*J. Antibiotics* 1987, 40, 1256). In addition, these compounds are reputed to possess topical activity in the treatment of inflammatory and hyperproliferative skin diseases and cutaneous manifestations of immunologically-mediated illnesses (EPO Pub. No. 0,315,978).

The compound FK-506 and related compounds further have been suggested to be useful in the treatment of obstructive airways disease, particularly asthma (PCT Publication WO 90/14826), male pattern alopecia or alopecia senilis (EPO Publication No. 0,423,714), rheumatoid arthitis (C. Arita, et al., *Clinical exp. Immunol.*, 1990, 82, 456-461; N. Inamura, et al., *Clin. Immunol. Immunopathol.* 1988, 46, 82-90), recent-onset diabetes (N. Murase, et al., *Diabetes,* 1990, 39, 1584-86; N. Murase, et al., *Lancet*, 1990, 336, 373-74), posterior uveitis (H. Kawashima, *Invest. Ophthalmol. Vis. Sci.*, 1988, 29, 1265-71), hepatic injury associated with ischemia (M. Sakr, et al., *Life Sci.*, 1990, 47, 687-91) allergic encephalomyelitis (K, Deguchi, et al., *Brain Nerve*, 1990, 42, 391-97), glomerulonephritis (J. McCauley, et al., *Lancet*, 1990, 335, 674) and systemic lupus erythematosus (K. Takabayashi, et al., *Clin. Immunol. Immunopathol.*, 1989, 51, 110-117).

Accordingly, an object of the present invention is to provide new analogs of these tricyclomacrolides which will (1) restore the balance of the help-and-suppression mechanism of the immune system by acting at an earlier point than the antiinflammatory agents and (2) induce specific long-term transplantation tolerance through a suppressor cell circuit without increasing the body's susceptibility to infection.

An additional object of the present invention is to provide new analogs of these tricyclomacrolide immunosuppressants which act as antagonists of macrocyclic immunosuppressive compounds, including derivatives of 12-(2'-cyclohexyl-1'-methylvinyl)-13,19,21,27-tetramethyl-11,28-dioxa-4-azatricyclo-[22.3.1.0$^{4,9}$]octacos-18-ene, and so would be useful in the treatment of immunodepression or in the modification of the immunosuppressive activity or toxicity of such macrocyclic immunosuppressive compounds.

An additional object of the present invention is to provide new analogs of these tricyclomacrolide immunosuppressants which have antagonistic properties. These analogs would find utility in the reversal of the immunosuppressive activity of other immunosuppressive agents and so provide antidotes for overdoses of the immunosuppressants. These analogs would further find utility in diminishing the toxicity of other immunosuppressive agents allowing higher dosages of such agents while minimizing their toxic effects.

Another object of the present invention is to provide analogs of these tricyclo-macrolides which possess topical activity in the treatment of inflammatory and hyperproliferative skin diseases and cutaneous manifestations of immunologically-mediated illnesses.

An additional object of the present invention is to provide pharmaceutical compositions for administering to a patient in need of the treatment one or more of the active immunosuppressive agents of the present invention.

Still a further object of this invention is to provide a method of controlling graft rejection, autoimmune and chronic inflammatory diseases by administering a sufficient amount of one or more of the novel immunosuppressive agents in a mammalian species in need of such treatment.

Finally, it is the object of this invention to provide processes for the preparation of the active compounds of the present invention.

DETAILED DESCRIPTION OF THE INVENTION

A. Scope of the Invention

The novel compound of this invention has structural Formula I:

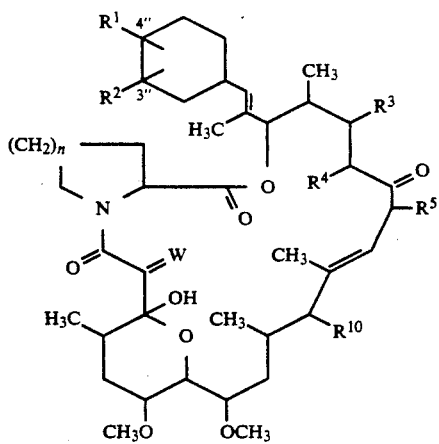

or a pharmaceutically acceptable salt thereof, wherein:

$R^1$ is selected from:

(1) $-NR^6R^7$,
(2) $-NR^6COR^7$,
(3) $-NR^7COR^6$,
(4) $-NR^7CO_2R^6$,
(5) $-NR^6CO_2R^7$, and
(6) $-NR^6CHR^6R^7$;

$R^6$ is selected from
(1) heteroaryl;
(2) substituted heteroaryl in which the substituents are X, Y and Z;
(3) heteroaryl-$C_{1-10}$alkyl;
(4) substituted heteroaryl-$C_{1-10}$alkyl in which the heteroaryl group is substituted by X, Y and Z and the alkyl portion may be substituted with one or more of the substituent(s) selected from:
  (a) hydroxy,
  (b) oxo,
  (c) $C_{1-6}$alkoxy,
  (d) phenyl-$C_{1-3}$alkoxy,
  (e) substituted phenyl-$C_{1-3}$alkoxy, in which the substituents on phenyl are X, Y and Z,
  (f) $-OCO-C_{1-6}$alkyl,
  (g) $-NR^8R^9$, wherein $R^8$ and $R^9$ are independently selected from
    (i) hydrogen,
    (ii) $C_{1-10}$alkyl unsubstituted or substituted with one or more of the substituent(s) selected from:
      (a') phenyl, which is unsubstituted or substituted with X, Y and Z,
      (b') $-OH$,
      (c') $C_{1-6}$alkoxy,
      (d') $-CO_2H$,
      (e') $-CO_2-C_{1-6}$alkyl,
      (f') $-C_{3-7}$cycloalkyl, and
      (g') $-OR^{11}$,
    (iii) $C_{3-10}$alkenyl unsubstituted or substituted with one or more of the substituent(s) selected from:
      (a') phenyl, which is unsubstituted or substituted with X, Y and Z,
      (b') $-OH$,
      (c') $C_{1-6}$alkoxy,
      (d') $-CO_2H$,
      (e') $-CO_2-C_{1-6}$alkyl,
      (f') $-C_{3-7}$cycloalkyl, and
      (g') $-OR^{11}$,
    (iv) or where $R^8$ and $R^9$ and the N to which they are attached may form an unsubstituted or substituted 3–7-membered heterocyclic ring which may include one or two additional heteroatoms independently selected from the group consisting of O, $S(O)_p$, $NR^{18}$, wherein $R^{18}$ is hydrogen or $C_{1-6}$ alkyl unsubstituted or substituted by phenyl, and p is 0, 1 or 2, such as morpholine, thiomorpholine, piperidine, or piperizine,
  (h) $-NR^8CO-C_{1-6}$alkyl-$R^9$, wherein $R^9$ is as defined above,
  (i) $-NR^8CO_2-C_{1-6}$alkyl-$R^9$,
  (j) $-NR^8CONR^8R^9$,
  (k) $-OCONR^8R^9$,
  (l) $-COOR^8$,
  (m) $-CHO$,
  (n) phenyl,
  (o) substituted phenyl in which the substituents are X, Y and Z,
  (p) $-S(O)_p-C_{1-6}$alkyl, and
  (q) $-OR^{11}$;
(5) heteroaryl-$C_{1-10}$alkyl wherein one or more of the alkyl carbons is replaced by a group selected from:

—$NR^8$—, —O—, —$S(O)_p$—, —$CO_2$—, —$O_2C$—, —$CONR^8$—, —$NR^8CO$—, —$NR^8CONR^9$—;

(6) substituted heteroaryl-$C_{1-10}$alkyl wherein one or more of the alkyl carbons is replaced by a group selected from: —$NR^8$—, —O—, —$S(O)_p$—, —$CO_2$—, —$O_2C$—, —$CONR^8$—, —$NR^8CO$—, and —$NR^8CONR^9$—, the heteroaryl group is substituted with X, Y, and Z, and the alkyl group may be substituted with one or more of the substituent(s) selected from:
(a) hydroxy,
(b) oxo,
(c) $C_{1-6}$alkoxy,
(d) phenyl-$C_{1-3}$alkoxy,
(e) substituted phenyl-$C_{1-3}$alkoxy, in which the substituents on phenyl are X, Y and Z,
(f) —OCO—$C_{1-6}$alkyl,
(g) —$NR^8R^9$, wherein $R^8$ and $R^9$ are as defined above,
(h) —$NR^8CO$—$C_{1-6}$alkyl, wherein $R^8$ is as defined above,
(i) —$NR^8CO_2$—$C_{1-6}$alkyl,
(j) —$NR^8CONR^8R^9$,
(k) —$OCONR^8R^9$,
(l) —$COOR^8$,
(m) —CHO,
(n) phenyl,
(o) substituted phenyl in which the substituents are X, Y and Z,
(p) —$S(O)_p$—$C_{1-6}$alkyl, and
(q) —$OR^{11}$;

(7) heteroaryl-$C_{3-10}$alkenyl wherein alkenyl contains one to four double bonds;

(8) heteroaryl-$C_{3-10}$alkenyl wherein alkenyl contains one to four double bonds and wherein one or more of the alkyl carbons is replaced by a group selected from: —$NR^8$—, —O—, —$S(O)_p$—, —$CO_2$—, —$O_2C$—, —$CONR^8$—, —$NR^8CO$—, and —$NR^8CONR^9$—;

(9) substituted heteroaryl-$C_{3-10}$alkenyl wherein alkenyl contains one to four double bonds and wherein one or more of the alkyl carbons may be replaced by a group selected from: —$NR^8$—, —O—, —$S(O)_p$—, —$CO_2$—, —$O_2C$—, —$CONR^8$—, —$NR^8CO$—, —$NR^8CONR^9$, —$NR^8CONR^9$, the heteroaryl group is substituted with X, Y, and Z, and the alkyl group may be substituted with one or more of the substituent(s) selected from:
(a) hydroxy,
(b) oxo,
(c) $C_{1-6}$alkoxy,
(d) phenyl-$C_{1-3}$alkoxy,
(e) substituted phenyl-$C_{1-3}$alkoxy, in which the substituents on phenyl are X, Y and Z,
(f) —OCO—$C_{1-6}$alkyl,
(g) —$NR^8R^9$, wherein $R^8$ and $R^9$ as defined above,
(h) —$NR^8CO$—$C_{1-6}$alkyl, wherein $R^8$ is as defined above,
(i) —$NR^8CO_2$—$C_{1-6}$alkyl,
(j) —$NR^8CONR^8R^9$,
(k) —$OCONR^8R^9$,
(l) —$COOR^8$,
(m) —CHO,
(n) phenyl,
(o) substituted phenyl in which the substituents are X, Y and Z,
(p) —$S(O)_p$—$C_{1-6}$alkyl, and
(q) —$OR^{11}$;

$R^2$ is independently selected from:
(1) the definitions of $R^1$;
(2) hydroxy;
(3) phenyloxy;
(4) substituted phenyloxy in which the substituents are X, Y and Z;
(5) 1- or 2-naphthyloxy;
(6) substituted 1- or 2-naphthyloxy in which the substituents are X, Y and Z;
(7) biphenyloxy;
(8) substituted biphenyloxy in which the substituents are X, Y and Z;
(9) $C_{1-10}$alkoxy;
(10) substituted-$C_{1-10}$alkoxy in which one or more substituent(s) is(are) selected from:
(a) hydroxy,
(b) oxo,
(c) $C_{1-6}$alkoxy,
(d) phenyl-$C_{1-3}$alkoxy,
(e) substituted phenyl-$C_{1-3}$alkoxy, in which the substituents on phenyl are X, Y and Z,
(f) —OCO—$C_{1-6}$alkyl,
(g) —$NR^8R^9$, wherein $R^8$ and $R^9$ are as defined above
(h) —$NR^6CO$—$C_{1-6}$alkyl, wherein $R^6$ is as defined above,
(i) —$COOR^6$, wherein $R^6$ is as defined above,
(j) —CHO,
(k) phenyl,
(l) substituted phenyl in which the substituents are X, Y and Z,
(m) 1- or 2-naphthyl,
(n) substituted 1- or 2-naphthyl in which the substituents are X, Y and Z,
(o) biphenyl,
(p) substituted biphenyl in which the substituents are X, Y and Z,
(q) —$OR^{11}$, and
(r) —$S(O)_p$—$C_{1-6}$alkyl;

(11) $C_{3-10}$alkenyloxy;

(12) substituted $C_{3-10}$alkenyloxy in which one or more substituent(s) is(are) selected from:
(a) hydroxy,
(b) oxo,
(c) $C_{1-6}$alkoxy,
(d) phenyl-$C_{1-3}$alkoxy,
(e) substituted phenyl-$C_{1-3}$alkoxy, in which the substituents on phenyl are X, Y and Z,
(f) —OCO—$C_{1-6}$alkyl,
(g) —$NR^8R^9$, wherein $R^8$ and $R^9$ are as defined above
(h) —$NR^8CO$—$C_{1-6}$alkyl, wherein $R^8$ is as defined above,
(i) —$COOR^8$, wherein $R^8$ is as defined above,
(j) —CHO,
(k) phenyl,
(l) substituted phenyl in which the substituents are X, Y and Z,
(m) 1- or 2-naphthyl,
(n) substituted 1- or 2-naphthyl in which the substituents are X, Y and Z,
(o) biphenyl,
(p) substituted biphenyl in which the substituents are X, Y and Z,
(q) —$OR^{11}$, and
(r) —$S(O)_p$—$C_{1-6}$alkyl;

(13) $C_{3-10}$alkynyloxy;

(14) substituted $C_{3-10}$alkynyloxy in which one or more substituent(s) is(are) selected from:
(a) hydroxy, (b) oxo,
(c) $C_{1-6}$alkoxy,
(d) phenyl-$C_{1-3}$alkoxy,
(e) substituted phenyl-$C_{1-3}$alkoxy, in which the substituents on phenyl are X, Y and Z,
(f) —OCO—$C_{1-6}$alkyl,
(g) —$NR^8R^9$, wherein $R^8$ and $R^9$ are as defined above,
(h) —$NR^8CO$—$C_{1-6}$alkyl, wherein $R^8$ is as defined above,
(i) —$COOR^8$, wherein $R^8$ is as defined above,
(j) —CHO,
(k) phenyl,
(l) substituted phenyl in which the substituents are X, Y and Z,
(m) 1- or 2-naphthyl,
(n) substituted 1- or 2-naphthyl in which the substituents are X, Y and Z,
(o) biphenyl,
(p) substituted biphenyl in which the substituents are X, Y and Z,
(q) —$OR^{11}$; and
(15) —$OR^{11}$;

$R^7$ is selected from
(1) hydrogen, and
(2) $C_{1-10}$alkyl, unsubstituted or substituted with, one or more of the substitutent(s) selected from:
(a) hydroxy,
(b) oxo,
(c) $C_{1-6}$alkoxy,
(d) phenyl-$C_{1-3}$alkoxy,
(e) substituted phenyl-$C_{1-3}$alkoxy, in which the substituents on phenyl are X, Y and Z,
(f) —OCO—$C_{1-6}$alkyl, and
(g) —$NR^8R^9$, wherein $R^8$ and $R^9$ are as defined above;

$R^3$ is hydrogen, hydroxy, —$OR^{11}$, or $C_{1-6}$alkoxy;
$R^4$ is hydrogen, or $R^3$ and $R^4$ taken together form a double bond;
$R^5$ is
1) methyl,
2) ethyl,
3) propyl, or
4) allyl;
$R^{10}$ is hydrogen, hydroxy, —$OR^{11}$ or fluoro;
$R^{11}$ is selected from:
(a) —$PO(OH)O^-M^+$, wherein $M^+$ is a positively charged inorganic or organic counterion,
(b) —$SO_3^-M^+$,
(c) —$CO(CH_2)_qCO_2^-M^+$, wherein q is 1 to 3, and
(d) —CO—$C_{1-6}$alkyl-$NR^8R^9$, wherein $R^8$ and $R^9$ are as defined above and the alkyl is unsubstituted or substituted with one or more substituents selected from:
(i) hydroxy,
(ii) $C_{1-6}$alkoxy,
(iii) —$NR^{16}R^{17}$, wherein $R^{16}$ and $R^{17}$ are independently selected from: (a') hydrogen, and (b') $C_{1-6}$alkyl,
(iv) —$COOR^6$, wherein $R^6$ is as defined above,
(v) phenyl,
(iv) substituted phenyl in which the substituents are X, Y and Z,
(vii) heteroaryl,
(viii) —SH, and
(ix) —S—$C_{1-6}$alkyl;
W is O or (H,OH);
X, Y and Z independently are selected from:
(1) hydrogen,
(2) $C_{1-7}$alkyl,
(3) $C_{2-6}$alkenyl,
(4) halogen,
(5) —$(CH_2)_m$—$NR^8R^9$, wherein $R^8$ and $R^9$ are as defined above, and m is 0, 1 or 2,
(6) —CN,
(7) —CHO,
(8) —$CF_3$,
(9) —$SR^{12}$, wherein $R^{12}$ is hydrogen, $C_{1-6}$alkyl, trifluoromethyl, or phenyl,
(10) —$SOR^{12}$, wherein $R^{12}$ is as defined above,
(11) —$SO_2R^{12}$, wherein $R^{12}$ is as defined above,
(12) —$CONR^8R^9$, wherein $R^8$ and $R^9$ are as defined above,
(13) $R^{13}O(CH_2)_m$— wherein $R^{13}$ is hydrogen, $C_{1-3}$alkyl, hydroxy-$C_{2-3}$alkyl, phenyl, $R^{11}$ or naphthyl and m is as defined above,
(14) —$CH(OR^{14})(OR^{15})$, wherein $R^{14}$ and $R^{15}$ are $C_{1-3}$alkyl or taken together form an ethyl or propyl bridge,

(15) $R^{13}\overset{\overset{\displaystyle O}{\|}}{C}O(CH_2)_m$— wherein $R^{13}$ and m are as defined above,

(16) $R^{13}O\overset{\overset{\displaystyle O}{\|}}{C}(CH_2)_m$— wherein $R^{13}$ and m are as defined above, and
(17) —$OR^{11}$;
or any two of X, Y and Z may be joined to form a saturated ring having 5, 6 or 7 ring atoms, said ring atoms comprising 1 or 2 oxygen atoms, the remaining ring atoms being carbon, such as dioxolanyl or dioxanyl; and
n is 1 or 2.

The compounds of the present invention have asymmetric centers and this invention includes all of the optical isomers and mixtures thereof.

In addition compounds with carbon-carbon double bonds may occur in Z- and E- forms with all isomeric forms of the compounds being included in the present invention.

When any variable (e.g., alkyl, aryl, $R^5$, $R^6$, $R^7$, $R^8$, $R^9$, $R^{10}$, $R^{11}$, $R^{12}$, $R^{13}$, etc.) occurs more than one time in any variable or in Formula I, its definition on each occurrence is independent of its definition at every other occurrence.

As used herein, "alkyl" is intended to include both branched- and straight-chain saturated aliphatic hydrocarbon groups having the specified number of carbon atoms, representative examples being methyl, ethyl, isopropyl, tert-butyl, and sec-butyl; "alkoxy" represents an alkyl group of indicated number of carbon atoms attached through an oxygen bridge; and "$C_3$-$C_7$-cycloalkyl" is intended to include saturated ring groups, such as cyclopropyl, cyclobutyl, cyclopentyl, cyclohexyl and cycloheptyl.

"Alkenyl" is intended to include hydrocarbon chains of either a straight- or branched-configuration and one unsaturation, which may occur at any point along the chain, such as ethenyl, propenyl, butenyl, pentenyl, and the like, and includes E and Z forms, where applicable; and "arylalkyl" represents aryl groups as herein defined which are attached through a straight- or branched-chain alkyl group of specified number of carbon atoms, such as, for example, benzyl, phenethyl, 3,3-diphenylpropyl, and the like; and "heteroarylalkyl" represents heteroaryl groups as herein defined which are attached through a straight or branched chain alkyl group of from one to ten carbon atoms.

As will be understood by those skilled in the art, pharmaceutically acceptable salts include, but are not limited to salts with inorganic acids such as hydrochloride, sulfate, phosphate, diphosphate, hydrobromide, and nitrate or salts with an organic acid such as malate, maleate, fumarate, tartrate, succinate, citrate, acetate, lactate, methanesulfonate, p-toluenesulfonate or palmoate, salicylate and stearate. Similarly pharmaceutically acceptable cations include, but are not limited to sodium, potassium, calcium, aluminum, lithium and ammonium (especially ammonium salts with amines of the formula $HNR^6R^7$).

The heteroaryl group as used herein includes acridine, carbazole, cinnoline, dibenzofuran, dibenzothiophene, quinoxaline, pyrrazole, benzoxazole, indole, imidazole, thiazole, benzothiazole, benzotriazole, furan, benzofuran, benzimidazole, quinoline, isoquinoline, oxazole, pyrazine, pyridazine, pyridine, pyrimidine, pyrrole which are optionally substituted by from one- to three-members independently selected from the group consisting of: alkyl, alkenyl, halogen, carboxyl, CHO, amino, mono-alkylamino, di-alkylamino, aminoalkyl, monoalkylaminoalkyl, dialkylaminoalkyl, alkylthio, alkylsulfinyl, alkysulfonyl, trifluoromethyl, amido, mono-alkylamido, dialkylamido, hydroxy, hydroxyalkyl, alkoxy, alkoxyalkyl, formamido, alkyl-$CO_2$—, formamidoalkyl, alkyl-$CO_2$-alkyl-, carboxyl, alkyl-$CO_2H$, alkyl-$O_2C$—, alkyl-$O_2C$-alkyl-, and $OR^{11}$.

"Halo" or "halogen", as used herein, means fluoro, chloro, bromo and iodo.

The term "heteroaryl" as utilized herein is intended to include the following heteroaromatic groups which may include X, Y and Z substitution as indicated and wherein Q is —$N(R^8)$—, —O—, or —S—:

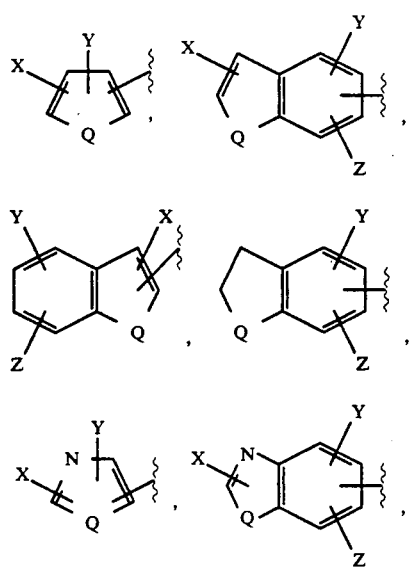

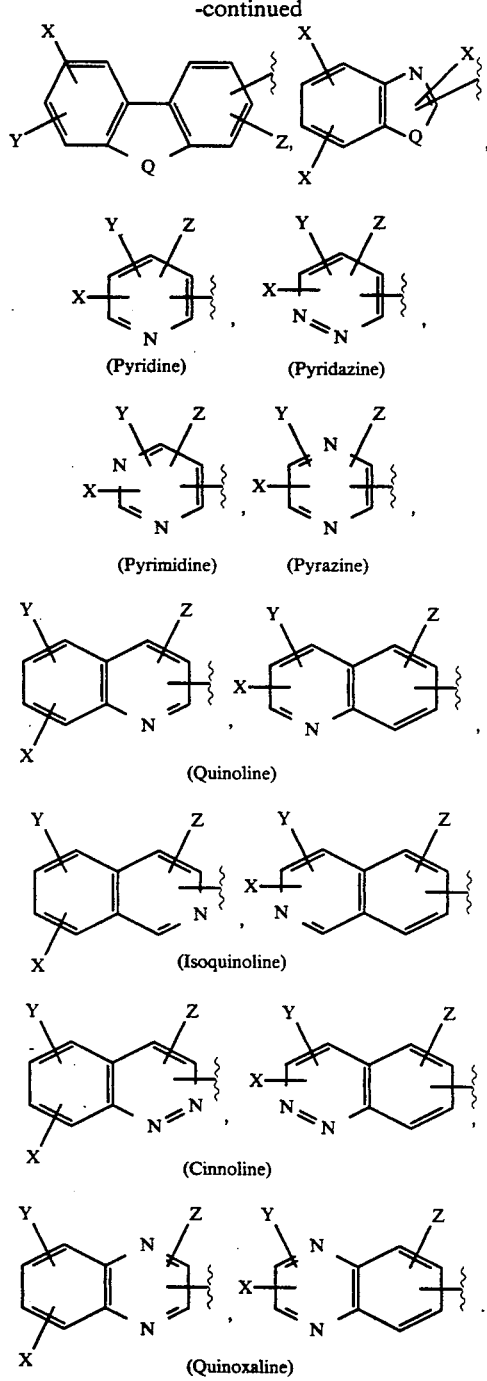

The aryl or aromatic group may include phenyl or naphthyl which are optionally substituted by from one- to three-members independently selected from the group consisting of: alkyl, alkenyl, halogen, carboxyl, CHO, amino, mono-alkylamino, di-alkylamino, aminoalkyl, mono-alkylaminoalkyl, di-alkylaminoalkyl, alkylthio, alkylsulfinyl, alkysulfonyl, trifluoromethyl, amido, mono-alkylamido, dialkylamido, hydroxy, hydroxyalkyl, alkoxy, $R^{11}O$-alkyl, alkoxyalkyl, formamido, alkyl-$CO_2$—, formamidoalkyl, alkyl-$CO_2$-alkyl-, carboxyl, alkyl-$CO_2H$, alkyl-$O_2C$-, alkyl-$O_2C$-alkyl- and $OR^{11}$.

In the compound of formula I it is preferred that heteroaryl is selected from the group consisting of:

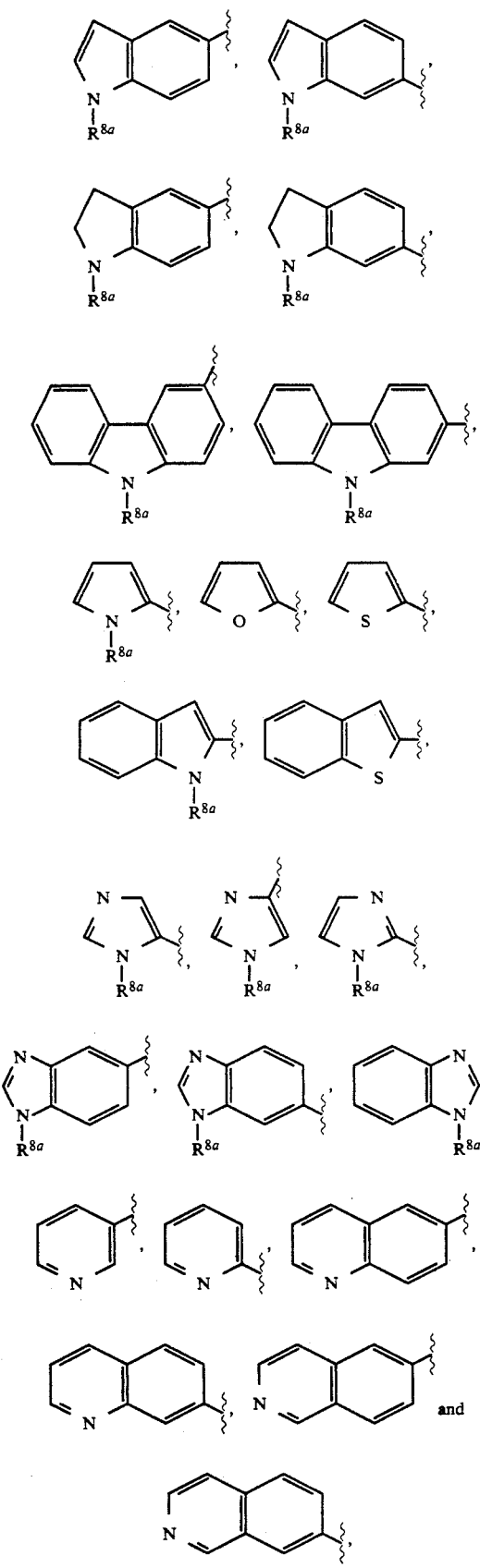

wherein $R^{8a}$ is selected from:

(a) hydrogen;
(b) $C_{1-10}$alkyl, unsubstituted or substituted with one or more substitutents selected from:
  (i) phenyl,
  (ii) substituted phenyl in which the substitutents are X, Y and Z,
  (iii) hydroxy,
  (iv) $C_{1-6}$alkoxy,
  (v) —$COOR^{16}$,
  (vi) —$NR^{16}R^{17}$, and
  (vii) —$OR^{11}$;
(c) $C_{3-10}$alkenyl, unsubstituted or substituted with one or more substitutents selected from:
  (i) phenyl,
  (ii) substituted phenyl in which the substitutents are X, Y and Z,
  (iii) hydroxy,
  (iv) $C_{1-6}$alkoxy,
  (v) —$COOR^{16}$,
  (vi) —$NR^{16}R^{17}$, and
  (vii) —$OR^{11}$.

In the compound of formula I it is also preferred that $R^2$ is selected from:
(1) hydroxy,
(2) methoxy,
(3) ethoxy,
(4) propoxy,
(5) allyloxy,
(6) —$OR^{11}$,
(7) —O—$C_{2-3}$alkyl—OH, and
(8) —O—$C_{2-3}$alkyl—$OR^{11}$;

$R^3$ is selected from:
(1) hydrogen,
(2) hydroxy,
(3) —$OR^{11}$, or $R^3$ and $R^4$ taken together form a double bond; $R^{10}$ is hydrogen, hydroxy, fluoro or —$OR^{11}$;
W is O; and
n is 2.

In one embodiment of the present invention, heteroaryl is indole, which may be represented by:

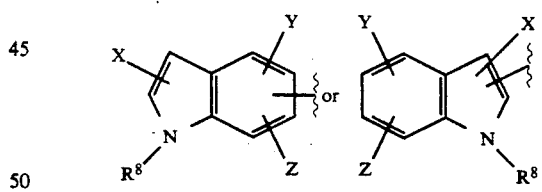

wherein $R^8$, X, Y and Z are as defined above,

In another embodiment of the present invention, heteroaryl is imidazole, which may be represented by:

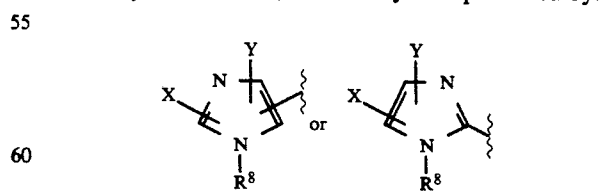

wherein $R^8$, X and Y are as defined above.

Preferred compounds of the present invention are the compounds identified as follows:

17-Ethyl-1-hydroxy-12-[2'-(4''-β-(2-furanyl)methylamino-3''-methoxycyclohexyl)-1'-methylvinyl]-23,25-dimethoxy-13,19,21,27-tetramethyl-11,28-dioxa-4- azatricyclo[22.3.1.0⁴,⁹]octacos-18-ene-2,3,10,16-tetraone;

17-Ethyl-1,14-dihydroxy-12-[2'-(4"-(2-furanyl)methylamino-3"-methoxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-Ethyl-1-hydroxy-12-[2'-(4"-(2-thiophene)methylamino-3"-methoxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-Ethyl-1,14-dihydroxy-12-[2'-(2-thiophene)methylamino-3"-methoxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-Ethyl-1,14-dihydroxy-12-[2'-(4"-(2-thiophene)methylamino-3"-hydroxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-Ethyl-1,14-dihydroxy-12-[2'-(4"-(2-thiophene)amino-3"-methoxycyclohexyl)-1'-methylvinyl]-23,25-dimethoxy-13,19,21,27-tetramethyl-11,28-dioxa-4-azatricyclo-[22.3.1.0⁴,⁹]octacos-18-ene-2,3,10,16-tetraone;

17-Ethyl-1-hydroxy-12-[2'-(4"-β-(pyrid-2-yl)methylamino-3"-methoxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-Ethyl-1-hydroxy-12-[2'-(4"-β-(pyrid-4-yl)methylamino-3"-methoxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-Ethyl-1-hydroxy-12-[2'-(4"-β-(1-methyl-pyrid-2-yl)amino-3"-methoxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-Ethyl-1-hydroxy-12-[2'-(4"-β-(imidazol-2-yl)methylamino-3"-methoxycyclohexyl)-1'-methylvinyl]-23,25-dimethoxy-13,19,21,27-tetramethyl-11,28-dioxa-4-azatricyclo-[22.3.1.0⁴,⁹]octacos-18-ene-2,3,10,16-tetraone;

17-Ethyl-1-hydroxy-12-[2'-(4"-β-(imidazolin-2-yl)methylamino-3"-methoxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-Ethyl-1-hydroxy-12-[2'-(4"-β-(1-methylindol-5-yl)methylamino-3"-methoxycyclohexyl)-1'-methylvinyl]-23,-25-dimethoxy-13,19,21,27-tetramethyl-11,28-dioxa-4-azatricyclo[22.3.1.0⁴,⁹]octacos-18-ene-2,3,10,16-tetraone;

17-Ethyl-1-hydroxy-12-[2'-(4"-α-(1-methylindol-5-yl)methylamino-3"-methoxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-Ethyl-1-hydroxy-12-[2'-(4"-β-(indol-3-yl)methylamino-3"-methoxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-Ethyl-1-hydroxy-12-[2'-(4"-β-(pyrrol-2-yl)methylamino-3"-methoxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-Ethyl-1,14-dihydroxy-12-[2'-(4"-(2-benzothienyl)amino-3"-methoxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-Ethyl-1-hydroxy-12-[2'-(4"-β-(1-methyl-5-indolyl)amino-3"-methoxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-Ethyl-1-hydroxy-12-[2'-(4"-α-(1-methyl-5-indolyl)amino-3"-methoxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-Allyl-1,14-dihydroxy-12-[2'-(4"-(5-indolyl)amino-3"-methoxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-Ethyl-1,14-dihydroxy-12-[2'-(4"-(5-indolyl)amino-3"-ethoxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-Allyl-1,14-dihydroxy-12-[2'-(4"-(5-indolyl)amino-3"-ethoxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-Allyl-1-hydroxy-12-[2'-(4"-(5-indolyl)amino-3"-methoxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-Ethyl-1,14-dihydroxy-12-[2'-(4"-(1-N-methyl-5-indolyl)amino-3"-methoxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-Ethyl-1,14-dihydroxy-12-[2'-(4"-(1-N-methyl-5-indolyl)amino-3"-hydroxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-Ethyl-1,14,20-trihydroxy-12-[2'-(4"-(1-N-methyl-5-indolyl)amino-3"-methoxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-Ethyl-1,20-dihydroxy-12-[2'-(4"-(1-N-methyl-5-indolyl)amino-3"-methoxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-Allyl-1,14-dihydroxy-12-[2'-(4"-(1-N-methyl-5-indolyl)amino-3"-methoxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-Ethyl-1-hydroxy-12-[2'-(4"-(1-N-methyl-5-indolyl)amino-3"-methoxycyclohexyl)-1'-methylvinyl]-23,25-dimethoxy-13,19,21,27-tetramethyl- 11,28-dioxa-4-azatricyclo[22.3.1.0^4,9]octacos-18-ene-2,3,10,16-tetraone;

17-Ethyl-1,14-dihydroxy-12-[2'-(4"-(1-N-methyl-5-indolyl)amino-3"-ethoxycyclohexyl)-1'-methylvinyl]-23,-25-dimethoxy-13,19,21,27-tetramethyl-11,28-dioxa-4-azatricyclo[22.3.1.0^4,9]octacos-18-ene-2,3,10,16-tetraone;

17-Allyl-1,14-dihydroxy-12-[2'-(1-N-methyl-5-indolyl)amino-3"-ethoxycyclohexyl)-1'-methylvinyl]-23,25-dimethoxy-13,19,21,27-tetramethyl-11,28-dioxa-4-azatricyclo[22.3.1.0^4,9]octacos-18-ene-2,3,10,16-tetraone;

17-Ethyl-1,14-dihydroxy-12-[2'-(4"-(1-N-ethyl-5-indolyl)amino-3"-ethoxycyclohexyl)-1'-methylvinyl]-23,25-dimethoxy-13,19,21,27-tetramethyl-11,28-dioxa-4-azatricyclo[22.3.1.0^4,9]octacos-18-ene-2,3,10,16-tetraone;

17-Allyl-1-hydroxy-12-[2'-(4"-(1-N-methyl-5-indolyl)amino-3"-methoxycyclohexyl)-1'-methylvinyl]-23,25-dimethoxy-13,19,21,27-tetramethyl-11,28-dioxa-4-azatricyclo[22.3.1.0^4,9]octacos-18-ene-2,3,10,16-tetraone;

17-Ethyl-1,14-dihydroxy-12-[2'-(4"-(1-N-methyl-5-indolyl)amino-3"-allyloxycyclohexyl)-1'-methylvinyl]-23,25-dimethoxy-13,19,21,27-tetramethyl-11,28-dioxa-4-azatricyclo[22.3.1.0^4,9]octacos-18-ene-2,3,10,16-tetraone;

17-Ethyl-1-hydroxy-12-[2'-(4"-(1-N-methyl-5-indolyl)amino-3"-allyloxycyclohexyl)-1'-methylvinyl]-23,25-dimethoxy-13,19,21,27-tetramethyl-11,28-dioxa-4-azatricyclo[22.3.1.0^4,9]octacos-18-ene-2,3,10,16-tetraone;

17-Ethyl-1,14-dihydroxy-12-[2'-(4"-(1-N-methyl-5-indolyl)amino-3"-n-propyloxycyclohexyl)-1'-methylvinyl]23,25-dimethoxy-13,19,21,27-tetramethyl-11,28-dioxa-4-azatricyclo[22.3.1.0^4,9]octacos-18-ene-2,3,-10,16-tetraone;

17-Ethyl-1-hydroxy-12-[2'-(4"-(1-N-methyl-5-indolyl)amino-3"-n-propyloxycyclohexyl)-1'-methylvinyl]-23,-25-dimethoxy-13,19,21,27-tetramethyl-11,28-dioxa-4-azatricyclo[22.3.1.0^4,9]octacos-18-ene-2,3,10,16-tetraone;

17-Ethyl-1,14-dihydroxy-12-[2'-(4"-(1-N-methyl-5-indolyl)amino-3"-i-propyloxycyclohexyl)-1'-methylvinyl]23,25-dimethoxy-13,19,21,27-tetramethyl-11,28-dioxa-4-azatricyclo[22.3.1.0^4,9]octacos-18-ene-2,3,-10,16-tetraone;

17-Ethyl-1,14-dihydroxy-12-[2'-(4"-(1-N-ethyl-5-indolyl)amino-3"-methoxycyclohexyl)-1'-methylvinyl]-23,25-dimethoxy-13,19,21,27-tetramethyl-11,28-dioxa-4-azatricyclo[22.3.1.0^4,9]octacos-18-ene-2,3,10,16-tetraone;

17-Ethyl-1,14-dihydroxy-12-[2'-(4"-(1-N-ethyl-5-indolyl)amino-3"-hydroxycyclohexyl)-1'-methylvinyl]-23,25-dimethoxy-13,19,21,27-tetramethyl-11,28-dioxa-4-azatricylo-[22.3.1.0^4,9]octacos-18-ene-2,3,10,16-tetraone;

17-Allyl-1,14-dihydroxy-12-[2'-(4"-(1-N-ethyl-5-indolyl)amino-3"-methoxycyclohexyl)-1'-methylvinyl]-23,25-dimethoxy-13,19,21,27-tetramethyl-11,28-dioxa-4-azatricyclo[22.3.1.0^4,9]octacos-18-ene-2,3,10,16-tetraone;

17-Allyl-1,14-dihydroxy-12-[2'-(4"-(1-N-ethyl-5-indolyl)amino-3"-hydroxycyclohexyl)-1'-methylvinyl]-23,25-dimethoxy-13,19,21,27-tetramethyl-11,28-dioxa-4-azatricyclo[22.3.1.0^4,9]octacos-18-ene-2,3,10,16-tetraone;

17-Ethyl-1-hydroxy-12-[2'-(4"'-(1-N-ethyl-5-indolyl)amino-3"-methoxycyclohexyl)-1'-methylvinyl]-23,25-dimethoxy-13,19,21,27-tetramethyl-11,28-dioxa-4-azatricyclo[22.3.1.0^4,9]octacos-18-ene-2,3,10,16-tetraone;

17-Allyl-1-hydroxy-12-[2'-(4"-(1-N-ethyl-5-indolyl)amino-3"-methoxycyclohexyl)-1'-methylvinyl]-23,25-dimethoxy-13,19,21,27-tetramethyl-11,28-dioxa-4-azatricyclo[22.3.1.0^4,9]octacos-18-ene-2,3,10,16-tetraone;

17-Allyl-1,14-dihydroxy-12-[2'-(4"-(1N-ethyl-5-indolyl)amino-3"-ethoxycyclohexyl)-1'-methylvinyl]-23,25-dimethoxy-13,19,21,27-tetramethyl-11,28-dioxa-4-azatricyclo[22.3.1.0^4,9]octacos-18-ene-2,3,10,16-tetraone;

17-Ethyl-1,14-dihydroxy-12-[2'-(4"-(1-N-propyl-5-indolyl)amino-3"-methoxycyclohexyl)-1'-methylvinyl]-23,25-dimethoxy-13,19,21,27-tetramethyl-11,28-dioxa-4-azatricyclo[22.3.1.0^4,9]octacos-18-ene-2,3,10,16-tetraone;

17-Ethyl-1,14-dihydroxy-12-[2'-(4'-(1-N-propyl-5-indolyl)amino-3"-hydroxycyclohexyl)-1'-methylvinyl]-23,25-dimethoxy-13,19,21,27-tetramethyl-11,28-dioxa-4-azatricyclo[22.3.1.0^4,9]octacos-18-ene-2,3,10,16-tetraone;

17-Allyl-1,14-dihydroxy-12-[2'-(4"-(1-N-propyl-5-indolyl)amino-3"-methoxycyclohexyl)-1'-methylvinyl]-23,25-dimethoxy-13,19,21,27-tetramethyl-11,28-dioxa-4-azatricyclo[22.3.1.0^4,9]octacos-18-ene-2,3,10,16-tetraone;

17-Allyl-1,14-dihydroxy-12-[2'-(4"-(1-N-propyl-5-indolyl)amino-3"-hydroxycyclohexyl)-1'-methylvinyl]-23,25-dimethoxy-13,19,21,27-tetramethyl-11,28-dioxa-4-azatricyclo[22.3.1.0^4,9]octacos-18-ene-2,3,10,16-tetraone;

17-Ethyl-1-hydroxy-12-[2'-(4"-(1-N-propyl-5-indolyl)amino-3"-methoxycyclohexyl)-1'-methylvinyl]-23,25-dimethoxy-13,19,21,27-tetramethyl-11,28-dioxa-4-azatricyclo[22.3.1.0^4,9]octacos-18-ene-2,3,10,16-tetraone;

17-Allyl-1-hydroxy-12-[2'-(4"-(1-N-propyl-5-indolyl)amino-3"-methoxycyclohexyl)-1'-methylvinyl]-23,25-dimethoxy-13,19,21,27-tetramethyl-11,28-dioxa-4-azatricyclo[22.3.1.0^4,9]octacos-18-ene-2,3,10,16-tetraone;

17-Ethyl-1,14-dihydroxy-12-[2'-(4"-(1-N-propyl-5-indolyl)amino-3"-ethoxycyclohexyl)-1'-methylvinyl]-23,25-dimethoxy-13,19,21,27-tetramethyl-11,28-dioxa-4-azatricyclo[22.3.1.0^4,9]octacos-18-ene-2,3,10,16-tetraone;

17-Allyl-1,14-dihydroxy-12-[2'-(4"-(1-N-propyl-5-indolyl)amino-3"-ethoxycyclohexyl)-1'-methylvinyl]-23,25-dimethoxy-13,19,21,27-tetramethyl-11,28-dioxa-4-azatricyclo[22.3.1.0^4,9]octacos-18-ene-2,3,10,16-tetraone;

17-Ethyl-1,14-dihydroxy-12-[2'-(4"-(1-N-allyl-5-indolyl)amino-3"-methoxycyclohexyl)-1'-methylvinyl]-23,25-dimethoxy-13,19,21,27-tetramethyl-11,28-dioxa-4-azatricyclo[22.3.1.0^4,9]octacos-18-ene-2,3,10,16-tetraone;

17-Ethyl-1,14-dihydroxy-12-[2'-(4"-(1-N-allyl-5-indolyl)amino-3"-hydroxycyclohexyl)-1'-methylvinyl]-23,25-dimethoxy-13,19,21,27-tetramethyl-11,28-dioxa-4-azatricyclo[22.3.1.0^4,9]octacos-18-ene-2,3,10,16-tetraone;

17-Allyl-1,14-dihydroxy-12-[2'-(4"-(1-N-allyl-5-indolyl)amino-3"-methoxycyclohexyl)-1'-methylvinyl]-23,25-dimethoxy-13,19,21,27-tetramethyl- 11,28-dioxa-4-azatricyclo[22.3.1.0⁴,⁹]octacos-18-ene-2,3,10,16-tetraone;

17-Allyl-1,14-dihydroxy-12-[2'-(4''-(1-N-allyl-5-indolyl)amino-3''-hydroxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-Ethyl-1-hydroxy-12-[2'-(4''-(1-N-allyl-5-indolyl)amino-3''-methoxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-Allyl-1-hydroxy-12-[2'-(4''-(1-N-allyl-5-indolyl)amino-3''-methoxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-Ethyl-1,14-dihydroxy-12-[2'-(4''-(1-N-allyl-5-indolyl)amino-3''-ethoxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-Allyl-1,14-dihydroxy-12-[2'-(4''-(1-N-allyl-5-indolyl)amino-3''-ethoxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-Ethyl-1,14-dihydroxy-12-[2'-(4''-(1-N-2-hydroxyethyl-5-indolyl)amino-3''-methoxycyclohexyl)-1'-methyl-vinyl]-23,25-dimethoxy-13,19,21,27-tetramethyl-11,28-dioxa-4-azatricyclo[22.3.1.0⁴,⁹]octacos-18-ene-2,3,10,16-tetraone;

17-Ethyl-1,14-dihydroxy-12-[2'-(4''-(1-N-2-hydroxyethyl-5-indolyl)amino-3''-hydroxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-Allyl-1,14-dihydroxy-12-[2'-(4''-(1-N-2-hydroxyethyl-5-indolyl)amino-3''-methoxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-Allyl-1,14-dihydroxy-12-[2'-(4'''-(1-N-hydroxyethyl-5-indolyl)amino-3''-hydroxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-Ethyl-1,14-dihydroxy-12-[2'-(4''-(1-N-benzyl-5-indolyl)amino-3''-methoxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-Ethyl-1,14-dihydroxy-12-[2'-(4''-(1-N-benzyl-5-indolyl)amino-3''-hydroxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-Allyl-1,14-dihydroxy-12-[2'-(4''-(1-N-benzyl-5-indolyl)amino-3''-methoxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-Allyl-1,14-dihydroxy-12-[2'-(4''-(1-N-benzyl-5-indolyl)amino-3''-hydroxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-Ethyl-1-hydroxy-12-[2'-(4''-(1-N-benzyl-5-indolyl)amino-3''-methoxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-Allyl-1-hydroxy-12-[2'-(4''-(1-N-benzyl-5-indolyl)amino-3''-methoxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-Ethyl-1,14-dihydroxy-12-[2'-(4''-(1-N-benzyl-5-indolyl)amino-3''-ethoxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-Allyl-1,14-dihydroxy-12-[2'-(4''-(1-N-benzyl-5-indolyl)amino-3''-ethoxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-Ethyl-1,14-dihydroxy-12-[2'-(4''-(1-N-cyclopropyl-5-indolyl)amino-3''-methoxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-Ethyl-1,14-dihydroxy-12-[2'-(4''-(1-N-cyclopropyl-5-indolyl)amino-3''-hydroxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-Allyl-1,14-dihydroxy-12-[2'-(4''-(1-N-cyclopropyl-5-indolyl)amino-3''-methoxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-Allyl-1,14-dihydroxy-12-[2'-(4''-(1-N-cyclopropyl-5-indolyl)amino-3''-hydroxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone.

17-Ethyl-1,14-dihydroxy-12-[2'-(4''-(1-N-cyclopropyl-5-indolyl)amino-3''-ethoxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-Allyl-1,14-dihydroxy-12-[2'-(4''-(1-N-cyclopropyl-5-indolyl)amino-3''-ethoxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-Ethyl-1-hydroxy-12-[2'-(4''-(1-N-cyclopropyl-5-indolyl)amino-3''-methoxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-Allyl-1-hydroxy-12-[2'-(4''-(1-N-cyclopropyl-5-indolyl)amino-3''-methoxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-Ethyl-1-hydroxy-12-[2'-(4''-methoxy-N-tryptophanylcarbonylmethylamino-3''-methoxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-Ethyl-1-hydroxy-12-[2'-(4''-3-indolylethylaminocarbonylmethylamino-3''-methoxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-Ethyl-1,14-dihydroxy-12-[2'-(4''-(5-indolyl)methylamino-3''-methoxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone 17-Ethyl-1-hydroxy-12-[2'-(4''-(5-indolyl)methylamino-3''-methoxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-Allyl-1,14-dihydroxy-12-[2'-(4''-(5-indolyl)methylamino-3''-methoxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-Ethyl-1,14-dihydroxy-12-[2'-(4''-(5-indolyl)methylamino-3''-ethoxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-Allyl-1,14-dihydroxy-12-[2'-(4''-(5-indolyl)methylamino-3''-ethoxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-Allyl-1-hydroxy-12-[2'-(4''-(5-indolyl)methylamino-3''-methoxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-Ethyl-1,14-dihydroxy-12-[2'-(4''-(1-N-methyl-5-indolyl)methylamino-3''-methoxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-Ethyl-1,14-dihydroxy-12-[2'-(4''-(1-N-methyl-5-indolyl)methylamino-3''-hydroxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-Ethyl-1,14,20-trihydroxy-12-[2'-(4''-(1-N-methyl-5-indolyl)methylamino-3''-methoxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-Ethyl-1,20-dihydroxy-12-[2'-(4''-(1-N-methyl-5-indolyl)methylamiono-3''-methoxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-Allyl-1,14-dihydroxy-12-[2'-(4''-(1-N-methyl-5-indolyl)amino-3''-methoxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-Ethyl-1-hydroxy-12-[2'-(4''-(1-N-methyl-5-indolyl)methylamino-3''-methoxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-Ethyl-1,14-dihydroxy-12-[2'-(4''-(1-N-methyl-5-indolyl)methylamino-3''-ethoxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-Allyl-1,14-dihydroxy-12-[2'-(4''-(1-N-methyl-5-indolyl)amino-3''-ethoxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-Ethyl-1,14-dihydroxy-12-[2'-(4''-(1-N-ethyl-5-indolyl)methylamino-3''-ethoxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-Allyl-1-hydroxy-12-[2'-(4''-(1-N-methyl-5-indolyl)methylamino-3''-methoxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-Ethyl-1,14-dihydroxy-12-[2'-(4''-(1-N-methyl-5-indolyl)methylamino-3''-allyloxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-Ethyl-1-hydroxy-12-[2'-(4''-(1-N-methyl-5-indolyl)methylamino-3''-allyloxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-Ethyl-1,14-dihydroxy-12-[2'-(4''-(1-N-methyl-5-indolyl)methylamino-3''-n-propyloxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-Ethyl-1-hydroxy-12-[2'-(4''-(1-N-methyl-5-indolyl)methylamino-3''-n-propyloxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-Ethyl-1,14-dihydroxy-12-[2'-(4''-(1-N-methyl-5-indolyl)methylamino-3''-i-propyloxycyclohexyl)-1'-methylvinyl]-23,25-dimethoxy-13,19,21,27-tetramethyl-11,28-dioxa-4-azatricyclo[22.3.1.0⁴,⁹]octacos018-ene-2,3,10,16-tetraone;

17-Ethyl-1,14-dihydroxy-12-[2'-(4''-(1-N-ethyl-5-indolyl)methylamino-3''-methoxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-Ethyl-1,14-dihydroxy-12-[2'-(4''-(1-N-ethyl-5-indolyl)methylamino-3''-hydroxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-Allyl-1,14-dihydroxy-12-[2'-(4''-(1-N-ethyl-5-indolyl)methylamino-3''-methoxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-Allyl-1,14-dihydroxy-12-[2'-(4'-(1-N-ethyl-5-indolyl)amino-3''-hydroxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-Ethyl-1-hydroxy-12-[2'-(4''-(1-N-ethyl-5-indolyl)methylamino-3''-methoxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-Allyl-1-hydroxy-12-[2'-(4''-(1-N-ethyl-5-indolyl)methylamino-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-Allyl-1,14-dihydroxy-12-[2'-(4''-(1-N-ethyl-5-indolyl)amino-3''-ethoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-Ethyl-1,14-dihydroxy-12-[2'-(4''-(1-N-propyl-5-indolyl)methylamino-3''-methoxycyclohexyl)-1'-methylvinyl]23,25-dimethoxy-13,19,21,27-tetramethyl-11,28-dioxa-4-azatricyclo[22.3.1.0$^{4,9}$]octacos-18-ene-2,3,10,16-tetraone;

17-Ethyl-1,14-dihydroxy-12-[2'-(4''-(1-N-propyl-5-indolyl)methylamino-3''-hydroxycyclohexyl)-1'-methylvinyl]23,25-dimethoxy-13,19,21,27-tetramethyl-11,28-dioxa-4-azatricyclo[22.3.1.0$^{4,9}$]octacos-18-ene-2,3,10,16-tetraone;

17-Allyl-1,14-dihydroxy-12-[2'-(4''-(1-N-propyl-5--indolyl)methylamino-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-Allyl-1,14-dihydroxy-12-[2'-(4''-(1-N-propyl-5--indolyl)methylamino-3''-hydroxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-Ethyl-1-hydroxy-12-[2'-(4''-(1-N-propyl-5-indolyl)methylamino-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-Allyl-1-hydroxy-12-[2'-(4''-(1-N-propyl-5-indolyl)methylamino-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-Ethyl-1,14-dihydroxy-12-[2'-(4''-(1-N-propyl-5-indolyl)amino-3''-ethoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-Allyl-1,4-dihydroxy-12-[2'-(4''-(1-N-propyl-5-indolyl)methylamino-3''-ethoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-Ethyl-1,14-dihydroxy-12-[2'-(4''-(1-N-allyl-5-indolyl)methylamino-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-Ethyl-1,14-dihydroxy-12-[2'-(4''-(1-N-allyl-5-indolyl)methylamino-3''-hydroxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-Allyl-1,14-dihydroxy-12-[2'-(4''-(1-N-allyl-5-indolyl)methylamino-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-Allyl-1,14-dihydroxy-12-[2'-(4''-(1-N-allyl-5-indolyl)methylamino-3''-hydroxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-Ethyl-1-hydroxy-12-[2'-(4''-(1-N-allyl-5-indolyl)methylamino-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-Allyl-1-hydroxy-12-[2'-(4''-(1-N-allyl-5-indolyl)methylamino-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-Ethyl-1,14-dihydroxy-12-[2'-(4''-(1-N-allyl-5-indolyl)methylamino-3''-ethoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-Allyl-1,14-dihydroxy-12-[2'-(4''-(1-N-allyl-5-indolyl)methylamino-3''-ethoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-Ethyl-1,14-dihydroxy-12-[-2'-(4''-(1-N-2-hydroxyethyl-5-indolyl)methylamino-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-Ethyl-1,14-dihydroxy-12-[-2'-(4''-(1-N-2-hydroxyethyl-5-indolyl)methylamino-3''-hydroxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-Allyl-1,14-dihydroxy-12-[-2'-(4''-(1-N-2-hydroxyethyl-5-indolyl)methylamino-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-Allyl-1,14-dihydroxy-12-[2'-(4''-(1-N-hydroxyethyl-5-indolyl)methylamino-3''-hydroxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-Ethyl-1,14-dihydroxy-12-[2'-(4''-(1-N-benzyl-5-indolyl)methylamino-3''-methoxycyclohexyl)-1'-methylvinyl]23,25-dimethoxy-13,19,21,27-tetramethyl-11,28-dioxa-4-azatricyclo[22.3.1.0$^{4,9}$]octacos-18-ene-2,3,10,16-tetraone;

17-Ethyl-1,14-dihydroxy-12-[2'-(4''-(1-N-benzyl-5--indolyl)methylamino-3''-hydroxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-Allyl-1,14-dihydroxy-12-[2'-(4''-(1-N-benzyl-5--indolyl)methylamino-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-Allyl-1,14-dihydroxy-12-[2'-(4''-(1-N-benzyl-5--indolyl)methylamino-3''-hydroxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-Ethyl-1-hydroxy-12-[2'-(4''-(1-N-benzyl-5-indolyl)methylamino-3''-methoxycyclohexyl)-1'-methylvinyl]-23,25-dimethoxy-13,19,21,27-tetramethyl- 11,28-dioxa-4-azatricyclo[22.3.1.0^{4,9}]octacos-18-ene-2,3,10,16-tetraone;

17-Allyl-1-hydroxy-12-[2'-(4''-(1-N-benzyl-5-indolyl)methylamino-3''-methoxycyclohexyl)-1'-methylvinyl]-23,25-dimethoxy-13,19,21,27-tetramethyl-11,28-dioxa-4-azatricyclo[22.3.1.0^{4,9}]octacos-18-ene-2,3,10,16-tetraone;

17-Ethyl-1,14-dihydroxy-12-[2'-(4''-(1-N-benzyl-5-indolyl)methylamino-3''-ethoxycyclohexyl)-1'-methylvinyl]23,25-dimethoxy-13,19,21,27-tetramethyl-11,28-dioxa-4-azatricyclo[22.3.1.0^{4,9}]octacos-18-ene-2,3,10,16-tetraone;

17-Allyl-1,14-dihydroxy-12-[2'-(4''-(1-N-benzyl-5-indolyl)methylamino-3''-ethoxycyclohexyl)-1'-methylvinyl]23,25-dimethoxy-13,19,21,27-tetramethyl-11,28-dioxa-4-azatricyclo[22.3.1.0^{4,9}]octacos-18-ene-2,3,10,16-tetraone;

17-Ethyl-1,14-dihydroxy-12-[2'-(4''-(1-N-cyclopropyl-5-indolyl)methylamino-3''-methoxycyclohexyl)-1'-methylvinyl]-23,25-dimethoxy-13,19,21,27-tetramethyl-11,28-dioxa-4-azatricyclo[22.3.1.0^{4,9}]octacos-18-ene-2,3,10,16-tetraone;

17-Ethyl-1,14-dihydroxy-12-[2'-(4''-(1-N-cyclopropyl-5-indolyl)methylamino-3''-hydroxycyclohexyl)-1'-methylvinyl]-23,25-dimethoxy-13,19,21,27-tetramethyl-11,28-dioxa-4-azatricyclo[22.3.1.0^{4,9}]-octacos-18-ene-2,3,10,16-tetraone;

17-Allyl-1,14-dihydroxy-12-[2'-(4''-(1-N-cyclopropyl-5-indolyl)methylamino-3''-methoxycyclohexyl)-1'-methylvinyl]-23,25-dimethoxy-13,19,21,27-tetramethyl-11,28-dioxa-4-azatricyclo[22.3.1.0^{4,9}]octacos-18-ene-2,3,10,16-tetraone;

17-Allyl-1,14-dihydroxy-12-[2'-(4''-(1-N-cyclopropyl-5-indolyl)methylamino-3''-hydroxycyclohexyl)-1'-methylvinyl]-23,25-dimethoxy-13,19,21,27-tetramethyl-11,28-dioxa-4-azatricyclo[22.3.1.0^{4,9}]octacos-18-ene-2,3,10,16-tetraone;

17-Ethyl-1,14-dihydroxy-12-[2'-(4''-(1-N-cyclopropyl-5-indolyl)methylamino-3''-ethoxycyclohexyl)-1'-methylvinyl]-23,25-dimethoxy-13,19,21,27-tetramethyl-11,28-dioxa-4-azatricyclo[22.3.1.0^{4,9}]octacos-18-ene-2,3,10,16-tetraone;

17-Allyl-1,14-dihydroxy-12-[2'-(4''-(1-N-cyclopropyl-5-indolyl)methylamino-3''-ethoxycyclohexyl)-1'-methylvinyl]-23,25-dimethoxy-13,19,21,27-tetramethyl-11,28-dioxa-4-azatricyclo[22.3.1.0^{4,9}]octacos-18-ene-2,3,10,16-tetraone;

17-Ethyl-1-hydroxy-12-[2'-(4''-(1-N-cyclopropyl-5-indolyl)methylamino-3''-methoxycyclohexyl)-1'-methylvinyl]-23,25-dimethoxy-13,19,21,27-tetramethyl-11,28-dioxa-4-azatricyclo[22.3.1.0^{4,9}]octacos-18-ene-2,3,10,16-tetraone;

17-Allyl-1-hydroxy-12-[2'-(4''-(1-N-cyclopropyl-5-indolyl)methylamino-3''-methoxycyclohexyl)-1'-methylvinyl]-23,25-dimethoxy-13,19,21,27-tetramethyl-11,28-dioxa-4-azatricyclo[22.3.1.0^{4,9}]octacos-18-ene-2,3,10,16-tetraone;

and pharmaceutically acceptable salts thereof.

B. Preparation of Compounds Within the Scope of the Present Invention

The starting materials for the preparation of the compounds of this invention are represented by Formula II:

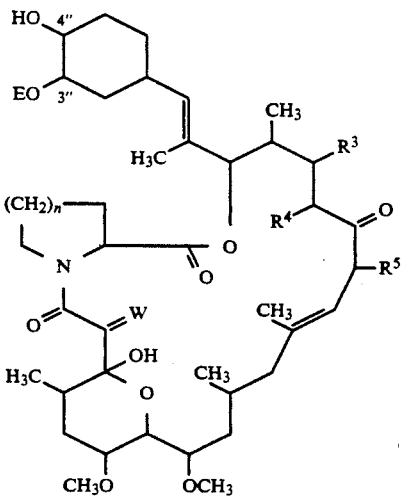

wherein:
E is hydrogen or methyl;
W is O or (H, OH);
$R^3$ is hydrogen, hydroxy, or $C_{1-6}$ alkoxy;
$R^4$ is hydrogen, or $R^3$ and $R^4$ taken together form a double bond;
$R^5$ is methyl, ethyl, propyl or allyl; and
n is 1 or 2.

The production and characterization of compounds of Formula II is well known in the literature (see U.S. Pat. No. 4,894,366 issued Jan. 16, 1990; U.S. Pat. No. 4,929,611 issued May 29, 1990; U.S. Pat. No. 3,244,592 issued Apr. 15, 1966; EPO Publication No. 0,323,042; EPO Publication No. 0,356,399; PBJ Disclosure 63-17884; J. Am. Chem. Soc., 1987, 109, 5031; and J. Antibiotics, 1987, 40, 1249). Both biological fermentation and synthetic processes may be found. A synthetic route to compounds of Formula II can involve modifications of a route described in J. Am. Chem. Soc., 1989, 111, 1157.

Biological fermentation followed by synthetic modification is presently favored in the art as the method to produce compounds of Formula II. Organisms belonging to the genus Streptomyces such as *Streptomyces tsukubaensis*, No. 9993 placed in an aqueous nutrient medium will produce desired compounds in isolable amounts. The nutrient medium contains sources of assimilable carbon and nitrogen, preferably under aerobic conditions. Produced in fermentation are four compounds of Formula II, (A) where E is methyl, W is O, $R^3$ is hydroxyl, $R^4$ is hydrogen, $R^5$ is allyl and n is 2; (B) where E is methyl, W is O, $R^3$ is hydroxyl, $R^4$ is hydrogen, $R^5$ is ethyl and n is 2; (C) where E is methyl, W is O, $R^3$ is hydroxyl, $R^4$ is hydrogen, $R^5$ is methyl and n is 2; and (D) where E is methyl W is O, $R^3$ is hydroxyl, $R^4$ is hydrogen, $R^5$ is allyl and n is 1.

A lyophilized sample of the isolated *Streptomyces tsukubaensis*, No. 9993 was deposited with the Fermentation Research Institute, Agency of Industrial Science and Technology (No. 1-3, Higashi 1-chome, Yatabemachi Tsukuba-gun, Ibaraki Prefecture, Japan) under the deposit number of FERM P-7886 (deposit date: Oct. 5th, 1984), and then converted to Budapest Treaty route of the same depository on Oct. 19, 1985 under the new deposit number of FERM BP-927.

Using the four compounds produced in fermentation above, the remaining compounds of Formula II may be easily produced. The allyl of $R^5$ may be conveniently reduced to propyl by well known methods, for example as described in U.S. Pat. No. 4,894,366. The hydroxy of $R^3$ may be protected by well known methods, for example as disclosed in EPO Publication No. 0,323,042. Likewise, the hydroxy at C-4'' may also be protected. In addition, the hydroxy of $R^3$ may be reduced to a hydrogen or eliminated to form a double bond with $R^4$ (by methods disclosed in U.S. Pat. No. 4,894,366, EPO Publication No. 0,323,042 or EPO Publication No. 0,413,532). The carbonyl of W may be reduced to the alcohol by methods disclosed in EPO Publication No. 0,323,042 or by methods discloses in EPO Publication No. 0,445,975.

The methyl of E as produced may be replaced with hydrogen or demethylated and subsequently protected as desired, if necessary. This demethylation of compounds wherein E is methyl may be carried out in a fermentation reaction using the compounds of Formula II as a feedstock. For instance, compound A named under Formula II above may be demethylated at Q above by using the microorganism Actinomycetales ATCC No. 53771 (described in U.S. Pat. No. 4,981,792, issued Jan. 1, 1991. Similarly, compound B named under Formula II above may be demethylated at Q above using the microorganism Actinoplanacete sp. ATCC No. 53771 (described in EPO Publication No. 0,349,061). In addition the compound of Formula II wherein E is H, W is O, $R^3$ is hydroxy, $R^4$ is hydrogen, $R^5$ is ethyl and n is 2 may be produced directly by fermentation using the mutant microorganism *Streptomyces hygroscopicus* sup. *ascomyceticus*, No. 53855 (being a blocked mutant of *Streptomyces hygroscopicus* sup. *ascomyceticus*, No. 14891) (as described in EPO Publication 0,388,152). Similarly, the compound of Formula II wherein E is hydrogen, W is O, $R^3$ is hydroxy, $R^4$ is hydrogen, $R^5$ is methyl and n is 2 may be produced directly by fermentation using the mutant microorganism *Streptomyces hygroscopicus* sup. *ascomyceticus*, No. 53855 (being a blocked mutant of *Streptomyces hygroscopicus* sup. *ascomyceticus*, No. 14891) (as described in EPO Publication 0,388,153). Also, the compound of Formula II wherein E is hydrogen, $R^3$ is hydroxy, $R^4$ is hydrogen, $R^5$ is allyl, W is O and n is 2 and the compound of Formula II wherein the C-3'' position is oxo (keto), $R^3$ is hydroxy, $R^4$ is hydrogen, $R^5$ is allyl, W is O and n is 2 may be produced directly by fermentation using the microorganism *Streptomyces tsukubaensis*, No. 9993 (described in EPO Publication No. 0,353,678). The hydroxy of C-3'' may be protected by methods similar to those known for the protection of the hydroxy's of $R^3$ and/or C-4'', for example as disclosed in U.S. Pat. No. 4,894,366.

Suitable protecting groups for hydroxyl include those groups well known in the art which are: trisubstituted silyl such as tri(lower)-alkylsilyl (e.g. trimethylsily, triethylsilyl, tri-i-propylsilyl, t-butyldimethylsilyl, t-butyldiphenylsilyl, etc.), and the like, in which the most preferred one may be tert-butyl-dimethylsilyl, tri-isopropylsilyl and tert-butyl-diphenylsilyl.

Compounds A, B, C and D of Formula II, organisms to produce the same, conditions of fermentation, separation techniques, and chemical modification of the products are fully described in U.S. Pat. No. 4,894,366, issued Jan. 16, 1990 and U.S. Pat. No. 4,929,611, issued May 29, 1990.

The compounds of the present invention which are represented by Formula I are prepared by the methods shown in the following Reaction Schemes wherein $R^1$, $R^2$, $R^3$, $R^4$, $R^5$, $R^{10}$, W, and n are as defined above unless otherwise indicated. It will be readily apparent to one of ordinary skill in the art reviewing the synthetic route depicted below that other compounds within Formula I can be synthesized by substitution of appropriate reactants and agents in the synthesis shown below.

REACTION SCHEME A

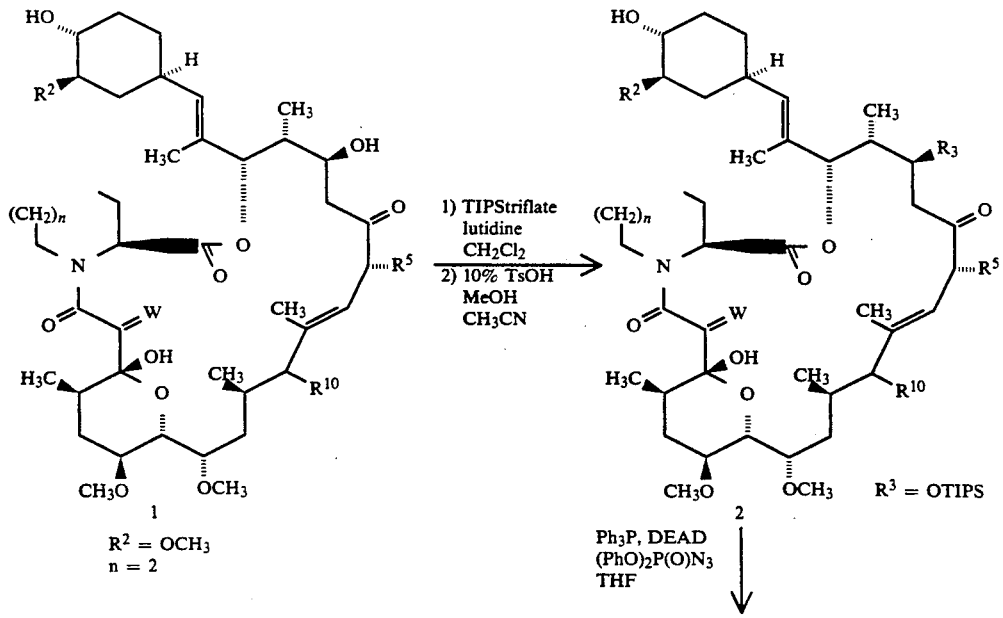

-continued
REACTION SCHEME A
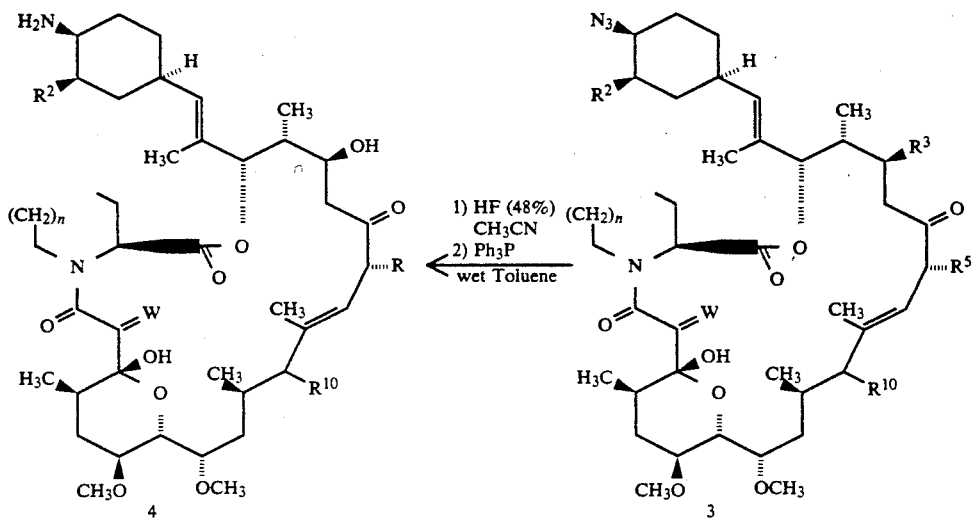
REACTION SCHEME B
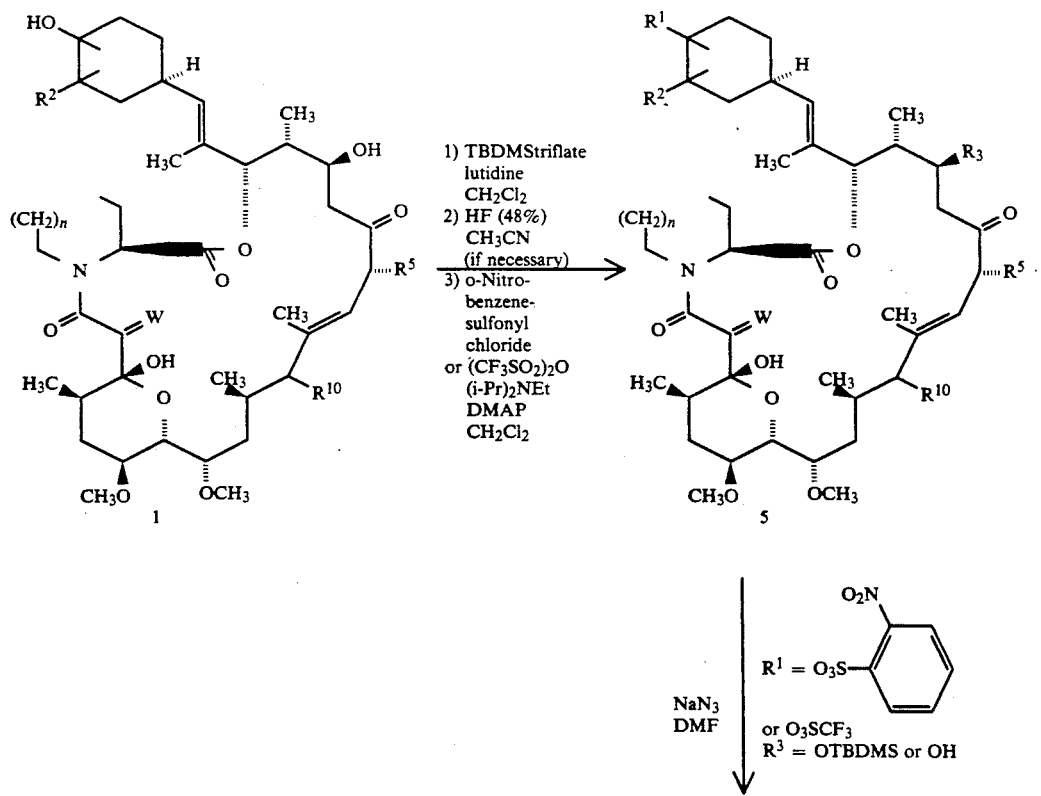

REACTION SCHEME B
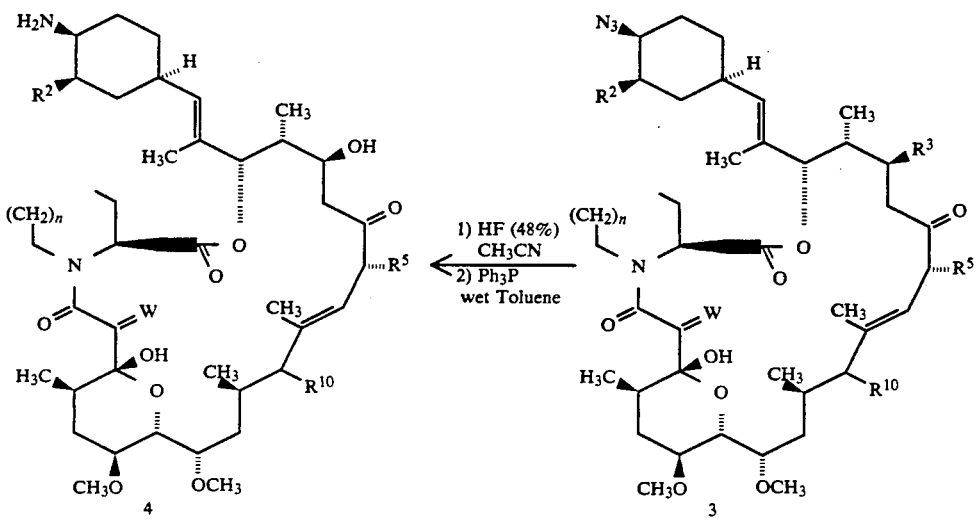
REACTION SCHEME C
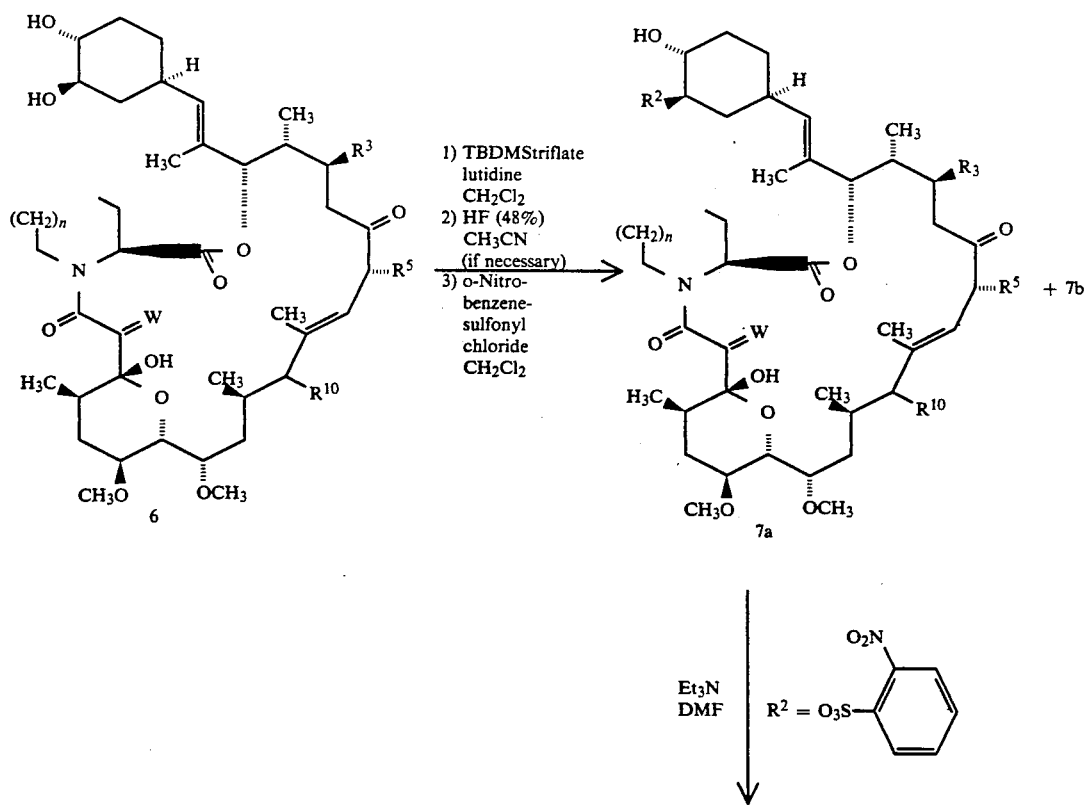

5,208,241
-continued
REACTION SCHEME C
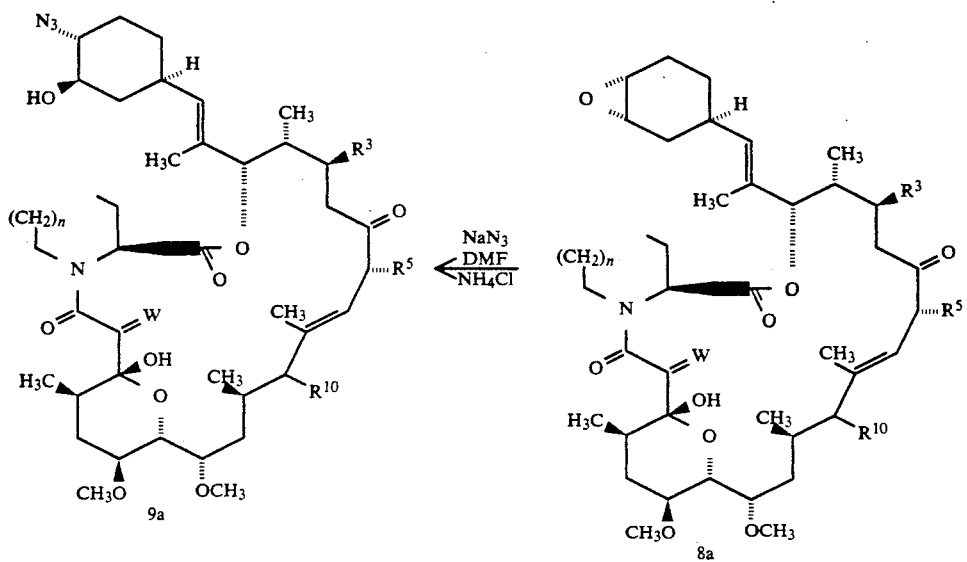
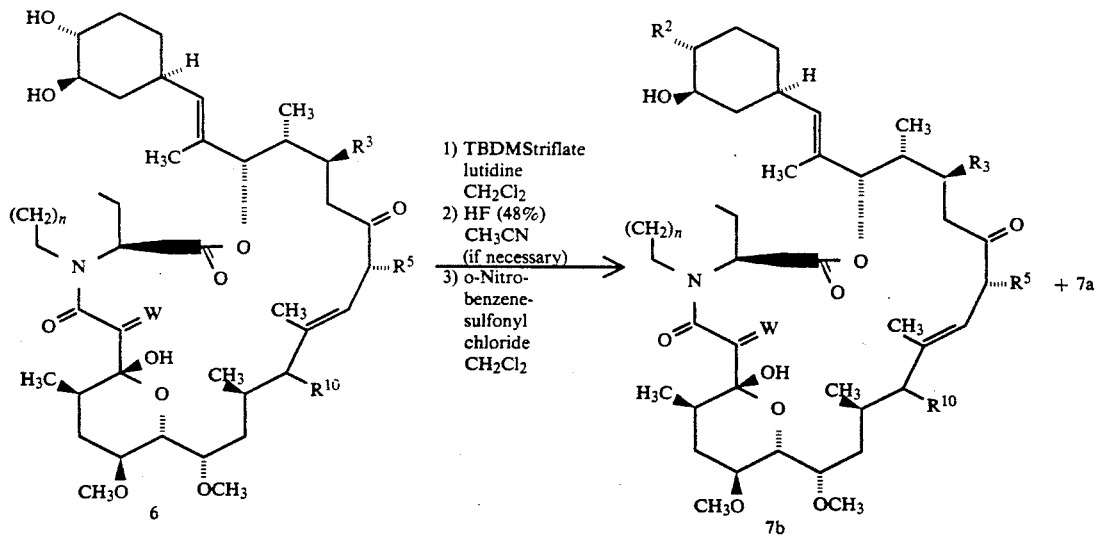
$R^3 =$ OTBDMS, OH, or H -continued
REACTION SCHEME C
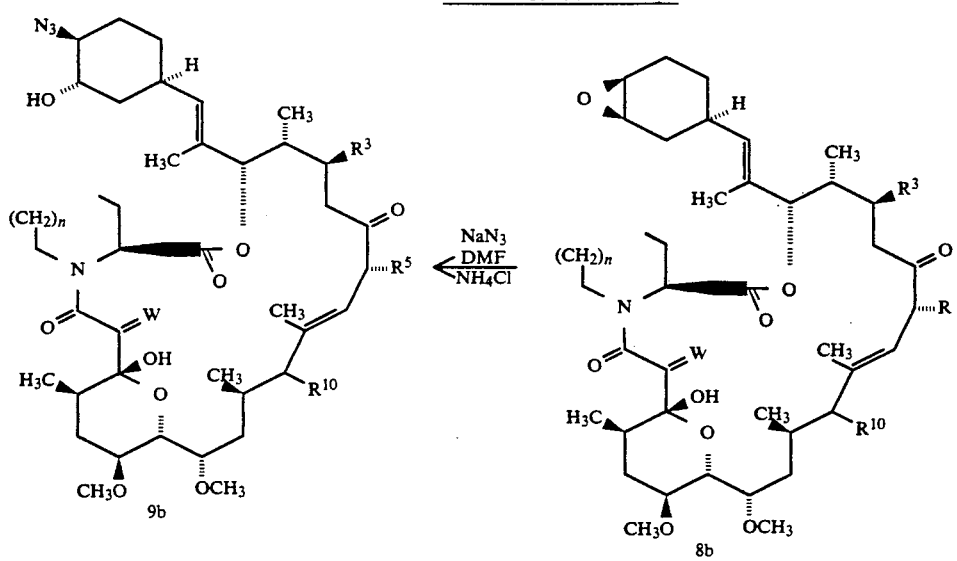
REACTION SCHEME D
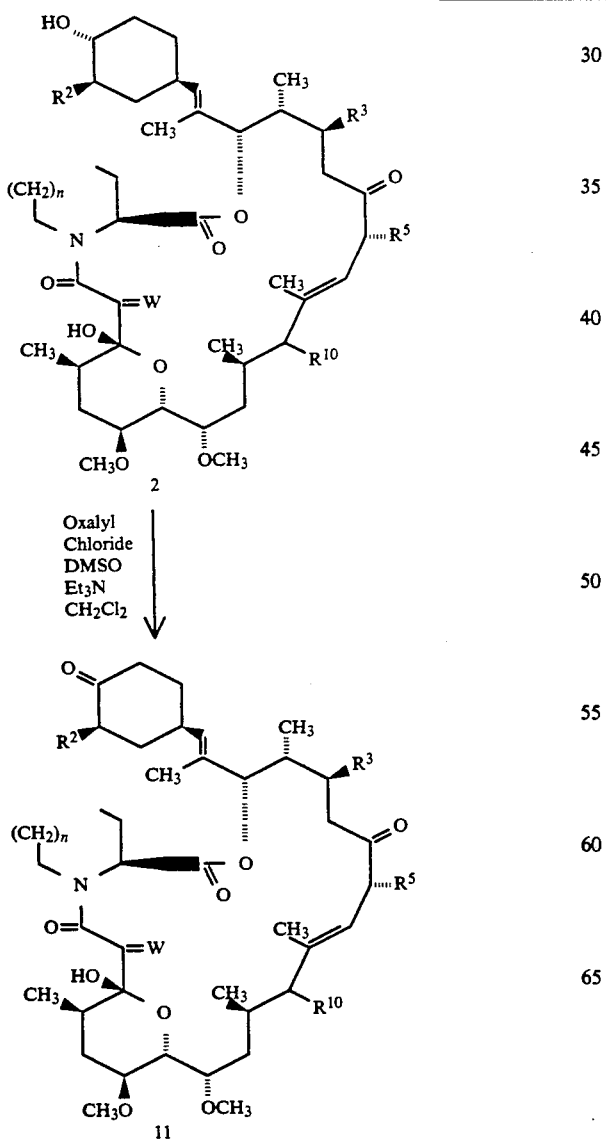

-continued
REACTION SCHEME D
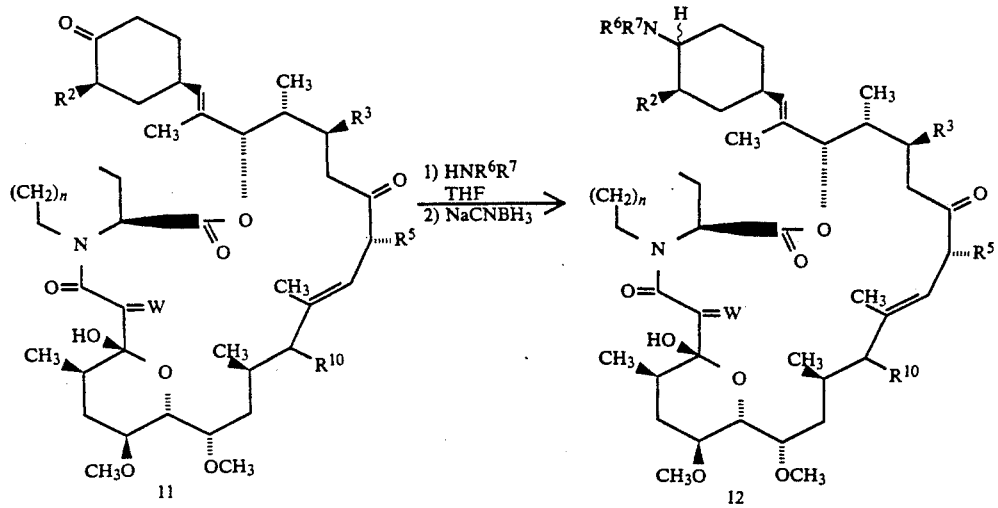
REACTION SCHEME E
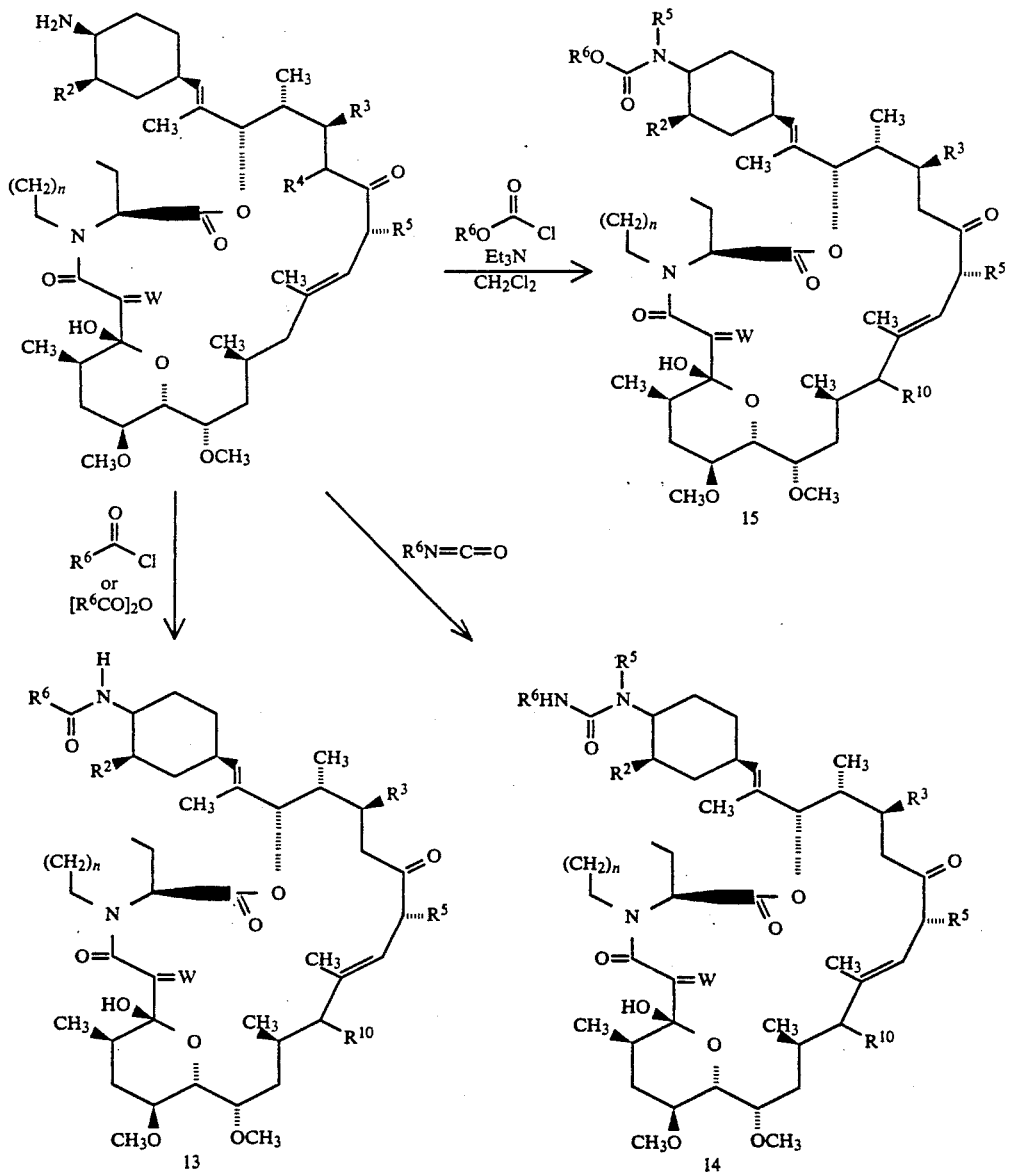

REACTION SCHEME F
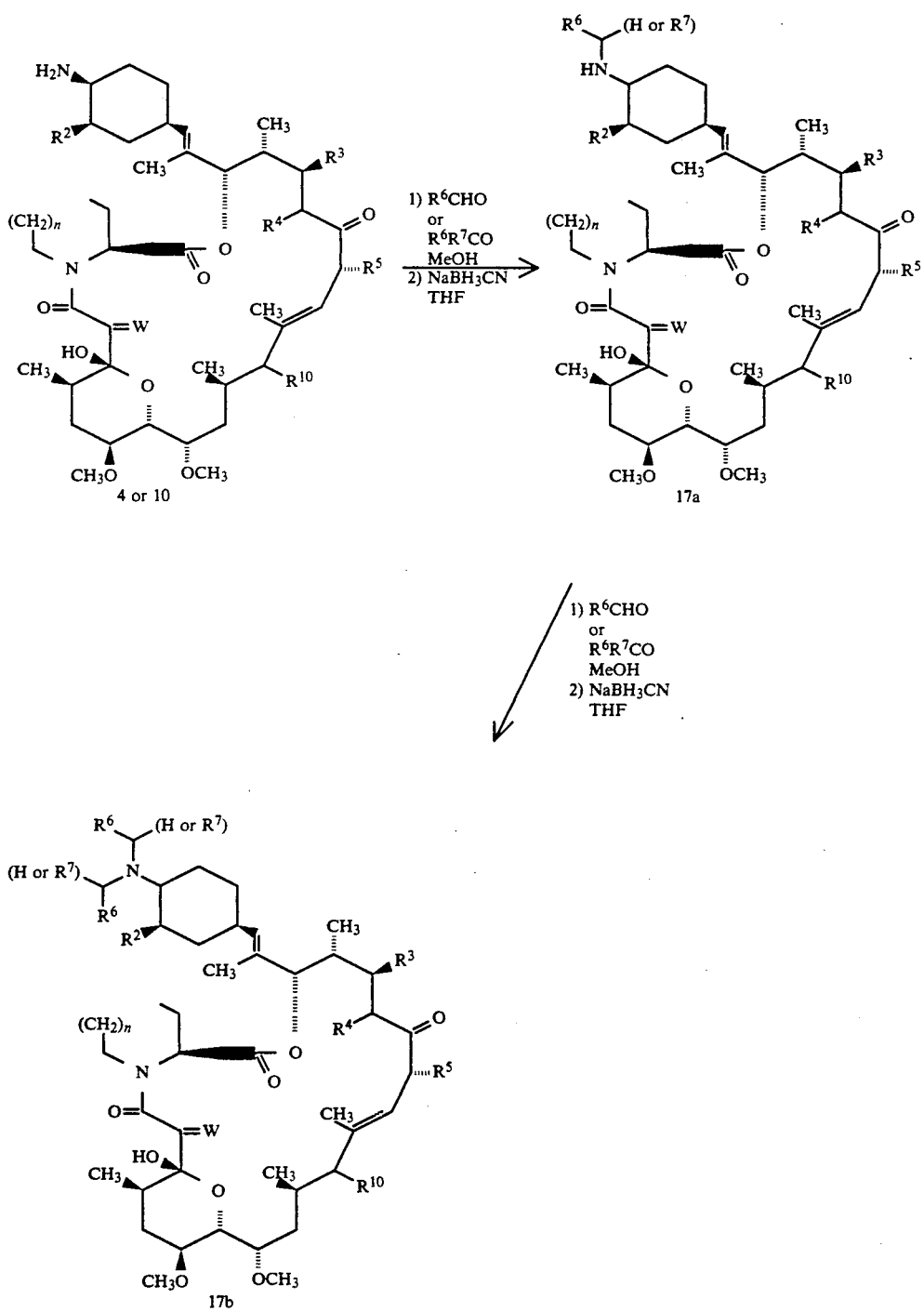

REACTION SCHEME G
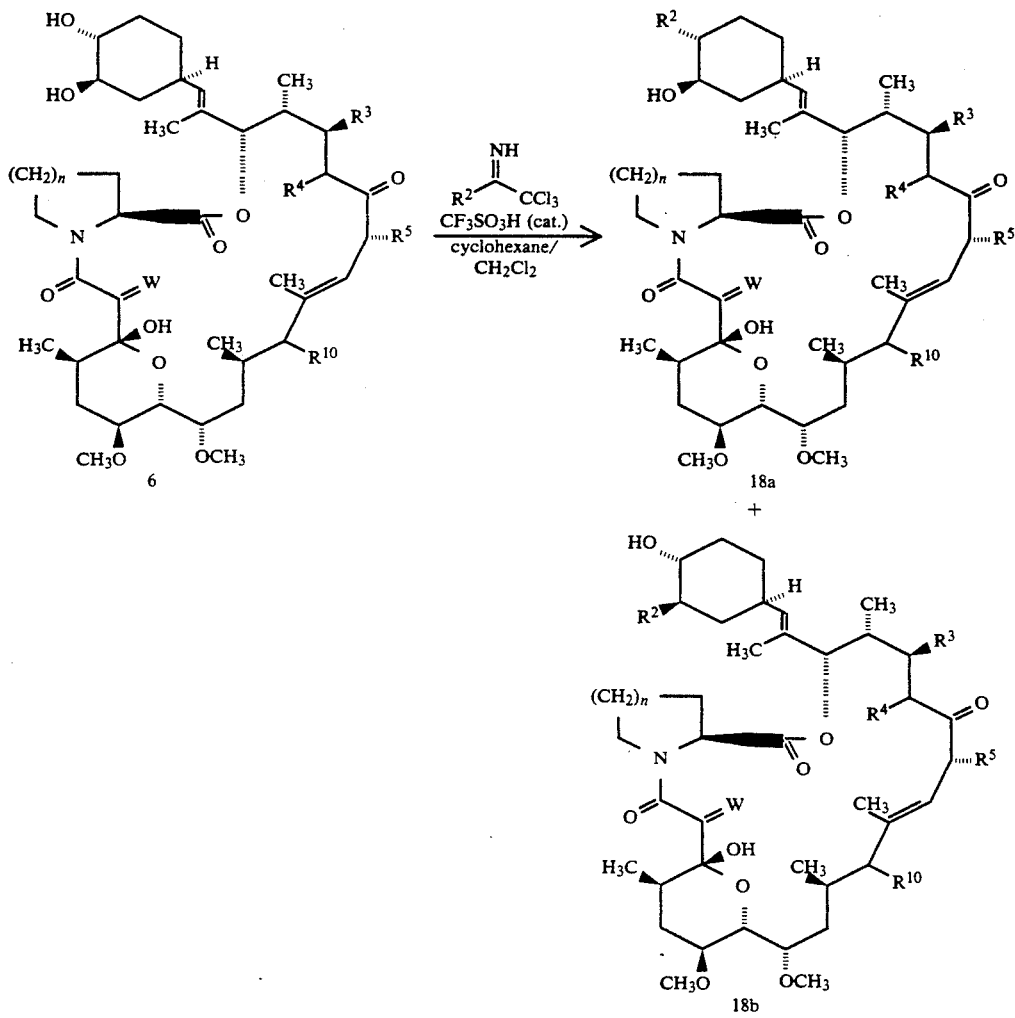
REACTION SCHEME H
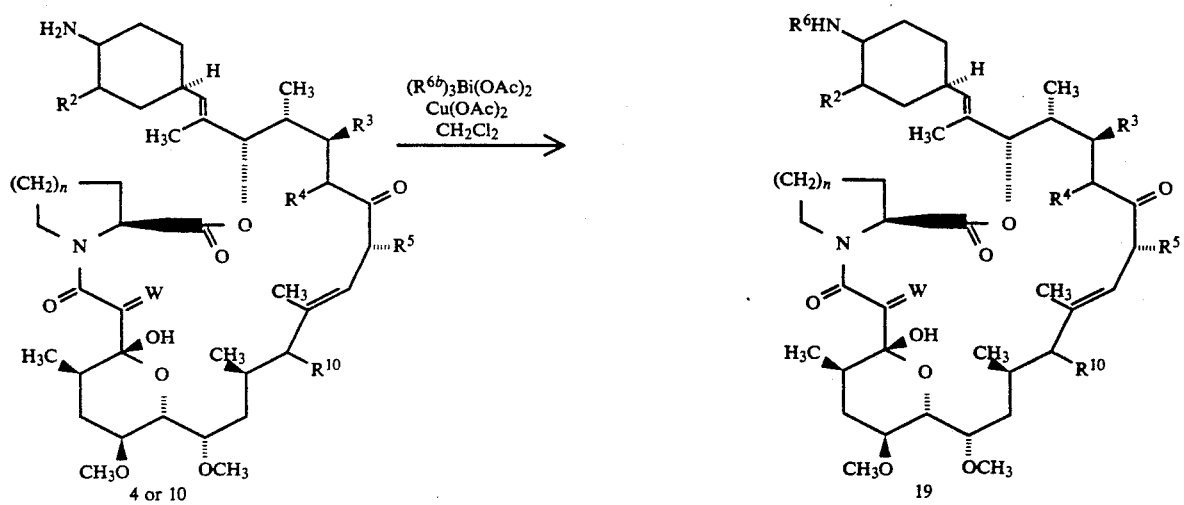

REACTION SCHEME I
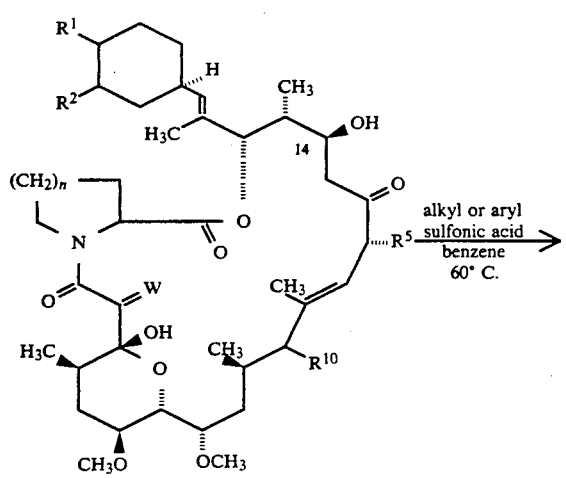
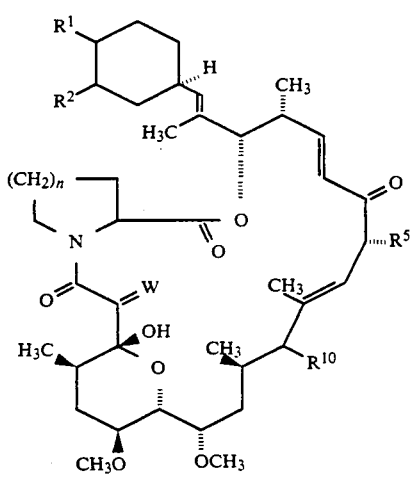
REACTION SCHEME J
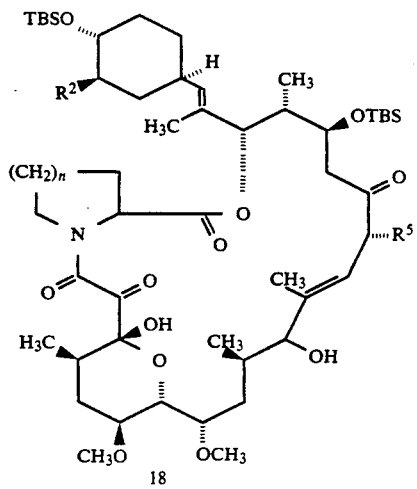
REACTION SCHEME J
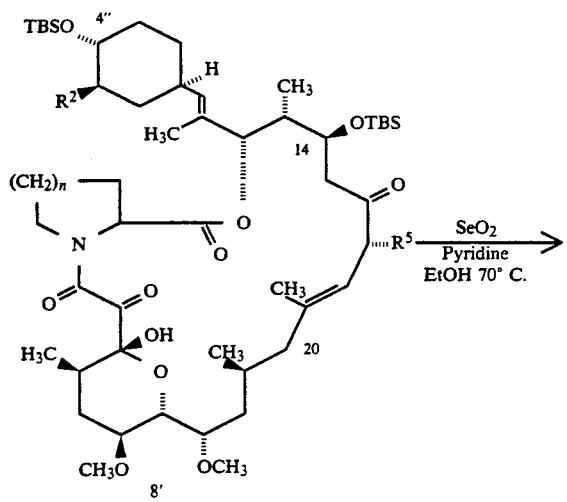
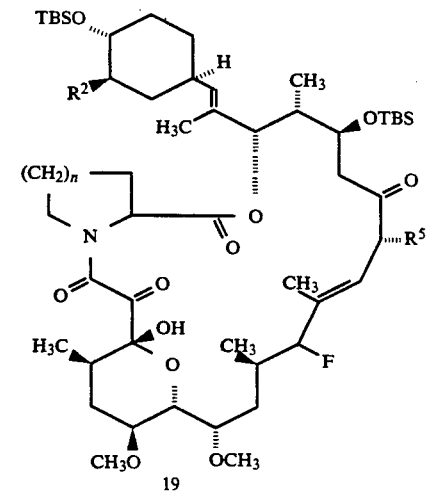

REACTION SCHEME J

-continued

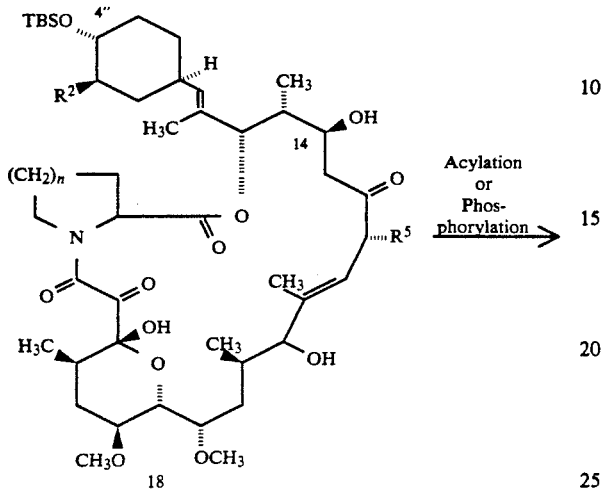

18

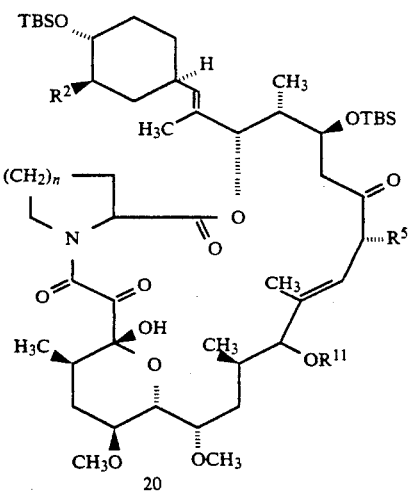

20

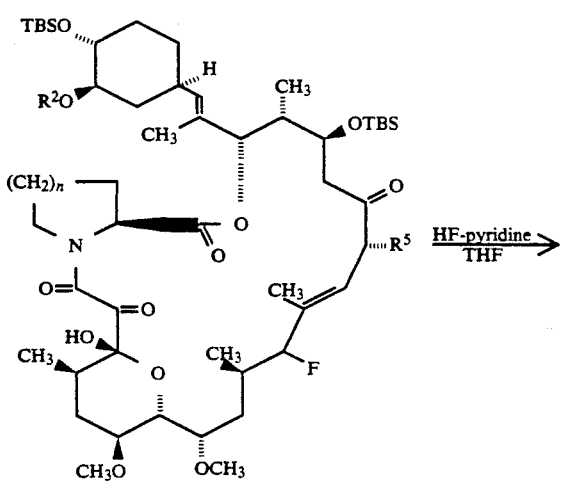

-continued
REACTION SCHEME J

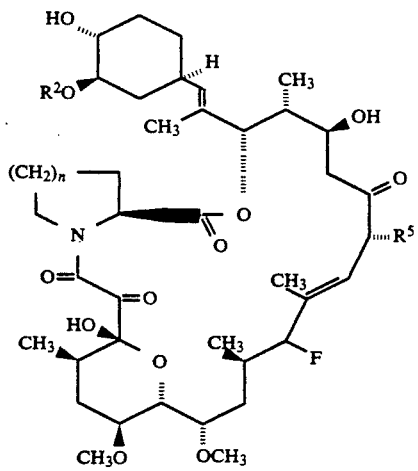

Reaction Scheme A

Protection of the C-14 hydroxyl group may be accomplished by methods known in the prior art for compounds of Formula II such as by treatment with: 2,6-lutidine and triisopropylsilyl trifluoromethanesulfonate in a solution of methylene chloride; 2,6-lutidine; t-butyldimethylsilyl trifluoromethanesulfonate in a solution of methylene chloride; pyridine and acetic anhydride in a solution of methylene chloride; pyridine and benzoyl chloride in a solution of dichloromethane; pyridine and p-nitrobenzoyl chloride in a solution of dichloromethane; imidazole and t-butyldiphenylsilyl chloride in a solution of methylene chloride; and the like. For example, as shown in Reaction Scheme A, the C-4″,14-dihydroxy-C-3″-methoxy macrolide 1 may be protected at C-14 as the tri-isopropylsilyl ether (TIPS) by treatment with tri-isopropylsilyltrifluoromethanesulfonate in methylene chloride to give the C-4″,14-di-O-TIPS macrolide. Subsequent treatment with toluenesulfonic acid in methanol results in selective removal of the C-4″ silyl ether to give the $C_{14}$-O-TIPS macrolide 2. $C_{14}$-OTIPS protected macrolide 2 is reacted with diphenylphosphorylazide in the presence of triphenyl phosphine and diethyl azodicarboxylate to introduce the C-4″-β-azide 3. The C-14 protecting group is removed and the azide is reduced with triphenylphosphine/water to give epi or β-amino analog 4. This route may also be used to prepare C-3″(α) amino macrolides.

Reaction Scheme B

An alternate route to C-4″ epi-amino substituted compounds is shown in Reaction Scheme B. Macrolide 1 can be protected at C-14, if necessary, then reacted with o-nitrobenzenesulfonyl chloride or trifluoromethanesulfonylanhydride in the presence of an amine base such as triethylamine or diisopropylethylamine to give the C-4″ o-nitrobenzenesulfonyl or trifluoromethanesulfonyl derivative 5. Reaction of 5 with sodium or lithium azide gives azide derivative 3. The protecting group of 3 is removed, if necessary, by treatment with hydrogen fluoride and, the azide is reduced with triphenyphosphine/water or a trialkyl phosphine/water to give the amino derivative 4. Azides can also be reduced with other reagents known in the art, such as with hydrogen sulfide, propane-1,3-dithiol, or thioacetic acid or by catalytic hydrogenation over a suitable catalyst. This route may also be used to prepare C-3" amino macrolides.

Reaction Scheme C

As shown in Reaction Scheme C, C-4" amino derivatives containing the natural (α) stereochemistry can be obtained via an epoxide intermediate. Reaction of β-C3"-α-C4" dihydroxy macrolide 6 (wherein $R^3$ is hydrogen or protected hydroxy) with o-nitrobenzenesulfonyl chloride gives C-4" and C-3" isomers 7a and 7b which can be separated by chromatography. Treatment of each isomer with a tertiary amine base such as triethylamine in DMF gives two isomeric epoxides 8a and 8b. Reaction of beta-epoxide 8a with sodium or lithium azide in DMF or THF, respectively, gives C-4"-alpha-azido-C-3"-beta-hydroxy macrolide 9a. The C-3"-hydroxyl group of 9a may be alkylated or protected, prior to reduction of the azide group (by the methods of Reaction Scheme B) to give the corresponding amine derivative 10a. Similarly, reaction of the alpha-epoxide 8b with sodium or lithium azide in DMF or THF, respectively, gives the C-4"-beta-azido-C-3"-alpha-hydroxy macrolide 9b. The C-3"-hydroxy group of 9b may be alkylated or protected, prior to reduction of the azide group (by the methods of Reaction Scheme B) to give the corresponding amine derivative.

Reaction Scheme D

An amino substituent may also be introduced at C-4" by reductive amination of a keto-substituted macrolide as shown in Reaction Scheme D. The C-4" ketone 11 can be prepared by oxidation of a suitably protected hydroxy-macrolide 2 by procedures commonly known to practitioners of the art. An efficient, mild reaction is then Swern reaction wherein one reacts an alcohol with oxalyl chloride in a solution of DMSO and methylene chloride and an amine base such as triethylamine. A variety of compounds may be prepared from ketone 11 as illustrated. Ketone 11 may be reacted with a primary or secondary amine, $HNR^6R^7$ (wherein $R^6$ and/or $R^7$ are as defined and contain(s) a heteroaryl group) in an organic solvent such as tetrahydrofuran to give an imine intermediate which is reduced in situ with a hydride reducing agent, such as sodium cyanoborohydride, to give amino macrolide 12 as an epimeric mixture at C-4". The procedures described in Reaction Scheme D are readily applicable to the preparation of compounds bearing analogous functionality at C-3".

Reaction Scheme E

Compounds bearing a C-4" or a C-3" amino substituent may be further modified by methods exemplified in Reaction Scheme E. These methods include, but are not limited to such methods as: acylation with an appropriate acyl halide or acid anhydride in the presence of an amine base to give the corresponding amide 13; coupling with an appropriate carboxylic acid and coupling reagents such as dicyclohexylcarbodiimide (DCC)/hydroxybenzotriazole (HOBT), or BOP chloride, to give the corresponding amide 13; reaction with an isocyanate to give the urea derivative 14, treatment with a chloroformate to give the corresponding carbamate 15 or alkylation with an appropriate alkyl halide to give the corresponding secondary, tertiary or quaternary alkyl amine.

Reaction Scheme F

A C-4" or C-3" amino derivative may produced by reductive amination of an amino-substituted macrolide as shown in Reaction Scheme F. Amines 4 or 10 may be reacted with an aldehyde or ketone containing a heteroaryl group in an organic solvent such as tetrahydrofuran or an alcohol such as methanol or ethanol to give an intermediate imine which is reduced in situ with a hydride reducing agent, such as sodium cyanoborohydride, to give macrolide 17a. The procedures may be repeated to give the tertiary amine 17b. The procedures described in Reaction Scheme F are readily applicable to the preparation of compounds bearing analagous functionality at C-3".

Reaction Scheme G

As shown in Reaction Scheme G, a solution of the 3",4"-dihydroxy macrolide 6 in an inert organic solvent such as methylene chloride, chloroform, hexanes or the like or mixtures thereof is treated with a trichloroacetimidate (prepared by the reaction of an appropriate sodium alkoxide with trichloracetonitrile, such as described by Wessel, H. P., Iversen, T., Bundle, D.R., *J. Chem., Soc.*, Perkins Trans. I, 1985, 2247) in the presence of a mild acid catalyst such as trifluoromethanesulfonic acid, p-toluenesulfonic acid, methanesulfonic acid, or mixtures thereof at a temperature of 20°–50° C., for a period of one hour to seven days, preferably 6 hours, to give a mixture of the 3"-O-alkyl- or 3"-O-alkenyl-4"-hydroxy macrolide 18a and the 3"-hydroxy-4"-O-alkyl or -alkenyl macrolide 18b. The free hydroxyl group at C-3" or C-4" may be converted to an amino-containing functionality by the procedures described in Reaction Schemes A thru F.

Reaction Scheme H

As shown in Reaction Scheme H, a solution of a 4"-amino-macrolide 4 or 10 in an inert organic solvent such as methylene chloride, benzene, toluene, chloroform, or the like or mixtures thereof is treated with a triheteroarylbismuth diacetate reagent (wherein $R^{6b}$ is O-heteroaryl) (prepared immediately prior to use by the addition of acetic acid to a suspension of a triheteroarylbismuth carbonate in an inert organic solvent such as methylene chloride, chloroform or the like or mixture thereof) in the presence of a catalytic amount of copper-(II) acetate at a temperature of 20°–50° C., preferably room temperature, for a period of one hour to seven days, preferably one day, to give the 4"-N-heteroarylamino macrolides 19. Alternatively, the triheteroarylbismuth(V) reagent can be prepared by treatment of a triheteroarylbismuthine with a suitable oxidant such as peracetic acid, iodobenzene diacetate, bis(trifluoroacetoxy) iodobenzene and the like in an inert solvent such as methylene chloride, chloroform, benzene, toluene and the like. The triheteroarylbismuth(V) reagent can be used without purification or can be purified by silica gel chromatography. Triheteroarylbismuthines may be prepared by the reaction of an appropriate heteroaryl Grignard reagent or a lithiated heteroaryl species with bismuth trichloride in an inert organic solvent such as tetrahydrofuran, diethyl ether, or 1,4-dioxane, or mixtures thereof, at or near room temperature for a period of 1 to 48 hours. General procedures for the preparation and use of triheteroaryl bismuth reagents may be found in Barton, D.H.E., et al., *Pure and Appl. Chem.* 59, 937–946 (1987); Barton, D.H.E., et al, *J. Chem. Soc. Chem. Commun.*, 65 (1986); Finet, J-P, Chem. Rev., 89, 1487-1501 (1989) and references cited therein.

Reaction Scheme I

For macrolides containing a 14-hydroxyl group ($R^3$=OH), the hydroxyl may be eliminated by treatment with p-toluenesulfonic acid, benzenesulfonic acid or methanesulfonic acid in an inert organic solvent such as benzene, or toluene at from 40° C. to 60° C., for about 0.5 to 6 hours, or a sufficient period of time to eliminate the 14-hydroxy group. Neutralization with an aqueous solution of a weak base such as aqueous saturated sodium bicarbonate gives the 14,15-dehydro macrolide. The 14-hydroxy group may also be eliminated by activation followed by basic elimination, as described in U.S. Pat. No. 4,894,366.

Reaction Scheme J

A hydroxyl or fluoro group may be introduced at C-20 essentially by the procedures of Reaction Scheme J. As shown in Reaction Scheme R the 4",14-dihydroxy macrolide (or the 14-deoxymacrolide) is protected as the di(t-butyldimethylsilyl ether) by treatment with t-butyldimethylsilyl triflate in an inert organic solvent such as methylene chloride, chloroform or the like in the presence of a non-nucleophillic base such as 2,6-lutidine. The diprotected macrolide is oxidized at C-20 as further shown in Reaction Scheme R by treatment with selenium dioxide in an alcoholic solvent such as ethanol in the presence of pyridine at solvent reflux temperature to give the 20-hydroxy macrolide. The 20-hydroxy macrolide may be further derivatized at C-20 by alkylation, acylation or phosphorylation to give ether, ester or phosphate derivatives by procedures well known to the practitioner of the art. As further illustrated, treatment of the 20-hydroxy 4",14-di-OTBS macrolide with diethylaminosulfur trifluoride in an inert organic solvent such as methylene chloride, chloroform or the like at a temperature of about 0° C. to −90° C., preferably about −78° C., gives the 20-fluoro 4", 14-di-OTBS macrolide. Removal of the silyl ether protecting groups by treatment with hydrogen fluoride-pyridine complex in tetrahydrofuran gives the 20-fluoro 4",14-dihydroxy macrolide which may be further derivatized by any of the methods previously described. Reaction Scheme J may also be performed on the 3", 4", 14-trihydroxy macrolide to give the 20-fluoro 3", 4", 14-trihydroxy macrolide. The procedures of Reaction Scheme J may be conducted prior to, concurrent with, or subsequent to the procedures of Reaction Schemes A-I.

In any of the aforementioned Reaction Schemes, the macrolide (wherein $R^1$ and/or $R^2$ contains an alkenyl, substituted alkenyl, alkynyl or substituted alkynyl and wherein $R^3$ is hydroxy or $C_{1-6}$ alkoxy, $R^4$ is hydrogen, or $R^3$ and $R^4$ taken together form a double bond) can be reduced with tri-n-butyltin hydride in the presence of tetrakis(triphenylphosphine) palladium (O) catalyst and acetic acid in an organic solvent such as toluene or tetrahydrofuran at or near room temperature for about 2 to 10 hours to give the reduced macrolide.

By changing the sequence of synthetic steps, all possible variations of substitution can be achieved.

The object compounds of Formula I obtained according to the reactions as explained above can be isolated and purified in a conventional manner, for example, extraction, precipitation, fractional crystallization, recrystallization, chromatography, and the like.

In the compounds of Formula I, $R^1$ may be substituted at C-4" or C-3", or both C-3" and C-4" (wherein $R^2$ is independently selected form the definitions of $R^1$), but it is preferred that $R^1$ is substituted at C-4".

It is to be noted that in the aforementioned reactions and the post-treatment of the reaction mixture therein, the stereo isomer(s) of starting and object compounds due to asymmetric carbon atom(s) or double bond(s) of the object compounds of Formula I may occasionally be transformed into the other stereo isomer(s), and such cases are also included within the scope of the present invention.

In the present invention, compounds with asymmetric centers may occur as racemates, racemic mixtures and as individual diastereomers, with all isomeric forms of the compounds being included in the present invention. These may be prepared by methods such as those disclosed in publications which describe synthetic routes to fragments of the macrolide FR-900506 and the total synthesis of the macrolide FR-900506 itself (see for example, *J. Am. Chem. Soc.* 1989, 111, 1157; *J. Am. Chem. Soc.* 1990, 112, 2998; *J. Org. Chem.* 1990, 55, 2786; *J. Am. Chem. Soc.* 1990, 112, 5583. *Tetrahedron Lett.* 1988, 29, 277; *Tetrahedron Lett.* 1988, 29, 281; *Tetrahedron Lett.* 1988, 29, 3895; *J. Org. Chem.* 1988, 53, 4643; *Tetrahedron Lett.* 1988, 29, 4245; *Tetrahedron Lett.* 1988, 29, 4481; *J. Org. Chem.* 1989, 54, 9; *J. Org. Chem.* 1989, 54, 11; *J. Org. Che.* 1989, 54, 12; *J. Org. Chem.* 1989, 54, 15; *J. Org. Chem.* 1989, 54, 17; *Tetrahedron Lett.* 1989, 30, 919; *Tetrahedron Lett.* 1989, 30, 1037; *J. Org. Chem.* 1989, 54, 2785; *J. Org. Chem.* 1989, 54, 4267; *Tetrahedron Lett.* 1989, 30, 5235; *Tetrahedron Lett.* 1989, 30, 6611; *Tetrahedron Lett.* 1989, 30, 6963; *Synlett* 1990, 38; *J. Org. Chem.* 1990, 55, 2284; *J. Org. Chem.* 1990, 55, 2771; *J. Org. Chem.* 1990, 55, 2776; *Tetrahedron Lett.* 1990, 31, 1439; *Tetrahedron Lett.* 1990, 31, 1443; *Tetrahedron Lett.* 1990, 31, 3007; *Tetrahedron Lett.* 1990, 31, 283, 3287). Also, the basic nitrogen-containing groups may be quaternized.

The compounds of the present invention are capable of forming salts with various inorganic and organic acids and bases and such salts are also within the scope of this invention. Examples of such acid addition salts (which are negative counterions defined herein as M−) include acetate, adipate, benzoate, benzenesulfonate, bisulfate, butyrate, citrate, camphorate, camphorsulfonate, ethanesulfonate, fumarate, hemisulfate, heptanoate, hexanoate, hydrochloride, hydrobromide, hydroiodide, methanesulfonate, lactate, maleate, methanesulfonate, 2-naphthalenesulfonate, oxalate, pamoate, persulfate, picrate, pivalate, propionate, succinate, tartrate, tosylate, and undecanoate. Base salts (which are positive counterions defined herein as M+) include ammonium salts, alkali metal salts such as sodium, lithium and potassium salts, alkaline earth metal salts such as calcium and magnesium salts, salts with organic bases such as dicyclohexylamine salts, N-methyl-D-glucamine, and salts with amino acids such as arginine, lysine and so forth. Also, the basic nitrogen-containing groups may be quaternized with such agents as: lower alkyl halides, such as methyl, ethyl, propyl, and butyl chloride, bromides and iodides; dialkyl sulfates like dimethyl, diethyl, dibutyl; diamyl sulfates; long chain halides such as decyl, lauryl, myristyl and stearyl chlorides, bromides and iodides; aralkyl halides like benzyl bromide and others. The non-toxic physiologically acceptable salts are preferred, although other salts are also useful, such as in isolating or purifying the product. The salts may be formed by conventional means, such as by reacting the free base form of the product with one or more equivalents of the appropriate acid in a solvent or medium in which the salt is insoluble, or in a solvent such as water which is removed in vacuo or by freeze drying or by exchanging the anions of an existing salt for another anion on a suitable ion exchange resin. Also, the basic nitrogen-containing groups may be quaternized with such agents as: lower alkyl halides, such as methyl, ethyl, propyl, and butyl chloride, bromides and iodides; dialkyl sulfates like dimethyl, diethyl, dibutyl; diamyl sulfates; long chain halides such as decyl, lauryl, myristyl and stearyl chlorides, bromides and iodides; aralkyl halides like benzyl bromide and others.

C. Utility of the Compounds Within the Scope of the Invention

The compounds of Formula I may be employed as immunosuppressants or antimicrobial compounds by methods and in dosages known in the prior art for compounds of Formula II. These compounds possess pharmacological activity such as immunosuppressive activity, antimicrobial activity, and the like, and therefore are useful for the treatment and prevention of the resistance to transplantation or transplantation rejection of organs or tissues such as heart, kidney, liver, duodenum, small-bowel, medulla ossium, skin, pancreatic islet-cell, etc., graft-versus-host diseases by medulla ossium transplantation, autoimmune diseases such as rheumatoid arthritis, systemic lupus erythematosis, Hashimoto's thyroiditis, multiple sclerosis, myasthenia gravis, type I diabetes, uveitis, allergic encephalomyelitis, glomerulonephritis, etc., and infectious diseases caused by pathogenic microorganisms.

The compounds of Formula I are also useful for treating inflammatory and hyperproliferative skin diseases and cutaneous manifestations of immunologically-mediated illnesses such as: psoriasis, atopical dermatitiis, contact dermatitis and further eczematous dermatitises, seborrhoeic dermatitis, Lichen planus, Pemphigus, bullous Pemphigoid, Epidermolysis bullosa, urticaria, angioedemas, vasculitides, erythemas, cutaneous eosinophilias or Alopecia areata. More particularly, the compounds of Formula I are useful in hair revitalizing, such as in the treatment of male pattern alopecia or alopecia senilis, by providing epilation prevention, hair germination, and/or a promotion of hair generation and hair growth.

The compounds of Formula I are further useful for treating reversible obstructive airways disease, including conditions such as asthma, including bronchial asthma, allergic asthma, intrinsic asthma, extrinsic asthma and dust asthma, particularly chronic or inveterate asthma (for example late asthma and airway hyperresponsiveness), bronchitis and the like. The compounds of Formula I may also be useful for treating hepatic injury associated with ischemia.

The compounds of Formula I may also act as antagonists of macrocyclic immunosuppressive compounds, including derivatives of 12-(2'-cyclohexyl-1'-methylvinyl)-13,19,21,27-tetramethyl-11,28-dioxa-4-azatricyclo[22.3.1.0$^{4,9}$]octacos-18-ene, and so be useful in the treatment of immunodepression (such as AIDS, cancer, senile dementia, trauma (including wound healing, surgery and shock), chronic bacterial infection and certain central nervous system disorders), overdosages or toxicity of such immunosuppressive compounds, and as an adjunct to the administration of an antigen in vaccination.

The pharmaceutical compositions of this invention can be used in the form of a pharmaceutical preparation, for example, in solid, semisolid or liquid form, which contains one or more of the compounds of the present invention, as an active ingredient, in admixture with an organic or inorganic carrier or excipient suitable for external, enteral or parenteral applications. The active ingredient may be compounded, for example, with the usual non-toxic, pharmaceutically acceptable carriers for tablets, pellets, capsules, suppositories, solutions, emulsions, suspensions, and any other form suitable for use. The carriers which can be used are water, glucose, lactose, gum acacia, gelatin, mannitol, starch paste, magnesium trisilicate, talc, corn starch, keratin, colloidal silica, potato starch, urea and other carriers suitable for use in manufacturing preparations, in solid, semisolid, or liquid form, and in addition auxiliary, stabilizing, thickening and coloring agents and perfumes may be used. For example, the compounds of Formula I may be utilized with hydroxypropyl methylcellulose essentially as described in U.S. Pat. No. 4,916,138, issued Apr. 10, 1990, or with a surfactant essentially as described in EPO Publication 0,428,169. Oral dosage forms may be prepared essentially as described by T. Hondo, et al., *Transplantation Proceedings*, 1987, XIX, Supp. 6, 17–22. dosage forms for external application may be prepared essentially as described in EPO Publication 0,423,714. The active object compound is included in the pharmaceutical composition in an amount sufficient to produce the desired effect upon the process or condition of diseases.

For the treatment of these conditions and diseases caused by immunoirregularity a compound of Formula I may be administered orally, topically, parenterally, by inhalation spray or rectally in dosage unit formulations containing conventional non-toxic pharmaceutically acceptable carriers, adjuvants and vehicles. The term parenteral as used herein includes subcutaneous injections, intravenous, intramuscular, intrasternal injection or infusion techniques.

For modifying the activity and/or toxicity of FK-506-type immunosuppressants, a compound of Formula I may be administered prior to, in conjunction with or subsequent to the administration FK-506-type of a compound.

Dosage levels of the compounds of the present invention are of the order from about 0.005 mg to about 50 mg per kilogram of body weight per day, preferably from about 0.1 mg to about 10 mg per kilogram of body weight per day, are useful in the treatment of the above-indicated conditions (from about 0.7 mg to about 3.5 mg per patient per day, assuming a 70 kg patient). In addition, the compounds of the present invention may be administered on an intermittent basis; i.e. at semiweekly, weekly, semi-monthly or monthly intervals.

The amount of active ingredient that may be combined with the carrier materials to produce a single dosage form will vary depending upon the host treated and the particular mode of administration. For example, a formulation intended for the oral administration of humans may contain from 0.5 mg to 5 gm of active agent compounded with an appropriate and convenient amount of carrier material which may vary from about 5 to about 95 percent of the total composition. Dosage unit forms will generally comprise from about 0.01 mg to about 500 mg, and preferably about 0.5 mg to about 100 mg of active ingredient. For external administration the compound of Formula I may be formulated within the range of, for example, 0.0001% to 60% by weight, preferably from 0.001 to 10% by weight, and most preferably from about 0.005 to 0.8% by weight.

It will be understood, however, that the specific dose level for any particular patient will depend on a variety of factors including the activity of the specific compound employed, the age, body weight, general health, sex, diet, time of administration, route of administration, rate of excretion, drug combination and the severity of the particular disease undergoing therapy.

The following examples are given for the purpose of illustrating the present invention and shall not be construed as being limitations on the scope or spirit of the instant invention.

EXAMPLE 1

17-Ethyl-1,14-dihydroxy-12-[2'-(4"-β-am ino-3"-α-methoxycyclohexyl)-1'-methylvinyl]-23,25-dimethoxy13,19,21,27-tetramethyl-11,28-dioxa-4-azatricyclo[22.3.1.0$^{4,9}$]octacos-18-ene-2,3,10,16-tetraone

Step 1A:

17-Ethyl-1-hydroxy-12-[2'-(4"-triisopropylsilyloxy-3"-methoxycyclohexyl)-1'-methylvinyl]-14-triisopropylsilyloxy-23,25-dimethoxy-13,19,21,27-tetramethyl-11,28-dioxa-4-azatricyclo-[22.3.1.0$^{4,9}$]-octacos-18-ene-2,3,10,16-tetraone To a cooled solution (0° C.) of 17-ethyl-1,14-dihydroxy-12-[2'-(4"-hydroxy-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone (120 mg) in dry methylene chloride (15 ml) was added 2,6-lutidine (64.3 mg) followed by triisopropylsilyl trifluoromethanesulfonate (184 mg). Reaction temperature was raised to r.t. and stirred overnight under nitrogen atmosphere. The reaction was quenched with 10 ml of water and extracted with ethyl acetate.

Organic layer was washed (water, sat'd NaHCO$_3$, sat'd NaCl) and dried (anhydrous MgSO$_4$). Removal of solvent followed by chromatography on silica gel (70% hexane/ethyl acetate) gave 150 mg of product.

MASS: (FAB) 1110 (M$^+$+Li).

Step 1B: Preparation of

17-Ethyl-1-hydroxy-12-[2'-(4"-hydroxy-3"-m ethoxycyclohexyl)-1'-methylvinyl]-14-triisopropylsilyloxy-23,25-dimethoxy-13,19,21,27-tetramethyl-11,28-dioxa-4-azatricyclo[22.3.1.0$^{4,9}$]-octacos-18-ene-2,3,10,16-tetraone The title compound from Example 1A (680 mg) was dissolved in methylene chloride (45 ml) and 10% solution of p-toluenesulfonic acid in methanol (45 ml) was added with stirring. The mixture was stirred at room temperature and the progress was followed by tlc analysis. After 4 hr, reaction was quenched with sat'd sodium bicarbonate and extracted with ethyl acetate three times. Normal work-up and removal of solvent followed by purification on silica gel column (80% ethyl acetate/hexane) gave 560 mg of the product (2a) as a white solid. MASS: (FAB) 954 (M$^+$+Li).

Step 1C: Preparation of

17-Ethyl-1,14-dihydroxy-12-[2'-(4"-β-azido-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone To a stirred solution of compound from Example 1B (10 mg) in acetonitrile (1 ml) was added 0.2 ml of hydrogen fluoride (48%) at room temperature. The reaction mixture was stirred for 6 hr, quenched with aqueous sodium bicarbonate and extracted with ethyl acetate. Removal of solvent, followed by chromatography on silica gel (5% i-PrOH/CH$_2$Cl$_2$) gave 6.5 mg of the title compound (Mass, IR, $^1$H and $^{13}$C NMR data consistent with compound (3a).

MASS: (FAB) 823 (M$^+$+Li). IR: 2080$^{-cm}$(-N$_3$).

Step 1D:

17-Ethyl-1,14-dihydroxy-12-[2'-4"-β-amino-3"-meth oxy-cyclohexyl)-1'-methylvinyl]-23,25-dimethoxy-13,19,21,27-tetramethyl-11,28-dioxa-4-azatricyclo[22.3.1.0$^{4,9}$]-octacos-18-ene-2,3,10,16-tetraone A solution of 17-ethyl-1,14-dihydroxy-12-[2'-(4"-azido-3"-methoxycyclohexyl)-1'-methylvinyl]-23,25-dimethoxy-13,19,21,27-tetramethyl-11,28-dioxa-4-azatri cyclo[22.3.1.0$^{4,9}$]octacos-18-ene-2,3,10,16-tetraone (3a) (28 mg) and triphenylphosphine (9 mg) in 1 ml of wet toluene was stirred at 70° C. overnight. The solvent was removed under reduced pressure, and the residue was purified by preparative tlc on silica gel (1000 microns, 1% NH$_4$OH in 5% i-PrOH/CH$_2$Cl$_2$) to give 19 mg of the title compound.

MASS: (FAB) 791 (M$^+$+H).

EXAMPLE 2

17-Ethyl-1,14-dihydroxy-12-[2'-(4"-β-azido-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone
(ALTERNATE ROUTE)

Step 2A: 17-Ethyl-1-hydroxy-12-[2'-(4"-t-butyldi methylsilyloxy-3"-methoxycyclohexyl)-1'-methylvinyl]-14-t-butyldimethylsilyloxy-23,25-dimeth-oxy-13,19,21,27-tetramethyl-11,28-dioxa-4-azatricyclo[22.3.1.0$^{4,9}$]octacos-18-ene-2,3,10,16-tetraone To a cooled solution (0° C.) of 17-ethyl-1,14-dihyd roxy-12-[2'-(4"-hydroxy-3"-methoxycyclohexyl)-1'-methylvinyl]-23,25-dimethoxy-13,19,21,27-tetra-methyl-11,28-dioxa-4-azatricyclo[22.3.1.0$^{4,9}$]octacos-18-ene-2,3,10,16-tetraone (1a) (395 mg) in dry methylene chloride (15 ml) was added 2,6-lutidine (160 mg) followed by t-butyldimethylsilyl triflouromethanesulfonate (250 mg). Reaction temperature was raised to r.t. and stirred under nitrogen atmosphere. After 6 hr, the reaction was quenched with 10 ml of water and extracted with ethyl acetate. Organic layer was washed (water, sat'd NaHCO$_3$, sat'd NaCl) and dried (anhydrous MgSO$_4$). Removal of solvent under reduced pressure gave 500 mg of crude product.

MASS: (FAB) 1023 (M$^+$+Li).

Step 2B:
17-Ethyl-1-hydroxy-12-[2'-(4"-hydroxy-3"-methoxycyclohexyl)-1'-methylvinyl]-14-t-butyldimethylsilyloxy-23,25-dimethoxy-13,19,21,27-tetramethyl-11,28-dioxa-4-azatricyclo[22.3.1.0$^{4,9}$]-octacos-18-ene-2,3,10,16-tetraone The crude product from Example 2A (500 mg) was dissolved in acetonitrile (20 ml) and 100 ml of hydrogen fluoride (48%) was added. Reaction was stirred for 20 minutes at room temperature, quenched with sat'd sodium bicarbonate, then extracted with ethyl acetate. Removal of solvent in vacuo followed by chromatography on silica gel (80% ethyl acetate/hexane) gave 300 mg of product (Mass, $^1$H and $^{13}$C NMR data consistent with the title compound.

Step 2C:
17-Ethyl-1-hydroxy-12-[2'-(4"-(2"'-nitrobenzenesulfonyl)-3"-methoxycyclohexyl)-1'-methylvinyl]-14-t-butyldimethylsilyloxy-23,25-dimethoxy-13,19,21,27-tetramethyl-11,28-dioxa-4-azatricyclo[22.3.1.0$^{4,9}$]octacos-18-ene-2,3,10,16-tetraone To a solution of compound (2b) of Example 2B (721.8 mg) in dry methylene chloride (20 mL) was added diisopropylethylamine (247.4 mg) followed by 2-nitrobenzenesulfonyl chloride (358.8 mg) and then N,N-dimethylaminopyridine (122.2 mg). The yellow solution was stirred at room temperature under a nitrogen atmosphere for 4 hr, and quenched with saturated aqueous sodium bicarbonate. The organic layer was washed (water, sat'd NaHCO$_3$, sat'd NaCl), dried (anhydrous Na$_2$SO$_4$) and the solvent was removed in vacuo. Chromatography on silica gel (65% ethyl acetate/hexane) gave 700 mg of the title compound (Mass, $^1$H and $^{13}$C NMR data consistant with the title compound.

Step 2D:
17-Ethyl-1-hydroxy-12-[2'-(4"-β-azido-3"-methoxy cyclohexyl)-1'-methylvinyl]-14-t-butyldimethylsilyloxy-23,25-dimethoxy-13,19,21,27-tetramethyl-11,28-dioxa-4-azatricyclo[22.3.1.0$^{4,9}$]-octacos-18-ene-2,3,10,16-tetraone To a stirred solution of the title compound of Example 2C (390 mg) in dry dimethylformamide (5 ml) was added sodium azide (115.7 mg) in one portion. The reaction was heated at 80° C. under nitrogen atmosphere for 4.5 hr. Reaction mixture was cooled to r.t., poured into water (50 ml), and extracted with ethyl acetate. Normal work-up followed by purification via preparative tlc on silica gel (2000 microns, 33% ethyl acetate/hexane) gave 170 mg of product (Mass, $^1$H and $^{13}$C NMR data consistent with title compound.

Step 2E:
17-Ethyl-1,14-dihydroxy-12-[2'-(4"-β-azido-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone To a stirred solution of the title compound of Example 2D (150 mg) in acetonitrile at room temperature was added hydrofluoric acid (48%, 1.5 ml). The reaction was stirred for 1.5 hr., quenched with sat'd aqueous sodium bicarbonate and extracted with ethyl acetate. The solvent was removed and the residue was purified by preparative tlc on silica gel (2000 microns, 50% ethyl acetate/hexane) to give 128 mg of the title compound. MASS: (FAB) 823 (M+ +Li).

EXAMPLE 3
17-Ethyl-1-hydroxy-12-[2'-(4"'-β-amino-3"-methoxycyclohexyl)-1'-methylvinyl]-23,25-dimethoxy-13,19,21,27-tetramethyl-11,28-dioxa-4azatricyclo[22.3.1.0$^{4,9}$]octacos-18-ene-2,3,10,16-tetraone

Step 3A:
17-Ethyl-1-hydroxy-12-[2'-(4"-azido-3"-methoxycyclohexyl)-1'-methylvinyl]-23,25-dimethoxy-13,19,21,27-tetramethyl-11,28-dioxa-4-azatricyclo[22.3.1.0$^{4,9}$]-octacos-14,18-diene-2,3,10,16-tetraone A solution of 500 mg of 17-ethyl-1,14-dihydroxy-1 2-[2'-(4"-hydroxy-3-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone in 7 ml of benzene was treated with 10 mg of p-toluenesulfonic acid and the solution was heated at 60° C. for two hours. The reaction mixture was quenched into saturated sodium bicarbonate solution and extracted with ethyl acetate. The combined organic layers were washed with water and saturated sodium chloride solution, dried with anhydrous magnesium sulfate and concentrated. The residue was chromatographed on silica gel (66% ethyl acetate: 33% hexane: 1% methanol) to give 350 mg of product. This material was dissolved in 10 ml of ethyl acetate and treated with 15 mg of 5% Rh/C. A balloon containing hydrogen was placed over the reaction mixture and the mixture stirred until the reaction was complete. The mixture was filtered through diatomaceous earth, concentrated and the residue subjected to chromatography (75% CH$_2$Cl$_2$: 5% MeOH: 20% Hexane) to give 294 mg of product. A solution of 61 mg of this material, diisopropylethyl amine (33 ml) and N,N-dimethylaminopyridine (23.2 mg) in 2 ml of methylene chloride was treated with 35.4 mg of o-nitrobenzenesulfonyl chloride under nitrogen. The reaction mixture was stirred for 4.5 hours and then diluted with aqueous sodium bicarbonate solution. The mixture was repeatedly extracted with ethyl acetate. The combined organic layers were then dried with anhydrous magnesium sulfate, concentrated and flash chromatograped on silica gel to afford 72.5 mg of product. This material was dissolved in 1.1 ml of DMF and then treated with sodium azide (24.4 mg). The reaction mixture was stirred at 80° C. under nitrogen for 4 hours and then diluted with water. The mixture was extracted with ethyl acetate and the combined fractions were washed with water, brine, dried with anhydrous magnesium sulfate and concentrated. The residue was purified by preparative TLC (66% ethyl acetate: 33% hexane: 1% MeOH) to give 28 mg of azide.

Step 3A' (ALTERNATE PREPARATION):
17-Ethyl-1-hydroxy-12-[2'-(4"'-azido-3"-methoxycyclohexyl)-1'-methylvinyl]-23,25-dimethoxy-13,19,21,27-tetramethyl-11,28-dioxa-4-azatricyclo[22.3.1.0$^{4,9}$]-octacos-14,18-diene-2,3,10,16-tetraone A solution of 17-ethyl-1,14-dihydroxy-12-[2'-(4"-azido-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone (210 mg, Example 2, step 2E) and a catalytic amount of p-toluenesulfonic acid in 40 ml of dry benzene was refluxed for 2.5 h under nitrogen atmosphere. The solvent was removed under reduced pressure and the dark brown residue was purified by column chromatography on silica gel (40% ethyl acetate/hexane) to give the title compound.
MASS: (FAB) 799 (M+H).

Step 3B:
17-Ethyl-1-hydroxy-12-[2'-(4''-β-amino-3''-methoxycyclohexyl)-1'-methylvinyl]-23,25-dimethoxy-13,19,21,27-tetramethyl-11,28-dioxa-4-azatricyclo[22.3.1.0$^{4,9}$]-octacos-18-ene-2,3,10,16-tetraone A solution of azide (23 mg) in 0.5 ml of wet toluene containing 7.8 mg of triphenylphosphine was heated at 70° C. for 17 hours. The reaction mixture was subjected to preparative TLC (88% CH$_2$Cl$_2$: 10% MeOH: 2% NH$_4$OH) to give 9 mg of the title compound.
MASS: (FAB) 775(M+).

EXAMPLE 4

17-Ethyl-1,14-dihydroxy-12-(2'-[4''-α-(o-nitrobenzenesulfonyl)-3''-β-hydroxycyclohexyl]-1'-methylvinyl)-23,25-dimethoxy-13,19,21,27-tetramethyl-11,28-dioxa-4-aza-tricyclo[22.3.1.0$^{4,9}$]octacos-18-ene-2,3,10,16-tetraone and
17-Ethyl-1,14-dihydroxy-12-(2'-[4''-α-hydroxy-3''-β-(o-nitrobenzenesulfonyl)cyclohexyl]-1'-methylvinyl)-23,25-dimethoxy-13,19,21,27-tetramethyl-11,28-dioxa-4-azatricyclo[22.3.1.0$^{4,9}$]octacos-18-ene-2,3,10,16-tetraone To a cooled solution (0° C.) of 17-ethyl-1,14-dihydroxy-12-[2'-(3''-β-4''-a-dihydroxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone (787 mg) in dry methylene chloride (15 ml) is added diisopropylethyl amine (492.4 mg) followed by o-nitrobenzenesulfonyl chloride (281 mg) and a catalytic amount of N,N-dimethylaminopyridine. The yellow solution is stirred at room temperature under a nitrogen atmosphere for 3 hr., and then quenched with saturated aqueous sodium bicarbonate. The organic layer is washed (water, sat'd NaHCO$_3$, sat'd NaCl), dried (anhydrous Na$_2$SO$_4$) and the solvent is removed in vacuo. Chromatography on silica gel gives the title compounds.

EXAMPLE 5

17-Ethyl-1,14-dihydroxy-12-[2'-(4''-β-azido-3''-β-hydroxy-cyclohexyl)-1'-methylvinyl]-23,25-dimethoxy-13,19,21,27-tetramethyl-11,28-dioxa-4-azatricyclo[22.3.1.0$^{4,9}$]-octacos-18-ene-2,3,10,16-tetraone To a stirred solution of 17-ethyl-1,14-dihydroxy-12-(2'-[4''-(o-nitrobenzenesulfonyl)-3''-hydroxy cyclohexyl]-1'-methylvinyl)-23,25-dimethoxy-13,19,21,27-tetramethyl-11,28-dioxa-4-azatricyclo[22.3.1.0$^{4,9}$]-octacos-18-ene-2,3,10,16-tetraone (87 mg) in dry dimethylformamide (1 ml) is added sodium azide (16.7 mg) in one portion. The reaction is heated at 80° C. under nitrogen atmosphere for 3 hr. The reaction mixture is cooled, poured into water (5 ml) and extracted with ethyl acetate. Normal work-up followed by preparative tlc on silica gel gives title compound.

EXAMPLE 6

17-Ethyl-1,14-dihydroxy-12-[2'-(4''-α-hydroxy-3''-α-azidocyclohexyl)-1'-methylvinyl]-23,25-dimethoxy-13,19,21,27-tetramethyl-11,28-dioxa-4-azatricyclo[22.3.1.0$^{4,9}$]-octacos-18-ene-2,3,10,16-tetraone The title compound is prepared by the method of Example 5 utilizing 17-ethyl-1,14-dihydroxy-12-(2'-[4''-hydroxy-3''-(o-nitrobenzenesulfonyl)cyclohexyl]-1'-methylvinyl)-23,25-dimethoxy-13,19,21,27-tetramethyl-11,28-dioxa-4-azatricyclo[22.3.1.0$^{4,9}$]-octacos-18-ene-2,3,10,16-tetraone.

EXAMPLE 7

17-Ethyl-1,14-dihydroxy-12-[2'-(4''-β-amino-3''-β-hydroxy-cyclohexyl)-1'-methylvinyl]-23,25-dimethoxy-13,19,21,27-tetramethyl-11,28-dioxa-4-azatricyclo[22.3.1.0$^{4,9}$]-octacos-18-ene-2,3,10,16-tetraone A solution of 17-ethyl-1,14-dihydroxy-12-[2'-(4''-b-azido-3''-a-hydroxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone (3d) (28 mg) and triphenylphosphine (9 mg) in 1 ml of wet toluene is stirred at 70° C. overnight. The solvent is removed under reduced pressure, and the residue is purified by preparative tlc on silica gel to give title compound.

EXAMPLE 8

17-Ethyl-1,14-dihydroxy-12-[2'-(4''-hydroxy-3''-amino-cyclohexyl)-1'-methylvinyl]-23,25-dimethoxy-13,19,21,27-tetramethyl-11,28-dioxa-4-azatricyclo[22.3.1.0$^{4,9}$]-octacos-18-ene-2,3,10,16-tetraone The title compound is prepared by the method of Example 7 utilizing 17-ethyl-1,14-dihydroxy-12-[2'-(4''-hydroxy-3''-azidocyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone.

EXAMPLE 9

17-Ethyl-1-hydroxy-12-[2'-(3''-methoxy-4''-oxocyclohexyl)-1'-methylvinyl]-14-triisopropylsilyloxy-23,25-dimethoxy-13,19,21,27-tetramethyl-11,28-dioxa-4-azatricyclo[22.3.1.0$^{4,9}$]octacos-18-ene-2,3,10,16-tetraone To a cooled solution (−78° C.) of oxalyl chloride (1.5 ml of 2M solution in CH$_2$Cl$_2$) was added dimethyl sulfoxide (361 mg) dropwise, followed by a solution of 17-ethyl-1-hydroxy-12-[2'-(4''-hydroxy-3''-methoxycyclohexyl)-1'-methylvinyl]-14-triisopropylsiloxy-23,25-dimethoxy-13,19,21,27-tetramethyl-11,28-dioxa-4-azatricyclo[22.3.1.0$^{4,9}$]octacos-18-ene-2,3,10,16-tetraone (947 mg) in dry methylene chloride (3 ml). The reaction mixture was stirred for 30 min. at −78° C. and then triethylamine (1 ml) was added. The reaction temperature was raised to room temperature, reaction was poured into water (20 ml), and extracted with ethyl acetate (three times). The combined organic layers were washed (water, sat'd NaHCO$_3$), dried (anhydrous Na$_2$SO$_4$), and filtered. Removal of solvent followed by purification (silica gel chromatography, 40% ethyl acetate: 60% hexane) gave 870 mg of title compound.

EXAMPLE 10

17-Ethyl-1,14-dihydroxy-12-[2'-(3''-methoxy-4''-oxocyclohexyl)-1'-methylvinyl]-23,25-dimethoxy-13,19,21,27-tetramethyl-11,28-dioxa-4-azatricyclo]22.3.1.0$^{4,9}$]-octacos-18-ene-2,3,10,16-tetraone To a stirred solution of 17-ethyl-1-hydroxy-12-[2'-(3''-methoxy-4''-oxocyclohexyl)-1'-methylvinyl]-14-triisopropylsilyloxy-23,25-dimethoxy-13,19,21,27-tetramethyl-11,28-dioxa-4-azatricyclo[22.3.1.0$^{4,9}$]-octacos-18-ene-2,3,10,16-tetraone from example 9 (870 mg) in acetonitrile (20 ml) was added hydrofluoric acid (48%, 1 ml) at room temperature. The reaction progress was monitored by TLC analysis and after 4 hr. the reaction mixture was quenched with sat'd aqueous sodium bicarbonate. The organic layer was separated and the aqueous layer was extracted with ethyl acetate three times. The combined organic layers were washed (sat'd NaHCO$_3$, sat'd NaCl), dried (anhydrous Na$_2$SO$_4$), and filtered. Removal of solvent followed by purification (silica gel column chromatography, 50% ethyl acetate/hexane) gave 600 mg of title compound.

EXAMPLE 12

17-Ethyl-1,14-dihydroxy-12-[2'-(4''-amino-3''-isopropyloxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone To a solution of 17-ethyl-1,14-dihydroxy-12-[2'-(4''-hydroxy-3''-isopropyloxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone (145 mg) in dry methylene chloride (4 ml) was added an excess of 2,6-lutidine (62 ml) and the mixture was stirred at room temperature. After 10 minutes, tert-butyldimethylsilyl trifluoromethanesulfonate (81 ml) was added via syringe. After 15 minutes the reaction mixture was diluted with ethyl acetate, extracted with saturated sodium bicarbonate, washed with brine and the organic phase dried over magnesium sulfate. Removal of the solvent in vacuo and flash chromatography on silica gel (ethyl acetate:hexane (1:2) +1% methanol) gave the bis-protected compound (130 mg). To a solution of this compound in acetonitrile (4 ml) was added a solution of 2% HF in aqueous acetonitrile (70 ml), and the mixture stirred at room temperature. After 5.5 hours, the solution was diluted with ethyl acetate, extracted with saturated sodium bicarbonate solution and the organic phase dried over magnesium sulfate. Purification of the concentrate by flash chromatography on silica gel (ethyl acetate:hexane (1:2) +1% methanol) gave the mono-protected compound (80 mg). To a solution of this compound in dry methylene chloride (1 ml) was added an excess of diisopropylethylamine (36 ml) and o-nitrophenylsulfonyl chloride (39 mg) followed by addition of 4-dimethylaminopyridine (22 mg). The mixture was stirred at room temperature for 5 hours at which time it was diluted with ethyl acetate, extracted from half saturated sodium bicarbonate solution and washed with brine. The combined organics were dried over magnesium sulfate and the concentrate purified by flash chromatography on silica gel (ethyl acetate:hexane (1:2) +1% methanol) to give product (87 mg). To a solution of this compound in N,N-dimethylformamide (1 ml) was added an excess of sodium azide (25 mg) and the mixture heated to 70° C. After 7.5 hours the reaction mixture was cooled to room temperature, diluted with ethyl acetate, extracted from half-saturated ammonium chloride, and washed with brine. The combined organics were dried over sodium sulfate and purified by flash chromatography on silica gel (ethyl acetate:hexane (1:2) +1% methanol) to give the azide compound (38 mg). To a solution of this protected azide in acetonitrile (1 ml) was added a solution of 2% HF in aqueous acetonitrile (150 ml), and the mixture stirred at room temperature. After 4.5 hours, the solution was diluted with ethyl acetate, extracted with saturated sodium bicarbonate solution and the organic phase dried over magnesium sulfate. Purification of the concentrate by flash chromatography on silica gel (ethyl acetate:hexane (1:2) +1% methanol) gave the deprotected compound (22.5 mg). To a solution of the azido compound in 10% aqueous toluene (0.5 ml) was added triphenylphosphine (10.7 mg) and the mixture heated to 70° C. with stirring. After 18 hours the reaction mixture was cooled, then concentrated to 10% volume in vacuo, and purified by preparative TLC on silica gel (2% ammonium hydroxide, 5% methanol in methylene chloride) to give the title compound (5.5 mg). partial $^1$H NMR d: 5.19 (brs, 1H); 4.59 (brd, J=4 Hz, 1H); 4.41 (brd, J=14 Hz, 1H); 1.16 (d, J=7 Hz); 1.13 (d, J=7 Hz, 3H).

EXAMPLE 13

17-ethyl-1-hydroxy-12-[2'-(4'',3''-dihydroxyoxycyclohexyl)-1'-methylvinyl]-23,25-dimethoxy-13,19,21,27-tetramethyl-11,28-dioxa-4-azatricyclo-[22.3.1.0$^{4,9}$]octacos-18-ene-2,3,10,16-tetraone A solution of 17-ethyl-1,14-dihydroxy-12-[2'-(4''-hydroxy-3''-isopropyloxycyclohexyl)-1'-methylvinyl]-23,25-dimethoxy-13,19,21,27-tetramethyl-11,28-dioxa-4-azatricyclo-[22.3.1.0$^{4,9}$]octacos-18-ene-2,3,10,16-tetraone (210 mg) and a catalytic amount of p-toluenesulfonic acid in 40 ml of benzene was refluxed for 4 hours under a nitrogen atmosphere. The solvent was removed under reduced pressure and the dark residue was purified by chromatography (silica gel, 7% i-propanol/CH$_2$Cl$_2$) to give 17-ethyl-1-hydroxy-12-[2'-(4''-hydroxy-3''-isopropyloxycyclohexyl)-1'-methylvinyl]-23,25-dimethoxy-13,19,21,27-tetramethyl-11,28-dioxa-4-azatricyclo-[22.3.1.0$^{4,9}$]octacos-14,18-diene-2,3,10,16-tetraone (180 mg) as a white solid. This material was dissolved in ethanol (20 ml) and treated with 5% Rh/C (40 mg). Hydrogen was introduced via balloon for 30 min. and the mixture was filtered through celite. Removal of solvent followed by chromatography (silica gel) gave 172 mg of the title compound. Mass, $^1$H and $^{13}$C NMR data were consistant with the title structure.

EXAMPLE 14

17-ethyl-1-hydroxy-12-[2'-(4''-hydroxy-3''-isopropyloxycyclohexyl)-1'-methylvinyl]-23,25-dimethoxy-13,19,21,27-tetramethyl-11,28-dioxa-4-azatricyclo-[22.3.1.0$^{4,9}$]octacos-18-ene-2,3,10,16-tetraone To a solution of 17-ethyl-1-hydroxy-12-[2'-(4'',3''-dihydroxyoxycyclohexyl)-1'-methylvinyl]-23,25-dimethoxy-13,19,21,27-tetramethyl-11,28-dioxa-4-azatricyclo-[22.3.1.0$^{4,9}$]octacos-18-ene-2,3,10,16-tetraone (200 mg) in diethyl ether (6 ml) is added boron trifluoride etherate (10 ml) followed by freshly prepared 2-diazopropane (100-fold excess). The mixture is stirred at room temperature for 15 min. and quenched with sat'd aqueous sodium bicarbonate solution. The organic layer is separated, washed with sat's NaCl and dried over sodium sulfate. Removal of solvent followed by preparative TLC on silica gives the title compound and its 4'' isomer.

EXAMPLE 15

17-Ethyl-1-hydroxy-12-[2'-(4''-amino-3''-isopropyloxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone To a solution of 17-ethyl-1-hydroxy-12-[2'-(4''-hydroxy-3''-isopropyloxycyclohexyl)-1'-methylvinyl]-23,25-dimethoxy-13,19,21,27-tetramethyl-11,28-dioxa-4-azatricyclo-[22.3.1.0$^{4,9}$]octacos-18-ene-2,3,10,16-tetraone (158 mg) in dry methylene chloride (3.5 ml) was added an excess of diisopropylethylamine (82 ml) and o-nitrophenylsulfonyl chloride (87 mg) followed by addition of 4-dimethylaminopyridine (58 mg). The mixture was stirred at room temperature for 23 hours at which time it was diluted with ethyl acetate, extracted from saturated sodium bicarbonate solution and washed with brine. The combined organics were dried over magnesium sulfate and the concentrate purified by flash chromatography on silica gel (ethyl acetate:hexane (1:1) +1% methanol) to give the activated compound (130 mg). To a solution of this compound in N,N-dimethylformamide (2 ml) was added an excess of sodium azide (43 mg) and the mixture heated to 70° C. After 4 hours the reaction mixture was cooled to room temperature, diluted with ethyl acetate, extracted from half-saturated ammonium chloride, and washed with brine. The combined organics were dried over magnesium sulfate and purified by flash chromatography on silica gel (ethyl acetate:hexane (1:2) +1% methanol) to give the azido compound (50 mg). To a solution of this compound in 10% aqueous benzene (1.7 ml) was added triphenylphosphine (24 mg) and the mixture heated to 70° C. with stirring. After 17 hours, the reaction mixture is cooled, concentrated to 10% volume in vacuo and applied directly to a column of silica gel for purification by flash chromatography (ethyl acetate:hexane (1:1) +1% methanol then 2% ammonium hydroxide, 5% methanol in methylene chloride) to give the title compound (38 mg).

MASS: (FAB) 802 (M+). partial $^1$H NMR d: 4.58 (brs, J=4 Hz, 1H); 4.41 (brd, J=4 Hz, 1H); 3.87 (dd, J=12, 3 Hz, 1H).

EXAMPLE 16

17-Ethyl-1-hydroxy-12-[2'-(4''-azido-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone A solution of 17-ethyl-1-hydroxy-12-[2'-(4''-azido-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-14,18-diene-2,3,10,16-tetraone (55 mg, Example 3), tetrakistriphenylphosphine palladium (10 mg), and acetic acid (10 ml) in 3 ml of dry toluene was stirred for 5 min at room temperature under nitrogen atmosphere. To this yellow solution was added tributyltin hydride (40 ml) and stirred an additional 45 min. at room temperature. The brown colored reaction mixture was subjected to column chromatography on silica gel (eluted first with hexane and then with 50% ethyl acetate/hexane) to give 50 mg of the title compound. Mass and $^1$H NMR data were consistent with the structure.

EXAMPLE 17

17-Ethyl-1-hydroxy-12-[2'-[4''-α-(2'''-nitrobenzenesulfonyloxy)-3''-b-hydroxycyclohexyl]-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone (B) and
17-Ethyl-1-hydroxy-12-[2'-[3''-(2'''-nitrobenzenesulfonyloxy)-4''-hydroxycyclohexyl]-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone (A)

To a solution of 17-ethyl-1-hydroxy-12-[2'-(3'',4''-'-dihydroxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone (200 mg) in dry methylene chloride (20 ml) was added diisopropylethylamine (150 ml) followed by 2-nitrobenzenesulonyl chloride (60 mg), then 4-dimethylaminopyridine (27 mg). The yellow solution was stirred at room temperature under nitrogen atmosphere for 4 h, then quenched with sat'd aqueous sodium bicarbonate solution. The organic layer was washed (water, sat'd NaHCO$_3$, sat'd NaCl), dried (anhydrous Na$_2$SO$_4$) and the solvent was removed in vacuo. Chromatography on silica gel (2:1 ethyl acetate/hexane) gave 70 mg of the title compound (A) and 60 mg of the title compound (B) (Mass, $^1$H and $^{13}$C NMR data were consistent with the structures).

EXAMPLE 18

17-Ethyl-1-hydroxy-12-[2'-(3''-β(R)-4''-β-(S)-epoxy cyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone To a solution of 17-ethyl-1-hydroxy-12-[2'-[4''-α-R)-(2'''-nitrobenzenesulfonyloxy)-3''-β-(S)-hydroxycyclohexyl]-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone (Example 17) (60 mg) in 3 ml of dry methylene chloride was added triethylamine (1 ml) and stirred at room temperature for 3 days. The solvent was removed under reduced pressure and the residue was purified by column chromatography on silica gel (2:3 hexane/ethyl acetate) to give 42 mg of title compound (8b-1).

MASS: (FAB) 744 (M+H), 766 (M+Na).

EXAMPLE 19

17-Ethyl-1-hydroxy-12-[2'-(3''-α-(S)-4''-α-(R)-epoxy cyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone The title compound was prepared by the method of Example 19 utilizing 17-ethyl-1-hydroxy-12-[2'-[3''-(2'''-nitrobenzenesulfonyloxy)-4''-hydroxycyclohexyl]-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone (Example 17) as starting material.

EXAMPLE 20

17-Ethyl-1-hydroxy-12-[2'-(4''-α-(R)-azido-3'
'-β-(S)-hydroxycyclo-hexyl)-1'-methylvinyl]-23,25-
dimethoxy-13,19,21,27-tetramethyl-11,28-dioxa-4-aza-
tricyclo[22.3.1.0$^{4,9}$]octacos-18-ene-2,3,10,16-tetraone
(9a)

To a solution of 17-ethyl-1-hydroxy-12-[2'-(3''-β-(R)
-4''-β-(S)-epoxycyclohexyl)-1'-methylvinyl]-23,25-
dimethoxy-13,19,21,27-tetramethyl-11,28-dioxa-4-aza-
tricyclo[22.3.1.0$^{4,9}$]octacos-18-ene-2,3,10,16-tetraone
(200 mg) in ethanol (5 ml) was added a mixture of sodium azide (100 mg) and ammonium chloride (14 mg) in warm water (250 ml). The reaction mixture was heated at 60° C. for 4 h in an oil bath and cooled to room temperature. Removal of solvent in vacuo followed by chromatography on silica gel (60% ethyl acetate/hexane) gave 132 mg of title compound. IR: 2100 cm$^{-1}$ (N$_3$).

EXAMPLE 21

17-Ethyl-1-hydroxy-12-[2'-(3''-azido-4''-hydroxycyclohexyl)-1'-methylvinyl]-23,25-dimethoxy-13,19,21,27-
tetramethyl-11,28-dioxa-4-azatricyclo[22.3.1.0$^{4,9}$]octacos-18-ene-2,3,10,16-tetraone The title compound was prepared by the method of Example 20 utilizing 17-ethyl-1-hydroxy-12-[2'-(3''(S),4''(R)-epoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone as starting material.

EXAMPLE 22

17-Ethyl-1-hydroxy-12-[2'-(4''-α-(R)-azido-3
''-β-(S)-methoxycyclohexyl)-1'-methylvinyl]-23,25-
dimethoxy-13,19,21,27-tetramethyl-11,28-dioxa-4-aza-
tricyclo[22.3.1.0$^{4,9}$]octacos-18-ene-2,3,10,16-tetraone A suspension of 17-ethyl-1-hydroxy-12-[2'-(4''-α-(R)-azido-3''-β-(S)-hydroxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone and silver oxide (20 mg) in 1.5 ml of methyl iodide was refluxed in a gas-tight bottle for 4 days. The yellow solid was filtered off and the excess methyl iodide was removed. Purification of crude material by preparative tlc on silica gel (1:1 hexane/ethyl acetate) gave 4 mg of the title compound.

MASS: (FAB) 807 (M+Li).

EXAMPLE 23

17-Ethyl-1-hydroxy-12-[2'-(4''-α-(R)-amino-3
''-β-(S)-methoxycyclohexyl)-1'-methylvinyl]-23,25-
dimethoxy-13,19,21,27-tetramethyl-11,28-dioxa-4-aza-
tricyclo[22.3.1.0$^{4,9}$]octacos-18-ene-2,3,10,16-tetraone A solution of 17-ethyl-1-hydroxy-12-[2'-(4''-α-(R)-azido-3''-β-(S)-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone (20 mg, Example 22) and triphenylphosphine (7 mg) in 3 ml of 10% water/benzene was refluxed for 16 h in an oil bath. The solvent was removed in vacuo and the crude material was purified by column chromatography on silica gel (eluted first with 5% MeOH/CH$_2$Cl$_2$, then 1% NH$_4$OH in 5% MeOH/CH$_2$Cl$_2$) to give 12 mg of title compound (10a).

MASS: (FAB) 775 (M+H), 799 (M+Na).

EXAMPLE 24

17-Ethyl-1-hydroxy-12-[2'-(4''-α-hydroxy-3''-β-ethoxycyclohexyl)-1'-methylvinyl]-23,25-
dimethoxy-13,19,21,27-tetramethyl-11,28-dioxa-4-aza-
tricyclo-[22.3.1.0$^{4,9}$]octacos-18-ene-2,3,10,16-tetraone To a solution of 17-ethyl-1-hydroxy-12-[2'-(3'',4'-dihydroxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone (200 mg, from Example 3) in ether (6 ml) is added borontrifluoride etherate (10 ml) followed by freshly prepared diazoethane (100 fold excess). The mixture is stirred at room temperature for 15 min and quenched with sat'd aqueous sodium bicarbonate solution. The organic layer is separated, washed (sat'd aqueous NaCl) and dried over anhydrous magnesium sulfate. Removal of solvent followed by preparative tlc on silica to separate the regioisomers gives the title compound.

EXAMPLE 25

17-Ethyl-1-hydroxy-12-[2'-[4''-α-(2'''-nitrobenzenesulfonyloxy)-3''-β-ethoxycyclohexyl]-1'-methylvinyl]-
23,25-dimethoxy-13,19,21,27-tetramethyl-11,28-dioxa-
4-azatricyclo[22.3.1.0$^{4,9}$]octacos-18-ene-2,3,10,16-tetraone To a solution of 17-ethyl-1-hydroxy-12-[2'-(4''-α-hydroxy-3''-β-ethoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone (200 mg, Example 24) in dry methylene chloride (2 ml) is added diisopropylethylamine (150 ml) followed by 2-nitrobenzenesulonyl chloride (60 mg), then 4-dimethylaminopyridine (27 mg). The yellow solution is stirred at room temperature under nitrogen atmosphere for 4 h, then quenched with sat'd aqueous sodium bicarbonate solution. The organic layer is washed (water, sat'd NaHCO$_3$, sat'd NaCl), dried (anhydrous Na$_2$SO$_4$) and the solvent is removed in vacuo. Chromatography on silica gel gives the title compound.

EXAMPLE 26

17-Ethyl-1-hydroxy-12-[2'-[4''-β-azido-3
''-β-ethoxycyclohexyl]-1'-methylvinyl]-23,25-dimethoxy-13,19,21,27-tetramethyl-11,28-dioxa-4-azatricyclo-[22.3.1.0$^{4,9}$]octacos-18-ene-2,3,10,16-tetraone To a stirred solution of 17-ethyl-1-hydroxy-12-[-2'-[4''-α-(2'''-nitrobenzenesulfonyloxy)-3''-β-ethoxycyclohexyl]-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone (87 mg, Example 25) in dry DMF (1 ml) is added sodium azide (16.7 mg) in one portion. The reaction is heated at 80° C. under nitrogen atmosphere for 3 h. The reaction mixture is cooled, poured into water (5 ml) and extracted with ethyl acetate. Normal work-up followed by preparative tlc on silica gel gives the title compound.

EXAMPLE 27

17-Ethyl-1-hydroxy-12-[2'-[4''-β-amino-
3''-α-ethoxycyclohexyl]-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone A solution of 17-ethyl-1-hydroxy-12-[2'-[4''-azido-3''-ethoxycyclohexyl]-1'-methylvinyl]-23,25- dimethoxy-13,19,21,27-tetramethyl-11,28-dioxa-4-azatricyclo[22.3.1.0$^{4,9}$]octacos-18-ene-2,3,10,16-tetraone (28 mg, Example 26) and triphenylphosphine (9 mg) in 1 ml of wet benzene is refluxed overnight. The solvent is removed in vacuo and the residue is purified on silica gel column to give the title compound.

EXAMPLE 28

17-Ethyl-1-hydroxy-12-[2'-(4''-β-(2-furan yl)methylamino-3''-methoxycyclohexyl)-1'-methylvinyl]-23,25-dimethoxy-13,19,21,27-tetramethyl-11,28-dioxa-4-azatricyclo-[22.3.1.0$^{4,9}$]octacos-18-ene-2,3,10,16-tetraone To a solution of 17-ethyl-1-hydroxy-12-[2-(4''-β-amino-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone (4c, EXAMPLE 3) (0.038 gm, 0.049 mmol) in predried methanol (2 ml) and predried molecular sieves was added furaldehyde (10 ul, 0.104 mmol). The reaction mixture was stirred at rt until the amine had been converted to Schiff base (45 min. as evaluated by TLC, silica, 1:9, methanol:methylene chloride). To this solution was added a solution of NaCNBH$_3$ (62.8 mg, 0.02 mmol) in methanol (10 ml). After the addition of 10 ul of acetic acid, the reaction mixture was stirred for an additional 10 min. at which time it was filtered and the filtrate was evaporated in vacuo. The yellow residue was purified by chromatography (silica, 3:2, ethyl acetate:hexanes) to provide 22 mg of the title compound.

MASS, M+H 855, M+Li 861.

Partial $^1$H NMR δ:7.32 (bs, 1H); 6.28 (bs, 1H); 6.15 (bs, 1H); 3.85 (d, J=16 Hz, 1H); 3.65 (d, J=16 Hz, 1H).

EXAMPLE 29

17-Ethyl-1-hydroxy-12-[2''-(4''-(2-thiophene)methyl amino-3''-methoxycyclohexyl)-1'-methylvinyl]-23,25-dimethoxy-13,19,21,27-tetramethyl-11,28-dioxa-4-azatricyclo-[22.3.1.0$^{4,9}$]octacos-18-ene-2,3,10,16-tetraone The title compound was prepared from 17-ethyl-1-hydrocy-12-[2'-4''-β-amino-3''-methoxycyclohexyl)-1-methylvinyl]-23,25-dimethoxy-13,19,21,27-tetramethyl-11,28-dioxa-4azatricyclo[22.3.1.0$^{4,9}$]-octacos-18-ene-2,3,10,16-tetraone (Example 3) (0.04 gm, 0.052 mmol) and thiophene-2-carboxaldehyde according to procedures outlined in Example 28.

MASS, M+Li 877.8 M=Na 893.8.

Partial $^1$H NMR δ:7.16 (d, J=6 Hz, 1H); 6.9 (m, 2H); 3.99 (dd, J=16 Hz, 1H); 3.88 (d, J=16 Hz).

EXAMPLE 30

17-Ethyl-1-hydroxy-12-[2'-(4''-β-(pyrid-2-yl)methylamino-3''-methoxycyclohexyl)-1'-methylvinyl]-23,25-dimethoxy-13,19,21,27-tetramethyl-11,28-dioxa-4-azatricyclo-[22.3.1.0$^{4,9}$]octacos-18-ene-2,3,10,16-tetraone The title compound (32 mg) was prepared from 17-Ethyl-1-hydroxy-12-[2'-(4''-β-amino-3''-methoxycyclohexyl)-1'-methylvinyl]-23,25-dimethoxy-13,19,21,27-tetramethyl-11,28-dioxa-4azatricyclo[22.3.1.0$^{4,9}$]octacos-18-ene-2,3,10,16-tetraone (Example 3) (0.04 gm, 0.052 mmol) and pyridine-2-carboxaldehyde according to procedures outlined in Example 28.

MASS, M+Li 872.

Partial $^1$H NMR δ:8.54 (dd, J=4 Hz, 1H); 7.64 (m, 1H); 7.29 (m, 1H); 7.13 (dd, J=4 Hz and 7 Hz); 3.94 (d, 16 Hz, 1H); 3.8 (d, 16 Hz, 1H).

EXAMPLE 31

17-Ethyl-1-hydroxy-12-[2'-(4''-β-(pyrid-4-yl)methylamino-3''-methoxycyclohexyl)-1'-methylvinyl]-23,25-dimethoxy-13,19,21,27-tetramethyl-11,28-dioxa-4-azatricyclo-[22.3.1.0$^{4,9}$]octacos-18-ene-2,3,10,16-tetraone The title compound (55 mg) was prepared from 17-Ethyl-1-hydroxy-12-[2'-(4''-β-amino-3''-methoxycyclohexyl)-1'-methylvinyl]-23,25-dimethoxy-13,19,21,27-tetramethyl-11,28-dioxa-4azatricyclo[22.3.1.0$^{4,9}$]octacos-18-ene-2,3,10,16-tetraone (Example 3) and pyridyl-4-carboxaldehyde according to procedures described in Example 28.

MASS, M+Li 872.7, M+Li+H+874.

EXAMPLE 32

17-Ethyl-1-hydroxy-12-[2'-(4''-β-(1-methyl-pyrid-2-yl)amino-3''-methoxycyclohexyl)-1'-methylvinyl]-23,25-dimethoxy-13,19,21,27-tetramethyl-11,28-dioxa-4-azatricyclo-[22.3.1.0$^{4,9}$]octacos-18-ene-2,3,10,16-tetraone To a solution of 17-ethyl-1-hydroxy-12-[2'-(4''-β-amino-3''-methoxycyclohexyl)-1'-methylvinyl]-23,25-dimethoxy-13,19,21,27-tetramethyl-11,28-dioxa-4azatricyclo[22.3.1.0$^{4,9}$]octacos-18-ene-2,3,10,16-tetraone (Example 3) (0.06 gm, 0.073 mmol) in DMF (predried, 1.5 ml) was added 1-methylpyridinium iodide (0.028 gm, 0.11 mmol) and the reaction mixture was stirred at rt for a period of 30 min. The reaction mixture was then diluted with a mixture of H2O (10 ml) and benzene (20 ml) and this heterogeneous solution was freeze dried. The resulting yellow solid was triturated with water and then ether to give 57 ug of the title compound.

EXAMPLE 33

17-Ethyl-1-hydroxy-12-[2'-(4''-β-(imidazol-2-yl)methylamino-3''-methoxycyclohexyl)-1'-methylvinyl]-23,25-dimethoxy-13,19,21,27-tetramethyl-11,28-dioxa-4-azatricyclo-[22.3.1.0$^{4,9}$]octacos-18-ene-2,3,10,16-tetraone The title compound was prepared from 17-ethyl-1-hydroxy-12-[2'-(4''-β-amino-3''-methoxycyclohexyl)-1'-methylvinyl]-23,25-dimethoxy-13,19,21,27-tetramethyl-11,28-dioxa-4azatricyclo[22.3.1.0$^{4,9}$]octacos-18-ene-2,3,10,16-tetraone (Example 3) and imidazole-3-carboxaldehyde according to procedures described in Example 28.

MASS, M+2Li 856.

Partial $^1$H NMR δ:6.96 (bs, 2H), 3.99 (bdd, J=15 Hz and 9 Hz, 2H)

EXAMPLE 34

17-Ethyl-1-hydroxy-12-[2'-(4''-β-(imidazolin-2-yl)methylamino-3''-methoxycyclohexyl)-1'-methylvinyl]-23,25-dimethoxy-13,19,21,27-tetramethyl-11,28-dioxa-4-azatricyclo-[22.3.1.0$^{4,9}$]octacos-18-ene-2,3,10,16-tetraone To a solution of 17-ethyl-1-hydroxy-12-[2'-(4''-β-amino-3''-methoxycyclohexyl)-1'-methylvinyl]-23,25-dimethoxy-13,19,21,27-tetramethyl-11,28-dioxa-4-azatricyclo[22.3.1.0$^{4,9}$]-octacos-18-ene-2,3,10,16-tetraone (Example 3) (0.04 gm), 2-methylthioimidazoline (0.014 gm) and triethylamine (7 uL) in acetonitrile was stirred under an $N_2$ atmosphere at 40° C. for 18 hr. The solvent was removed in vacuo and the residue was purified by chromatography (silica, 10% methanol: methylene chloride) to give 24 mg of the title compound.

MASS, M+Li 849.

EXAMPLE 35

17-Ethyl-1-hydroxy-12-[2'-(4''-β-(1-methylindol-5-yl)methylamino-3''-methoxycyclohexyl)-1'-methylvinyl]-23,25-dimethoxy-13,19,21,27-tetramethyl-11,28-dioxa-4-azatricyclo-[22.3.1.0$^{4,9}$]octacos-18-ene-2,3,10,16-tetraone The title compound (40 mg) was prepared from 17-ethyl-1-hydroxy-12-[2'-(4''-β-amino-3''-methoxycyclohexyl)-1'-methylvinyl]-23,25-dimethoxy-13,19,21,27-tetramethyl-11,28-dioxa-4azatricyclo[22.3.1.0$^{4,9}$]octacos-18-ene-2,3,10,16-tetraone (4c, EXAMPLE 3) and 1-methylindole-5-carboxaldehyde according to procedures outlined in Example 28.

MASS, M+H 918.9

Partial $^1$H NMR δ:7.54 (s, 1H); 7.23 (m, 2H); 7.03 (d, J=4 Hz, 1H); 6.41 (d, J=4 Hz, 1H); 3.76 (s, 3H); 3.14 (s, 3H)

EXAMPLE 36

17-Ethyl-1-hydroxy-12-[2'-(4''-α-(1-methylindol-5--yl)methylamino-3''-methoxycyclohexyl)-1'-methylvinyl]-23,25-dimethoxy-13,19,21,27-tetramethyl-11,28-dioxa-4-azatricyclo-[22.3.1.0$^{4,9}$]octacos-18-ene-2,3,10,16-tetraone The title compound (16 mg) was prepared from 17-ethyl-1-hydroxy-12-[2'-(4''-α-amino-3''-methoxycyclohexyl)-1'-methylvinyl]-23,25-dimethoxy-13,19,21,27-tetramethyl-11,28-dioxa-4azatricyclo[22.3.1.0$^{4,9}$]octacos-18-ene-2,3,10,16-tetraone (10a, EXAMPLE 23) and indole-3-carboxaldehyde according to procedures described in Example 28.

MASS, M+H 918.9, M+Li 924.8

Partial $^1$H NMR δ:7.69 (d, J=8 Hz, 1H); 7.35 (m, 1H); 7.10 (d, 2 Hz, 1H); 6.51 (d, 2 Hz, 1H); 6.41 (d, 2 Hz, 1H); 3.79 (s, 3H).

EXAMPLE 37

17-Ethyl-1-hydroxy-12-[2'-(4''-β-(indol-3-yl)methylamino-3''-methoxycyclohexyl)-1'-methylvinyl]-23,25-dimethoxy-13,19,21,27-tetramethyl-11,28-dioxa-4-azatricyclo-[22.3.1.0$^{4,9}$]octacos-18-ene-2,3,10,16-tetraone The title compound (16 mg) was prepared from 17-Ethyl-1-hydroxy-12-[2'-(4''-β-amino-3''-methoxycyclohexyl)-1'-methylvinyl]-23,25-dimethoxy-13,19,21,27-tetramethyl-11,28-dioxa-4azatricyclo[22.3.1.0$^{4,9}$]octacos-18-ene-2,3,10,16-tetraone (Example 3) and indole-3-carboxaldehyde according to procedures described in Example 28.

MASS, M+Li 910.

Partial $^1$H NMR δ: 8.5 (bs, 1H); 7.63 (d, J=8 Hz, 1H); 7.37 (d, J=8 Hz, 1H); 7.31 (bs, 1H); 7.19 (t, J=7 Hz and 6 Hz, 1H); 7.10 (t, J=7 Hz and 6 Hz, 1H); 3.12 (s, 3H).

EXAMPLE 38

17-Ethyl-1-hydroxy-12-[2'-(4''-β-(pyrrol-2-yl)methylamino-3''-methoxycyclohexyl)-1'-methylvinyl]-23,25-dimethoxy-13,19,21,27-tetramethyl-11,28-dioxa-4-azatricyclo-[22.3.1.0$^{4,9}$]octacos-18-ene-2,3,10,16-tetraone The title compound (20.5 mg) was prepared from 17-ethyl-1-hydroxy-12-[2'-(4''-β-amino-3''-methoxycyclohexyl)-1'-methylvinyl]-23,25-dimethoxy-13,19,21,27-tetramethyl-11,28-dioxa-4azatricyclo[22.3.1.0$^{4,9}$]octacos-18-ene-2,3,10,16-tetraone (Example 3) and pyrrole-2-carboxaldehyde according to procedures described in Example 28.

MasS, M+Li 860.8

Partial $^1$H NMR peaks δ: 9.45 (bs, 1H); 6.75 (bs, 1H); 6.19 (m, 2H); 3.86 (m, 2H).

EXAMPLE 39

17-Ethyl-1-hydroxy-12-[2'-(4''-β-(1-methyl-5-indolyl)amino-3''-methoxycyclohexyl)-1'-methylvinyl]-23,25-dimethoxy-13,19,21,27-tetramethyl-11,28-dioxa-4-azatricyclo-[22.3.1.0$^{4,9}$]octacos-18-ene-2,3,10,16-tetraone To a solution of 17-Ethyl-1-hydroxy-12-[2'-(4''-β-amino-3''-methoxycyclohexyl)-1'-methylvinyl]-23,25-dimethoxy-13,19,21,27-tetramethyl-11,28-dioxa-4-azatricyclo[22.3.1.0$^{4,9}$]-octacos-18-ene-2,3,10,16-tetraone (EXAMPLE 3) (50 mg) in methylene chloride (1.2 ml) was added tri(1-methylindol-5-yl)bismuthine (46 mg) followed by copper (II) acetate (12 mg) and the reaction mixture was stirred at rt. After 24 hours, the reaction mixture was diluted with ethyl acetate, washed with saturated sodium bicarbonate and brine and dried over MgSO$_4$, filtered and concentrated in vacuo. The residue was purified by chromatography (silica, ethyl acetate:hexanes, 1:4+1% methanol) to give the title compound.

Partial $^1$H NMR: d: 7.12 (d, J=9.0 Hz, 1H); 6.93 (d, J=3 Hz, 1H); 6.86 (d, J=2 Hz, 1H); 6.69 (dd, J=9.0 & 2.0 Hz, 1H); 6.27 (d, J=3.0 Hz, 1H); 3.70 (s, 3H).

EXAMPLE 40

T-Cell Proliferation Assay

1. Sample Preparation

The compounds to be assayed were dissolved in absolute ethanol at 1 mg/ml.

2. Assay

Spleens from C57B1/6 mice were taken under sterile conditions and gently dissociated in ice-cold RPMI 1640 culture medium (GIBC), Grand Island, N.Y.) supplemented with 10% heat-inactivated fetal calf serum (GIBO)). Cells were pelleted by centrifugation at 1500 rpm for 8 minutes. Contaminating red cells were removed by treating the pellet with ammonium chloride lysing buffer (GIBO)) for 2 minutes at 4° C. Cold medium was added and cells were again centrifuged at 1500 rpm for 8 minutes. T lymphocytes were then isolated by separation of the cell suspension on nylon wool columns as follows: Nylon wool columns were prepared by packing approximately 4 grams of washed and dried nylon wool into 20 ml plastic syringes. The columns were sterilized by autoclaving at 25° F. for 30 minutes. Nylon wool columns were wetted with warm (37° C.) culture medium and rinsed with the same medium. Washed spleen cells resuspended in warm medium were slowly applied to the nylon wool. The columns were then incubated in an upright position at 37° C. for 1 hour. Non-adherent T lymphocytes were eluted from the columns with warm culture medium and the cell suspensions were spun as above.

Purified T lymphocytes were resuspended at $2.5 \times 10^5$ cells/ml in complete culture medium composed of RPMI 1640 medium with 10% heat-inactivated fetal calf serum, 100 mM glutamine, 1 mM sodium pyruvate, $2 \times 10^{-5}$M 2-mercaptoethanol and 50 μg/ml gentamycin. Ionomycin was added at 250 ng/ml and PMA at 10 ng/ml. The cell suspension was immediately distributed into 96 well flat-bottom microculture plates (Costar) at 200 μl/well. The various dilutions of the compound to be tested were then added in triplicate wells at 20 ul/well. The compound 17-allyl-1,14-dihydroxy-12-[2'-(4''-hydroxy-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone was used as a standard. The culture plates were then incubated at 37° C. in a humidified atmosphere of 5% $CO_2$-95% air for 44 hours. The proliferation of T lymphocytes was assessed by measurement of tritiated thymidine incorporation. After 44 hours of culturing, the cells were pulse-labelled with 2 μCi/well of tritiated thymidine (NEN, Cambridge, Mass.). After another 4 hours of incubation, cultures were harvested on glass fiber filters using a multiple sample harvester. Radioactivity of filter discs corresponding to individual wells was measured by standard liquid scintillation counting methods (Betacounter). Mean counts per minute of replicate wells were calculated and the results expressed as concentration of compound required to inhibit tritiated thymidine uptake of T-cells by 50%.

A selection of compounds were tested according to the previous procedure. The title compounds of the following Examples had activity in inhibiting the proliferation of T-cells in the aforementioned assay:

28, 29, 30, 31, 32, 33, 34, 35, 36, 37, 38, and 39.

The results of this assay are representative of the intrinsic immunosuppressive activity of the compounds of the present invention.

For determining antagonist activity, the foregoing procedure is modified in that dilutions of compounds are cultured with 17-ally-1,14-dihydroxy12-[2'-(4''-hydroxy-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone (as a standard) at a concentration of 1.2 nM, a concentration which inhibits T cell proliferation by 100%, the concentration of compound required to reverse the inhibition obtained by the standard alone by 50% is measured, and the $ED_{50}$ value is determined.

While the foregoing specification teaches the principles of the present invention, with examples provided for the purpose of illustration, it will be understood that the practice of the invention encompasses all of the casual variations, adaptations, modifications, deletions, or additions of procedures and protocols described herein, as come within the scope of the following claims and its equivalents.

What is claimed is:

1. A compound of Formula I:

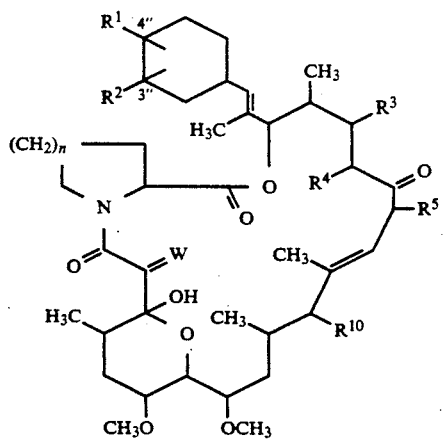

or a pharmaceutically acceptable salt thereof, wherein:

$R^1$ is selected from:
(1) —$NR^6R^7$,
(2) —$NR^6COR^7$,
(3) —$NR^7CO_2R^6$,
(4) —$NR^7CO_2R^6$,
(5) —$NR^6CO_2R^7$, and
(6) —$NR^6CHR^6R^7$;

$R^6$ is selected from
(1) heteroaryl, wherein heteroaryl is selected from the group consisting of:

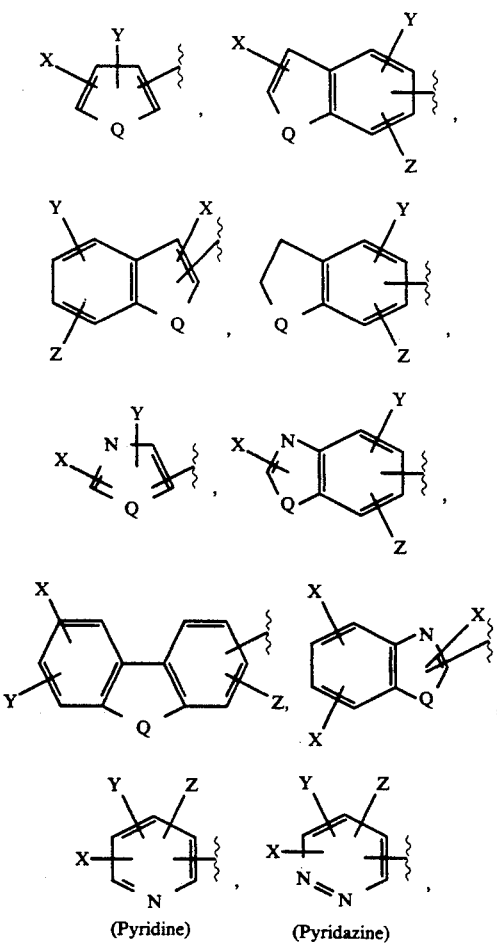

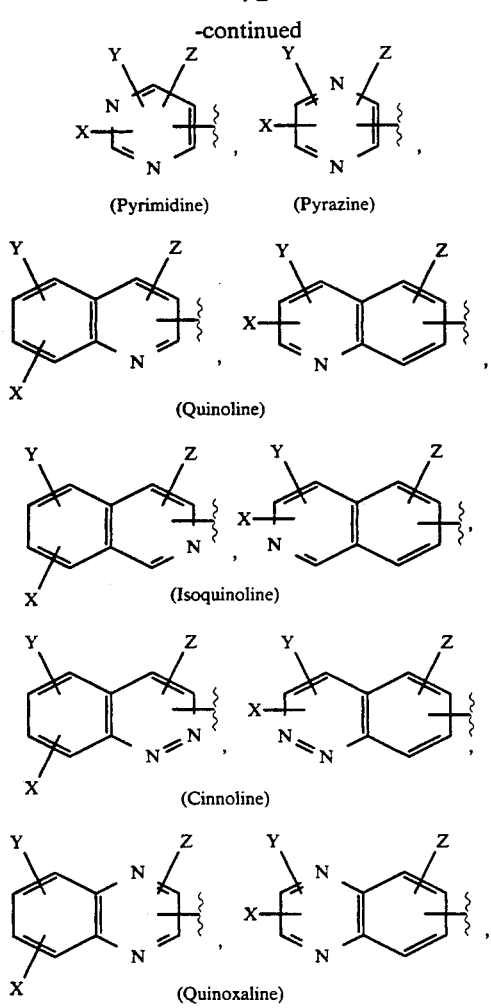

(Pyrimidine)    (Pyrazine)

(Quinoline)

(Isoquinoline)

(Cinnoline)

(Quinoxaline)

wherein Q is N(R$^8$)—, —O—, or —S—;

(2) substituted heteroaryl, wherein heteroaryl is as defined above, and in which the substituents are X, Y and Z;

(3) heteroaryl-C$_{1-10}$alkyl, wherein heteroaryl is as defined above;

(4) substituted heteroaryl-C$_{1-10}$alkyl, wherein heteroaryl is as defined above and in which the heteroaryl group is substituted by X, Y and Z and the alkyl portion may be substituted with one or more of the substituent(s) selected from:
(a) hydroxy,
(b) oxo,
(c) C$_{1-6}$alkoxy,
(d) phenyl-C$_{1-3}$alkoxy,
(e) substituted phenyl-C$_{1-3}$alkoxy, in which the substituents on phenyl are X, Y and Z,
(f) —OCO—C$_{1-6}$alkyl,
(g) —NR$^8$R$^9$, wherein R$^8$ and R$^9$ are independently selected from
 (i) hydrogen,
 (ii) C$_{1-10}$alkyl unsubstituted or substituted with one or more of the substituent(s) selected from:
  (a') phenyl, which is unsubstituted or substituted with X, Y and Z,
  (b') —OH,
  (c') C$_{1-6}$alkoxy,
  (d') —CO$_2$H,
  (e') —CO$_2$—C$_{1-6}$alkyl,
  (f') —C$_{3-7}$cycloalkyl, and
  (g') —OR$^{11}$,
 (iii) C$_{3-10}$alkenyl unsubstituted or substituted with one or more of the substituent(s) selected from:
  (a') phenyl, which is unsubstituted or substituted with X, Y and Z,
  (b') —OH,
  (c') C$_{1-6}$alkoxy,
  (d') —CO$_2$H,
  (e') —CO$_2$—C$_{1-6}$alkyl,
  (f') —C$_{3-7}$cycloalkyl, and
  (g') —OR$^{11}$,
 (iv) or where R$^8$ and R$^9$ and the N to which they are attached may form a heterocyclic ring selected from the group consisting of: morpholine, thiomorpholine, piperidine, and piperizine,
(h) —NR$^8$CO—C$_{1-6}$alkyl-R$^9$, wherein R$^9$ is as defined above,
(i) —NR$^8$CO$_2$—C$_{1-6}$alkyl-R$^9$,
(j) —NR$^8$CONR$^8$R$^9$,
(k) —OCONR$^8$R$^9$,
(l) —COOR$^8$,
(m) —CHO,
(n) phenyl,
(o) substituted phenyl in which the substituents are X, Y and Z,
(p) —S(O)$_p$—C$_{1-6}$alkyl, and
(q) —OR$^{11}$;

(5) heteroaryl-C$_{1-10}$alkyl wherein heteroaryl is as defined above and one or more of the alkyl carbons is replaced by a group selected from: —NR$^8$—, —O—, —S(O)$_p$—, —CO$_2$—, —O$_2$C—, —CONR$^8$—, —NR$^8$CO—, —NR$^8$CONR$^9$—;

(6) substituted heteroaryl-C$_{1-10}$alkyl wherein heteroaryl is as defined above and one or more of the alkyl carbons is replaced by a group selected from: —NR$^8$—, —O—, —S(O)$_p$—, —CO$_2$—, —O$_2$C—, —CONR$^8$—, —NR$^8$CO—, and —NR$^8$CONR$^9$—, the heteroaryl group is substituted with X, Y, and Z, and the alkyl group may be substituted with one or more of the substituent(s) selected from:
(a) hydroxy,
(b) oxo,
(c) C$_{1-6}$alkoxy,
(d) phenyl-C$_{1-3}$alkoxy,
(e) substituted phenyl-C$_{1-3}$alkoxy, in which the substituents on phenyl are X, Y and Z,
(f) —OCO—C$_{1-6}$alkyl,
(g) —NR$^8$R$^9$, wherein R$^8$ and R$^9$ are as defined above,
(h) —NR$^8$CO—C$_{1-6}$alkyl, wherein R$^8$ is as defined above,
(i) —NR$^8$CO$_2$—C$_{1-6}$alkyl,
(j) —NR$^8$CONR$^8$R$^9$,
(k) —OCONR$^8$R$^9$,
(l) —COOR$^8$,
(m) —CHO,
(n) phenyl,
(o) substituted phenyl in which the substituents are X, Y and Z,
(p) —S(O)$_p$—C$_{1-6}$alkyl, and
(q) —OR$^{11}$;

(7) heteroaryl-$C_{3-10}$alkenyl wherein heteroaryl is as defined above and alkenyl contains one to four double bonds;

(8) heteroaryl-$C_{3-10}$alkenyl wherein heteroaryl is as defined above and alkenyl contains one to four double bonds and wherein one or more of the alkyl carbons is replaced by a group selected from: $-NR^8-$, $-O-$, $-S(O)_p-$, $-CO_2-$, $-O_2C-$, $-CONR^8-$, $-NR^8CO-$, and $-NR^8CONR^9-$;

(9) substituted heteroaryl-$C_{3-10}$alkenyl wherein heteroaryl is as defined above and alkenyl contains one to four double bonds and wherein one or more of the alkyl carbons may be replaced by a group selected from: $-NR^8-$, $-O-$, $-S(O)_p-$, $-CO_2-$, $-O_2C-$, $-CONR^8-$, $-NR^8CO-$, $-NR^8CONR^9$, $-NR^8CONR^9$, the heteroaryl group is substituted with X, Y, and Z, and the alkyl group may be substituted with one or more of the substituent(s) selected from:
(a) hydroxy,
(b) oxo,
(c) $C_{1-6}$alkoxy,
(d) phenyl-$C_{1-3}$alkoxy,
(e) substituted phenyl-$C_{1-3}$alkoxy, in which the substituents on phenyl are X, Y and Z,
(f) $-OCO-C_{1-6}$alkyl,
(g) $-NR^8R^9$, wherein $R^8$ and $R^9$ as defined above,
(h) $-NR^8CO-C_{1-6}$alkyl, wherein $R^8$ is as defined above,
(i) $-NR^8CO_2-C_{1-6}$alkyl,
(j) $-NR^8CONR^9$,
(k) $-OCONR^8R^9$,
(l) $-COOR^8$,
(m) $-CHO$,
(n) phenyl,
(o) substituted phenyl in which the substituents are X, Y and Z,
(p) $-S(O)_p-C_{1-6}$alkyl, and
(q) $-OR^{11}$;

$R^2$ is independently selected from:
(1) the definitions of $R^1$;
(2) hydroxy;
(3) phenyloxy;
(4) substituted phenyloxy in which the substituents are X, Y and Z;
(5) 1- or 2-naphthyloxy;
(6) substituted 1- or 2-naphthyloxy in which the substituents are X, Y and Z;
(7) biphenyloxy;
(8) substituted biphenyloxy in which the substituents are X, Y and Z;
(9) $C_{1-10}$alkoxy;
(10) substituted-$C_{1-10}$alkoxy in which one or more substituent(s) is(are) selected from:
(a) hydroxy,
(b) oxo,
(c) $C_{1-6}$alkoxy,
(d) phenyl-$C_{1-3}$alkoxy,
(e) substituted phenyl-$C_{1-3}$alkoxy, in which the substituents on phenyl are X, Y and Z,
(f) $-OCO-C_{1-6}$alkyl,
(g) $-NR^8R^9$, wherein $R^8$ and $R^9$ are as defined above
(h) $-NR^6CO-C_{1-6}$alkyl, wherein $R^6$ is as defined above,
(i) $-COOR^6$, wherein $R^6$ is as defined above,
(j) $-CHO$,
(k) phenyl,
(l) substituted phenyl in which the substituents are X, Y and Z,
(m) 1- or 2-naphthyl,
(n) substituted 1- or 2-naphthyl in which the substituents are X, Y and Z,
(o) biphenyl,
(p) substituted biphenyl in which the substituents are X, Y and Z,
(q) $-OR^{11}$, and
(r) $-S(O)_p-C_{1-6}$alkyl;
(11) $C_{3-10}$alkenyloxy;
(12) substituted $C_{3-10}$alkenyloxy in which one or more substituent(s) is(are) selected from:
(a) hydroxy,
(b) oxo,
(c) $C_{1-6}$alkoxy,
(d) phenyl-$C_{1-3}$alkoxy,
(e) substituted phenyl-$C_{1-3}$alkoxy, in which the substituents on phenyl are X, Y and Z,
(f) $-OCO-C_{1-6}$alkyl,
(g) $-NR^8R^9$, wherein $R^8$ and $R^9$ are as defined above
(h) $-NR^8CO-C_{1-6}$alkyl, wherein $R^8$ is as defined above,
(i) $-COOR^8$, wherein $R^8$ is as defined above,
(j) $-CHO$,
(k) phenyl,
(l) substituted phenyl in which the substituents are X, Y and Z,
(m) 1- or 2-naphthyl,
(n) substituted 1- or 2-naphthyl in which the substituents are X, Y and Z,
(o) biphenyl,
(p) substituted biphenyl in which the substituents are X, Y and Z,
(q) $-OR^{11}$, and
(r) $-S(O)_p-C_{1-6}$alkyl;
(13) $C_{3-10}$alkynyloxy;
(14) substituted $C_{3-10}$alkynyloxy in which one or more substituent(s) is(are) selected from:
(a) hydroxy,
(b) oxo,
(c) $C_{1-6}$alkoxy,
(d) phenyl-$C_{1-3}$alkoxy,
(e) substituted phenyl-$C_{1-3}$alkoxy, in which the substituents on phenyl are X, Y and Z,
(f) $-OCO-C_{1-6}$alkyl,
(g) $-NR^8R^9$, wherein $R^8$ and $R^9$ are as defined above,
(h) $-NR^8CO-C_{1-6}$alkyl, wherein $R^8$ is as defined above,
(i) $-COOR^8$, wherein $R^8$ is as defined above,
(j) $-CHO$,
(k) phenyl,
(l) substituted phenyl in which the substitutents are X, Y and Z,
(m) 1- or 2-naphthyl,
(n) substituted 1- or 2-naphthyl in which the substituents are X, Y and Z,
(o) biphenyl,
(p) substituted biphenyl in which the substituents are X, Y and Z,
(q) $-OR^{11}$; and
(15) $-OR^{11}$;

$R^7$ is selected from
(1) hydrogen, and
(2) $C_{1-10}$alkyl, unsubstituted or substituted with, one or more of the substitutent(s) selected from:

(a) hydroxy,
(b) oxo,
(c) $C_{1-6}$alkoxy,
(d) phenyl-$C_{1-3}$alkoxy,
(e) substituted phenyl-$C_{1-3}$alkoxy, in which the substituents on phenyl are X, Y and Z,
(f) —OCO—$C_{1-6}$alkyl, and
(g) —$NR^8R^9$, wherein $R^8$ and $R^9$ are as defined above;

$R^3$ is hydrogen, hydroxy, —$OR^{11}$, or $C_{1-6}$alkoxy;
$R^4$ is hydrogen, or $R^3$ and $R^4$ taken together form a double bond;
$R^5$ is
 1) methyl,
 2) ethyl,
 3) propyl, or
 4) allyl;
$R^{10}$ is hydrogen, hydroxy, —$OR^{11}$ or fluoro;
$R^{11}$ is selected from:
 (a) —PO(OH)O$^-$M$^+$, wherein M$^+$ is a positively charged inorganic or organic counterion selected from the group consisting of: ammonium, sodium, lithium, potassium, calcium, magnesium, dicyclohexylamine, N-methyl-D-glucamine, arginine and lysine,
 (b) —SO$_3^-$M$^+$,
 (c) —CO(CH$_2$)$_q$CO$_2^-$M$^+$, wherein q is 1 to 3, and
 (d) —CO—$C_{1-6}$alkyl-$NR^8R^9$, wherein $R^8$ and $R^9$ are as defined above and the alkyl is unsubstituted or substituted with one or more substituents selected from:
  (i) hydroxy,
  (ii) $C_{1-6}$alkoxy,
  (iii) —$NR^{16}R^{17}$, wherein $R^{16}$ and $R^{17}$ are independently selected from:
   (a') hydrogen, and
   (b') $C_{1-6}$alkyl,
  (iv) —COO$R^6$, wherein $R^6$ is as defined above,
  (v) phenyl,
  (iv) substituted phenyl in which the substituents are X, Y and Z,
  (vii) heteroaryl,
  (viii) —SH, and
  (ix) —S—$C_{1-6}$alkyl;
W is O or (H,OH);
X, Y and Z independently are selected from:
 (1) hydrogen,
 (2) $C_{1-7}$alkyl,
 (3) $C_{2-6}$alkenyl,
 (4) halogen,
 (5) —(CH$_2$)$_m$—$NR^8R^9$, wherein $R^8$ and $R^9$ are as defined above, and m is 0, 1 or 2,
 (6) —CN,
 (7) —CHO,
 (8) —CF$_3$,
 (9) —$SR^{12}$, wherein $R^{12}$ is hydrogen, $C_{1-6}$alkyl, trifluoromethyl, or phenyl,
 (10) —$SOR^{12}$, wherein $R^{12}$ is as defined above,
 (11) —$SO_2R^{12}$, wherein $R^{12}$ is as defined above,
 (12) —CON$R^8R^9$, wherein $R^8$ and $R^9$ are as defined above,
 (13) $R^{13}$O(CH$_2$)$_m$— wherein $R^{13}$ is hydrogen, $C_{1-3}$alkyl, hydroxy-$C_{2-3}$alkyl, phenyl, $R^{11}$ or naphthyl and m is as defined above,
 (14) —CH(O$R^{14}$)(O$R^{15}$), wherein $R^{14}$ and $R^{15}$ are $C_{1-3}$alkyl or taken together form an ethyl or propyl bridge,

(15) $R^{13}CO(CH_2)_m$— wherein $R^{13}$ and m are as defined above,

(16) $R^{13}OC(CH_2)_m$— wherein $R^{13}$ and m are as defined above, and
 (17) —$OR^{11}$;
or any two of X, Y and Z may be joined to form a saturated ring dioxolanyl or dioxanyl; and
n is 1 or 2.

2. The compound according to claim 1 wherein the absolute configuration of Formula I is as defined in Formula III:

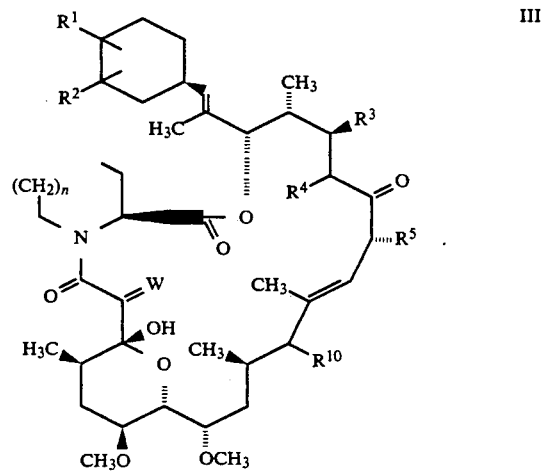

3. The compound according to claim 1 wherein heteroaryl is selected from the group consisting of:

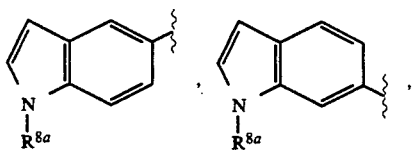

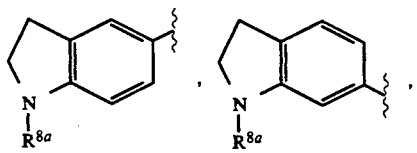

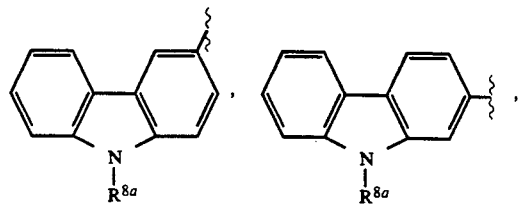

-continued

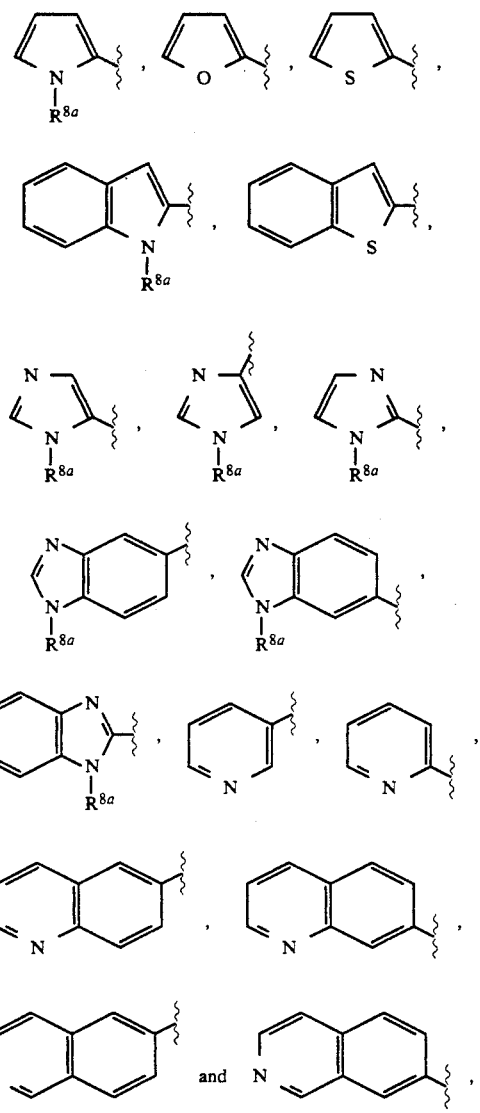

wherein R$^{8a}$ is selected from:
(a) hydrogen;
(b) C$_{1-10}$alkyl, unsubstituted or substituted with one or more substitutents selected from:
  (i) phenyl,
  (ii) substituted phenyl in which the substituents are X, Y and Z,
  (iii) hydroxy,
  (iv) C$_{1-6}$alkoxy,
  (v) —COOR$^{16}$,
  (v) —NR$^{16}$R$^{17}$, and
  (vi) —OR$^{11}$;
(c) C$_{3-10}$alkenyl, unsubstituted or substituted with one or more substitutents selected from:
  (i) phenyl,
  (ii) substituted phenyl in which the substituents are X, Y and Z,
  (iii) hydroxy,
  (iv) C$_{1-6}$alkoxy,
  (v) —COOR$^{16}$,
  (v) —NR$^{16}$R$^{17}$, and
  (vi) —OR$^{11}$.

4. The compound of claim 3 wherein:

R$^2$ is selected from:
  (1) hydroxy,
  (2) methoxy,
  (3) ethoxy,
  (4) propoxy,
  (5) allyloxy,
  (6) —OR$^{11}$,
  (7) —O—C$_{23}$alkyl-OH; and
  (8) —O—C$_{2-3}$alkyl-OR$^{11}$;
R$^3$ is selected from:
  (1) hydrogen,
  (2) hydroxy,
  (3) —OR$^{11}$, or
  R$^3$ and R$^4$ taken together form a double bond;
R$^{10}$ is hydrogen, hydroxy or fluoro;
W is O; and
n is 2.

5. The compound of claim 1 wherein heteroaryl is:

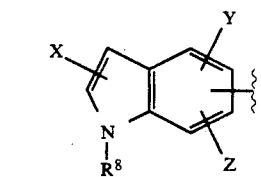

or

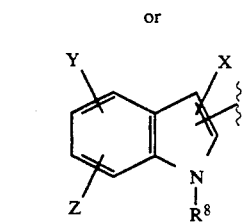

wherein R$^8$, X, Y and Z are as defined above.

6. The compound of claim 1 wherein heteroaryl is:

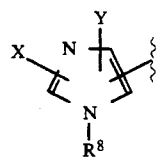

or

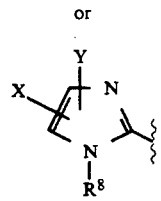

wherein R$^8$, X and Y are as defined above.

7. A compound which is selected from:
17-Ethyl-1-hydroxy-12-[2'-(4"-β-(2-furanyl)methylamino-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-Ethyl-1,14-dihydroxy-12-[2'-(4"-(2-furanyl)methylamino-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-Ethyl-1-hydroxy-12-[2'-(4"-(2-thiophene)methy
lamino-3"-methoxycyclohexyl)-1'-methylvinyl]-
23,25-dimethoxy-13,19,21,27-tetramethyl-11,28-diox-
a-4-azatricyclo[22.3.1.0⁴,⁹]octacos-18-ene-2,3,10,16-
tetraone;

17-Ethyl-1,14-dihydroxy-12-[2'-(4"-(2-thiophene)methy
lamino-3"-methoxycyclohexyl)-1'-methylvinyl]-
23,25-dimethoxy-13,19,21,27-tetramethyl-11,28-diox-
a-4-azatricyclo]22.3.1.0⁴,⁹]octacos-18-ene-2,3,10,16-
tetraone;

17-Ethyl-1,14-dihydroxy-12-[2'-(4"-(2-thiophene)methy
lamino-3"-hydroxycyclohexyl)-1'-methylvinyl]-
23,25-dimethoxy-13,19,21,27-tetramethyl-11,28-diox-
a-4-azatricyclo[22.3.1.0⁴,⁹]octacos-18-ene-2,3,10,16-
tetraone;

17-Ethyl-1,14-dihydroxy-12-[2'-(4"-(2-thiophene
)amino-3"-methoxycyclohexyl)-1'-methylvinyl]-
23,25-dimethoxy-13,19,21,27-tetramethyl-11,28-diox-
a-4-azatricyclo[22.3.1.0⁴,⁹]octacos-18-ene-2,3,10,16-
tetraone;

17-Ethyl-1-hydroxy-12-[2'-(4"-β-(pyrid-2-yl)methylami
no-3"-methoxycyclohexyl)-1'-methylvinyl]-23,25-
dimethoxy-13,19,21,27-tetramethyl-11,28-dioxa-4-
azatricyclo[22.3.1.0⁴,⁹]octacos-18-ene-2,3,10,16-tetr-
aone;

17-Ethyl-1-hydroxy-12-[2'-(4"-β-(pyrid-4-yl)methylami
no-3"-methoxycyclohexyl)-1'-methylvinyl]-23,25-
dimethoxy-13,19,21,27-tetramethyl-11,28-dioxa-4-
azatricyclo[22.3.1.0⁴,⁹]octacos-18-ene-2,3,10,16-tetr-
aone;

17-Ethyl-1-hydroxy-12-[2'-(4"-β-(1-methyl-pyrid-2
-yl)amino-3"-methoxycyclohexyl)-1'-methylvinyl]-
23,25-dimethoxy-13,19,21,27-tetramethyl-11,28-diox-
a-4-azatricyclo[22.3.1.0⁴,⁹]octacos-18-ene-2,3,10,16-
tetraone;

17-Ethyl-1-hydroxy-12-[2'-(4"-β-(imidazol-2-
yl)methylamino-3"-methoxycyclohexyl)-1'-methyl-
vinyl]-23,25-dimethoxy-13,19,21,27-tetramethyl-
11,28-dioxa-4-azatricyclo-[22.3.1.0⁴,⁹]octacos-18-ene-
2,3,10,16-tetraone;

17-Ethyl-1-hydroxy-12-[2'-(4"-β-(imidazolin-2
-yl)methylamino-3"-methoxycyclohexyl)-1'-methyl-
vinyl]-23,25-dimethoxy-13,19,21,27-tetramethyl-
11,28-dioxa-4-azatricyclo[22.3.1.0⁴,⁹]octacos-18-ene-
2,3,10,16-tetraone;

17-Ethyl-1-hydroxy-12-[2'-(4"-β-(1-methylindol-5-
-yl)methylamino-3"-methoxycyclohexyl)-1'-methyl-
vinyl]-23,25-dimethoxy-13,19,21,27-tetramethyl-
11,28-dioxa-4-azatricyclo[22.3.1.0⁴,⁹]octacos-18-ene-
2,3,10,16-tetraone;

17-Ethyl-1-hydroxy-12-[2'-(4"-α-(1-methylindol-5-
-yl)methylamino-3"-methoxycyclohexyl)-1'-methyl-
vinyl]-23,25-dimethoxy-13,19,21,27-tetramethyl-
11,28-dioxa-4-azatricyclo[22.3.1.0⁴,⁹]octacos-18-ene-
2,3,10,16-tetraone;

17-Ethyl-1-hydroxy-12-[2'-(4"-β-(indol-3-yl)methylami
no-3"-methoxycyclohexyl)-1'-methylvinyl]-23,25-
dimethoxy-13,19,21,27-tetramethyl-11,28-dioxa-4-
azatricyclo[22.3.1.0⁴,⁹]octacos-18-ene-2,3,10,16-tetr-
aone;

17-Ethyl-1-hydroxy-12-[2'-(4"-β-(pyrrol-2
-yl)methylamino-3"-methoxycyclohexyl)-1'-methyl-
vinyl]-23,25-dimethoxy-13,19,21,27-tetramethyl-
11,28-dioxa-4-azatricyclo[22.3.1.0⁴,⁹]octacos-18-ene-
2,3,10,16-tetraone;

17-Ethyl-1,14-dihydroxy-12-[2'-(4"-(2-benzothienyl
)amimo-3"-methoxycyclohexyl)-1'-methylvinyl]-
23,25-dimethoxy-13,19,21,27-tetramethyl-11,28-diox-
a-4-azatricyclo[22.3.1.0⁴,⁹]octacos-18-ene-2,3,10,16-
tetraone;

17-Ethyl-1-hydroxy-12-[2'-(4"-β-(1-methyl-5-indo
lyl)amino-3"-methoxycyclohexyl)-1'-methylvinyl]-
23,25-dimethoxy-13,19,21,27-tetramethyl-11,28-diox-
a-4-azatricyclo[22.3.1.0⁴,⁹]octacos-18-ene-2,3,10,16-
tetraone;

17-Ethyl-1-hydroxy-12-[2'-(4"-α-(1-methyl-5-indo
lyl)amino-3"-methoxycyclohexyl)-1'-methylvinyl]-
23,25-dimethoxy-13,19,21,27-tetramethyl-11,28-diox-
a-4-azatricyclo[22.3.1.0⁴,⁹]octacos-18-ene-2,3,10,16-
tetraone;

17-Allyl-1,14-dihydroxy-12-[2'-(4"-(5-indolyl
)amino-3"-methoxycyclohexyl)-1'-methylvinyl]-
23,25-dimethoxy-13,19,21,27-tetramethyl-11,28-diox-
a-4-azatricyclo[22.3.1.0⁴,⁹]octacos-18-ene-2,3,10,16-
tetraone;

17-Ethyl-1,14-dihydroxy-12-[2'-(4"-(5-indoly
l)amino-3"-ethoxycyclohexyl)-1'-methylvinyl]-23,25-
dimethoxy-13,19,21,27-tetramethyl-11,28-dioxa-4-
azatricyclo[22.3.1.0⁴,⁹]octacos-18-ene-2,3,10,16-tetr-
aone;

17-Allyl-1,14-dihydroxy-12-[2'-(4"-(5-indoly
l)amino-3"-ethoxycyclohexyl)-1'-methylvinyl]-23,25-
dimethoxy-13,19,21,27-tetramethyl-11,28-dioxa-4-
azatricyclo[22.3.1.0⁴,⁹]octacos-18-ene-2,3,10,16-tetr-
aone;

17-Allyl-1-hydroxy-12-[2'-(4"-(5-indolyl
)amino-3"-methoxycyclohexyl)-1'-methylvinyl]-
23,25-dimethoxy-13,19,21,27-tetramethyl-11,28-diox-
a-4-azatricyclo[22.3.1.0⁴,⁹]octacos-18-ene-2,3,10,16-
tetraone;

17-Ethyl-1,14-dihydroxy-12-[2'-(4"-(1-N-methyl-5-
indolyl)amino-3"-methoxycyclohexyl)-1'-methyl-
vinyl]-23,25-dimethoxy-13,19,21,27-tetramethyl-
11,28-dioxa-4-azatricyclo[22.3.1.0⁴,⁹]octacos-18-ene-
2,3,10,16-tetraone;

17-Ethyl-1,14-dihydroxy-12-[2'-(4"-(1-N-methyl-5-
indolyl)amino-3"-hydroxycyclohexyl)-1'-methyl-
vinyl]-23,25-dimethoxy-13,19,21,27-tetramethyl-
11,28-dioxa-4-azatricyclo[22.3.1.0⁴,⁹]octacos-18-ene-
2,3,10,16-tetraone;

17-Ethyl-1,14,20-trihydroxy-12-[2'(4"-(1-N-methyl-5-
indolyl)amino-3"-methoxycyclohexyl)-1'-methyl-
vinyl]-23,25-dimethoxy-13,19,21,27-tetramethyl-
11,28-dioxa-4-azatricyclo[22.3.1.0⁴,⁹]octacos-18-ene-
2,3,10,16-tetraone;

17-Ethyl-1,20-dihydroxy-12-[2'-(4"-(1-N-methyl-5-
indolyl)amino-3"-methoxycyclohexyl)-1'-methyl-
vinyl]-23,25-dimethoxy-13,19,21,27-tetramethyl-
11,28-dioxa-4-azatricyclo[22.3.1.0⁴,⁹]octacos-18-ene-
2,3,10,16-tetraone;

17-Allyl-1,14-dihydroxy-12-[2'-(4"-(1-N-methyl-5-
indolyl)amino-3"-methoxycyclohexyl)-1'-methyl-
vinyl]-23,25-dimethoxy-13,19,21,27-tetramethyl-
11,28-dioxa-4-azatricyclo[22.3.1.0⁴,⁹]octacos-18-ene-
2,3,10,16-tetraone;

17-Ethyl-1-hydroxy-12-[2'-(4"-(1-N-methyl-5-
indolyl)amino-3"-methoxycyclohexyl)-1'-methyl-
vinyl]-23,25-dimethoxy-13,19,21,27-tetramethyl-
11,28-dioxa-4-azatricyclo[22.3.1.0⁴,⁹]octacos-18-ene-
2,3,10,16-tetraone;

17-Ethyl-1,14-dihydroxy-12-[2'-(4"-(1-N-methyl-5
-indolyl)amino-3"-ethoxycyclohexyl)-1'-methyl-
vinyl]-23,25-dimethoxy-13,19,21,27-tetramethyl-
11,28-dioxa-4-azatricyclo[22.3.1.0⁴,⁹]octacos-18-ene-
2,3,10,16-tetraone;

17-Allyl-1,14-dihydroxy-12-[2'-(4''-(1-N-methyl-5-indolyl)amino-3''-ethoxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-Ethyl-1,14-dihydroxy-12-[2'-(4''-(1-N-ethyl-5-indolyl)amino-3''-ethoxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-Allyl-1-hydroxy-12-[2'-(4''-(1-N-methyl-5-indolyl)amino-3''-methoxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-Ethyl-1,14-dihydroxy-12-[2'-(4''-(1-N-methyl-5-indolyl)amino-3''-allyloxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-Ethyl-1-hydroxy-12-[2'-(4''-(1-N-methyl-5-indolyl)amino-3''-allyloxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-Ethyl-1,14-dihydroxy-12-[2'-(4''-(1-N-methyl-5-indolyl)amino-3''-n-propyloxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-Ethyl-1-hydroxy-12-[2'-(4''-(1-N-methyl-5-indolyl)amino-3''-n-propyloxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-Ethyl-1,14-dihydroxy-12-[2'-(4''-(1-N-methyl-5-indolyl)amino-3''-i-propyloxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-Ethyl-1,14-dihydroxy-12-[2'-(4''-(1-N-ethyl-5-indolyl)amino-3''-methoxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-Ethyl-1,14-dihydroxy-12-[2'-(4''-(1-N-ethyl-5-indolyl)amino-3''-hydroxycyclohexyl)-1'-methylvinyl]-23,25-dimethoxy-13,19,21,27-tetramethyl-11,28-dioxa-4-azatricyclo-[22.3.1.0⁴,⁹]octacos-18-ene-2,3,10,16-tetraone;

17-Allyl-1,14-dihydroxy-12-[2'-(4''-(1-N-ethyl-5-indolyl)amino-3''-methoxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-Allyl-1,14-dihydroxy-12-[2'-(4''-(1-N-ethyl-5-indolyl)amino-3''-hydroxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-Ethyl-1-hydroxy-12-[2'-(4''-(1-N-ethyl-5-indolyl)amino-3''-methoxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-Allyl-1-hydroxy-12-[2'-(4''-(1-N-ethyl-5-indolyl)amino-3''-methoxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-Allyl-1,14-dihydroxy-12-[2'-(4''-(1-N-ethyl-5-indolyl)amino-3''-ethoxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-Ethyl-1,14-dihydroxy-12-[2'-(4''-(1-N-propyl-5-indolyl)amino-3''-methoxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-Ethyl-1,14-dihydroxy-12-[2'-(4''-(1-N-propyl-5-indolyl)amino-3''-hydroxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-Allyl-1,14-dihydroxy-12-[2'-(4''-(1-N-propyl-5-indolyl)amino-3''-methoxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-Allyl-1,14-dihydroxy-12-[2'-(4''-(1-N-propyl-5-indolyl)amino-3''-hydroxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-Ethyl-1-hydroxy-12-[2'-(4''-(1-N-propyl-5-indolyl)amino-3''-methoxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-Allyl-1-hydroxy-12-[2'-(4''-(1-N-propyl-5-indolyl)amino-3''-methoxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-Ethyl-1,14-dihydroxy-12-[2'-(4''-(1-N-propyl-5-indolyl)amino-3''-ethoxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-Allyl-1,14-dihydroxy-12-[2'-(4''-(1-N-propyl-5-indolyl)amino-3''-ethoxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-Ethyl-1,14-dihydroxy-12-[2'-(4''-(1-N-allyl-5-indolyl)amino-3''-methoxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-Ethyl-1,14-dihydroxy-12-[2'-(4''-(1-N-allyl-5-indolyl)amino-3''-hydroxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-Allyl-1,14-dihydroxy-12-[2'-(4''-(1-N-allyl-5-indolyl)amino-3''-methoxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-Allyl-1,14-dihydroxy-12-[2'-(4''-(1-N-allyl-5-indolyl)amino-3''-hydroxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-Ethyl-1-hydroxy-12-[2'-(4"'-(1-N-allyl-5-indolyl)amino-3"-methoxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-Allyl-1-hydroxy-12-[2'-(4"'-(1-N-allyl-5-indolyl)amino-3"-methoxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-Ethyl-1,14-dihydroxy-12-[2'-(4"'-(1-N-allyl-5-indolyl)amino-3"-ethoxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-Allyl-1,14-dihydroxy-12-[2'-(4"'-(1-N-allyl-5-indolyl)amino-3"-ethoxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-Ethyl-1,14-dihydroxy-12-[2'-(4"'-(1-N-2-hydroxyethyl-5-indolyl)amino-3"-methoxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-Ethyl-1,14-dihydroxy-12-[2'-(4"'-(1-N-2-hydroxyethyl-5-indolyl)amino-3"-hydroxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-Allyl-1,14-dihydroxy-12-[2'-(4"'-(1-N-2-hydroxyethyl-5-indolyl)amino-3"-methoxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-Allyl-1,14-dihydroxy-12-[2'-(4"'-(1-N-hydroxyethyl-5-indolyl)amino-3"-hydroxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-Ethyl-1,14-dihydroxy-12-[2'-(4"'-(1-N-benzyl-5-indolyl)amino-3"-methoxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-Ethyl-1,14-dihydroxy-12-[2'-(4"'-(1-N-benzyl-5-indolyl)amino-3"-hydroxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-Allyl-1,14-dihydroxy-12-[2'-(4"'-(1-N-benzyl-5-indolyl)amino-3"-methoxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-Allyl-1,14-dihydroxy-12-[2'-(4"'-(1-N-benzyl-5-indolyl)amino-3"-hydroxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-Ethyl-1-hydroxy-12-[2'-(4"'-(1-N-benzyl-5-indolyl)amino-3"-methoxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-Allyl-1-hydroxy-12-[2'-(4"'-(1-N-benzyl-5-indolyl)amino-3"-methoxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-Ethyl-1,14-dihydroxy-12-[2'-(4"'-(1-N-benzyl-5-indolyl)amino-3"-ethoxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-Allyl-1,14-dihydroxy-12-[2'-(4"'-(1-N-benzyl-5-indolyl)amino-3"-ethoxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-Ethyl-1,14-dihydroxy-12-[2'-(4"'-(1-N-cyclopropyl-5-indolyl)amino-3"-methoxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-Ethyl-1,14-dihydroxy-12-[2'-(4"'-(1-N-cyclopropyl-5-indolyl)amino-3"-hydroxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-Allyl-1,14-dihydroxy-12-[2'-(4"'-(1-N-cyclopropyl-5-indolyl)amino-3"-methoxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-Allyl-1,14-dihydroxy-12-[2'-(4"'-(1-N-cyclopropyl-5-indolyl)amino-3"-hydroxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-Ethyl-1,14-dihydroxy-12-[2'-(4"'-(1-N-cyclopropyl-5-indolyl)amino-3"-ethoxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-Allyl-1,14-dihydroxy-12-[2'-(4"'-(1-N-cyclopropyl-5-indolyl)amino-3"-ethoxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-Ethyl-1-hydroxy-12-[2'-(4"'-(1-N-cyclopropyl-5-indolyl)amino-3"-methoxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-Allyl-1-hydroxy-12-[2'-(4"'-(1-N-cyclopropyl-5-indolyl)amino-3"-methoxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-Ethyl-1-hydroxy-12-[2'-(4"'-methoxy-N-tryptophanylcarbonylmethylamino-3"-methoxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-Ethyl-1-hydroxy-12-[2'-(4"'-3-indolylethylaminocarbonylmethylamino-3"-methoxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-Ethyl-1,14-dihydroxy-12-[2'-(4"'-(5-indolyl)methylamino-3"-methoxycyclohexyl)-1'-methylvinyl]-23,25-dimethoxy-13,19,21,27-tetramethyl-11,28-dioxa-4-azatricyclo[22.3.1.0^{4,9}]octacos-18-ene-2,3,10,16-tetraone 17-Ethyl-1-hydroxy-12-[2'-(4''-(5-indolyl)methylamino-3''-methoxycyclohexyl)-1'-methylvinyl]-23,25-dimethoxy-13,19,21,27-tetramethyl-11,28-dioxa-4-azatricyclo[22.3.1.0^{4,9}]octacos-18-ene-2,3,10,16-tetraone;

17-Allyl-1,14-dihydroxy-12-[2'-(4''-(5-indolyl)methylamino-3''-methoxycyclohexyl)-1'-methylvinyl]-23,25-dimethoxy-13,19,21,27-tetramethyl-11,28-dioxa-4-azatricyclo[22.3.1.0^{4,9}]octacos-18-ene-2,3,10,16-tetraone;

17-Ethyl-1,14-dihydroxy-12-[2'-(4''-(5-indolyl)methylamino-3''-ethoxycyclohexyl)-1'-methylvinyl]-23,25-dimethoxy-13,19,21,27-tetramethyl-11,28-dioxa-4-azatricyclo[22.3.1.0^{4,9}]octacos-18-ene-2,3,10,16-tetraone;

17-Allyl-1,14-dihydroxy-12-[2'-(4''-(5-indolyl)methylamino-3''-ethoxycyclohexyl)-1'-methylvinyl]-23,25-dimethoxy-13,19,21,27-tetramethyl-11,28-dioxa-4-azatricyclo[22.3.1.0^{4,9}]octacos-18-ene-2,3,10,16-tetraone;

17-Allyl-1-hydroxy-12-[2'-(4''-(5-indolyl)methylamino-3''-methoxycyclohexyl)-1'-methylvinyl]-23,25-dimethoxy-13,19,21,27-tetramethyl-11,28-dioxa-4-azatricyclo[22.3.1.0^{4,9}]octacos-18-ene-2,3,10,16-tetraone;

17-Ethyl-1,14-dihydroxy-12-[2'-(4''-(1-N-methyl-5-indolyl)methylamino-3''-methoxycyclohexyl)-1'-methylvinyl]-23,25-dimethoxy-13,19,21,27-tetramethyl-11,28-dioxa-4-azatricyclo[22.3.1.0^{4,9}]octacos-18-ene-2,3,10,16-tetraone;

17-Ethyl-1,14-dihydroxy-12-[2'-(4''-(1-N-methyl-5-indolyl)methylamino-3''-hydroxycyclohexyl)-1'-methylvinyl]-23,25-dimethoxy-13,19,21,27-tetramethyl-11,28-dioxa-4-azatricyclo[22.3.1.0^{4,9}]octacos-18-ene-2,3,10,16-tetraone;

17-Ethyl-1,14,20-trihydroxy-12-[2'-(4''-(1-N-methyl-5-indolyl)methylamino-3''-methoxycyclohexyl)-1'-methylvinyl]-23,25-dimethoxy-13,19,21,27-tetramethyl-11,28-dioxa-4-azatricyclo[22.3.1.0^{4,9}]octacos-18-ene-2,3,10,16-tetraone;

17-Ethyl-1,20-dihydroxy-12-[2'-(4''-(1-N-methyl-5-indolyl)methylamino-3''-methoxycyclohexyl)-1'-methylvinyl]-23,25-dimethoxy-13,19,21,27-tetramethyl-11,28-dioxa-4-azatricyclo[22.3.1.0^{4,9}]octacos-18-ene-2,3,10,16-tetraone;

17-Allyl-1,14-dihydroxy-12-[2'-(4''-(1-N-methyl-5-indolyl)amino-3''-methoxycyclohexyl)-1'-methylvinyl]-23,25-dimethoxy-13,19,21,27-tetramethyl-11,28-dioxa-4-azatricyclo[22.3.1.0^{4,9}]octacos-18-ene-2,3,10,16-tetraone;

17-Ethyl-1-hydroxy-12-[2'-(4''-(1-N-methyl-5-indolyl)methylamino-3''-methoxycyclohexyl)-1'-methylvinyl]-23,25-dimethoxy-13,19,21,27-tetramethyl-11,28-dioxa-4-azatricyclo[22.3.1.0^{4,9}]octacos-18-ene-2,3,10,16-tetraone;

17-Ethyl-1,14-dihydroxy-12-[2'-(4''-(1-N-methyl-5-indolyl)methylamino-3''-ethoxycyclohexyl)-1'-methylvinyl]-23,25-dimethoxy-13,19,21,27-tetramethyl-11,28-dioxa-4-azatricyclo[22.3.1.0^{4,9}]octacos-18-ene-2,3,10,16-tetraone;

17-Allyl-1,14-dihydroxy-12-[2'-(4''-(1-N-methyl-5-indolyl)amino-3''-ethoxycyclohexyl)-1'-methylvinyl]-23,25-dimethoxy-13,19,21,27-tetramethyl-11,28-dioxa-4-azatricyclo[22.3.1.0^{4,9}]octacos-18-ene-2,3,10,16-tetraone;

17-Ethyl-1,14-dihydroxy-12-[2'-(4''-(1-N-ethyl-5-indolyl)methylamino-3''-ethoxycyclohexyl)-1'-methylvinyl]-23,25-dimethoxy-13,19,21,27-tetramethyl-11,28-dioxa-4-azatricyclo[22.3.1.0^{4,9}]octacos-18-ene-2,3,10,16-tetraone;

17-Allyl-1-hydroxy-12-[2'-(4''-(1-N-methyl-5-indolyl)methylamino-3''-methoxycyclohexyl)-1'-methylvinyl]-23,25-dimethoxy-13,19,21,27-tetramethyl-11,28-dioxa-4-azatricyclo[22.3.1.0^{4,9}]octacos-18-ene-2,3,10,16-tetraone;

17-Ethyl-1,14-dihydroxy-12-[2'-(4''-(1-N-methyl-5-indolyl)methylamino-3''-allyloxycyclohexyl)-1'-methylvinyl]-23,25-dimethoxy-13,19,21,27-tetramethyl-11,28-dioxa-4-azatricyclo[22.3.1.0^{4,9}]octacos-18-ene-2,3,10,16-tetraone;

17-Ethyl-1-hydroxy-12-[2'-(4''-(1-N-methyl-5-indolyl)methylamino-3''-allyloxycyclohexyl)-1'-methylvinyl]-23,25-dimethoxy-13,19,21,27-tetramethyl-11,28-dioxa-4-azatricyclo[22.3.1.0^{4,9}]octacos-18-ene-2,3,10,16-tetraone;

17-Ethyl-1,14-dihydroxy-12-[2'-(4''-(1-N-methyl-5-indolyl)methylamino-3''-n-propyloxycyclohexyl)-1'-methylvinyl]-23,25-dimethoxy-13,19,21,27-tetramethyl-11,28-dioxa-4-azatricyclo[22.3.1.0^{4,9}]octacos-18-ene-2,3,10,16-tetraone;

17-Ethyl-1-hydroxy-12-[2'-(4''-(1-N-methyl-5-indolyl)methylamino-3''-n-propyloxycyclohexyl)-1'-methylvinyl]-23,25-dimethoxy-13,19,21,27-tetramethyl-11,28-dioxa-4-azatricyclo[22.3.1.0^{4,9}]octacos-18-ene-2,3,10,16-tetraone;

17-Ethyl-1,14-dihydroxy-12-[2'-(4''-(1-N-methyl-5-indolyl)methylamino-3''-i-propyloxycyclohexyl)-1'-methylvinyl]-23,25-dimethoxy-13,19,21,27-tetramethyl-11,28-dioxa-4-azatricyclo[22.3.1.0^{4,9}]octacos-18-ene-2,3,10,16-tetraone;

17-Ethyl-1,14-dihydroxy-12-[2'-(4''-(1-N-ethyl-5-indolyl)methylamino-3''-methoxycyclohexyl)-1'-methylvinyl]-23,25-dimethoxy-13,19,21,27-tetramethyl-11,28-dioxa-4-azatricyclo[22.3.1.0^{4,9}]octacos-18-ene-2,3,10,16-tetraone;

17-Ethyl-1,14-dihydroxy-12-[2'-(4''-(1-N-ethyl-5-indolyl)methylamino-3''-hydroxycyclohexyl)-1'-methylvinyl]-23,25-dimethoxy-13,19,21,27-tetramethyl-11,28-dioxa-4-azatricyclo[22.3.1.0^{4,9}]octacos-18-ene-2,3,10,16-tetraone;

17-Allyl-1,14-dihydroxy-12-[2'-(4''-(1-N-ethyl-5-indolyl)methylamino-3''-methoxycyclohexyl)-1'-methylvinyl]-23,25-dimethoxy-13,19,21,27-tetramethyl-11,28-dioxa-4-azatricyclo[22.3.1.0^{4,9}]octacos-18-ene-2,3,10,16-tetraone;

17-Allyl-1,14-dihydroxy-12-[2'-(4''-(1-N-ethyl-5-indolyl)amino-3''-hydroxycyclohexyl)-1'-methylvinyl]-23,25-dimethoxy-13,19,21,27-tetramethyl-11,28-dioxa-4-azatricyclo[22.3.1.0^{4,9}]octacos-18-ene-2,3,10,16-tetraone;

17-Ethyl-1-hydroxy-12-[2'-(4''-(1-N-ethyl-5-indolyl)methylamino-3''-methoxycyclohexyl)-1'-methylvinyl]-23,25-dimethoxy-13,19,21,27-tetramethyl-11,28-dioxa-4-azatricyclo[22.3.1.0^{4,9}]octacos-18-ene-2,3,10,16-tetraone;

17-Allyl-1-hydroxy-12-[2'-(4''-(1-N-ethyl-5-indolyl)methylamino-3''-methoxycyclohexyl)-1'-methylvinyl]-23,25-dimethoxy-13,19,21,27-tetramethyl-11,28-dioxa-4-azatricyclo[22.3.1.0^{4,9}]octacos-18-ene-2,3,10,16-tetraone;

17-Allyl-1,14-dihydroxy-12-[2'-(4''-(1-N-ethyl-5-indolyl)amino-3''-ethoxycyclohexyl)-1'-methylvinyl]-23,25-dimethoxy-13,19,21,27-tetramethyl- 17-Ethyl-1,14-dihydroxy-12-[2'-(4"-(1-N-propyl-5-indol yl)methylamino-3"-methoxycyclohexyl)-1'-methylvinyl]23,25-dimethoxy-13,19,21,27-tetramethyl-11,28-dioxa-4-azatricyclo[22.3.1.0⁴,⁹]octacos-18 -ene-2,3,10,16-tetraone;

17-Ethyl-1,14-dihydroxy-12-[2'-(4"-(1-N-propyl-5-indol yl)methylamino-3"-hydroxycyclohexyl)-1'-methylvinyl]23,25-dimethoxy-13,19,21,27-tetramethyl-11,28-dioxa-4-azatricyclo[22.3.1.0⁴,⁹]octacos-18-ene-2,3,10,16-tetraone;

17-Allyl-1,14-dihydroxy-12-[2'-(4"-(1-N-propyl-5--indolyl)methylamino-3"-methoxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-Allyl-1,14-dihydroxy-12-[2'-(4"-(1-N-propyl-5--indolyl)methylamino-3"-hydroxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-Ethyl-1-hydroxy-12-[2'-(4"-(1-N-propyl-5-indoly l)methylamino-3"-methoxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-Allyl-1-hydroxy-12-[2'-(4"-(1-N-propyl-5-indolyl)methylamino-3"-methoxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-Ethyl-1,14-dihydroxy-12-[2'-(4"-(1-N-propyl-5 -indolyl)amino-3"-ethoxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-Allyl-1,14-dihydroxy-12-[2'-(4"-(1-N-propyl-5-indol yl)methylamino-3"-ethoxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-Ethyl-1,14-dihydroxy-12-[2'-(4"-(1-N-allyl-5-indoly l)methylamino-3"-methoxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-Ethyl-1,14-dihydroxy-12-[2'-(4"-(1-N-allyl-5-indoly l)methylamino-3"-hydroxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-Allyl-1,14-dihydroxy-12-[2'-(4"-(1-N-allyl-5-indoly l)methylamino-3"-methoxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-Allyl-1,14-dihydroxy-12-[2'-(4"-(1-N-allyl-5-indoly l)methylamino-3"-hydroxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-Ethyl-1-hydroxy-12-[2'-(4"-(1-N-allyl-5-indoly l)methylamino-3"-methoxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-Allyl-1-hydroxy-12-[2'-(4"-(1-N-allyl-5-indoly l)methylamino-3"-methoxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-Ethyl-1,14-dihydroxy-12-[2'-(4"-(1-N-allyl-5-indoly l)methylamino-3"-ethoxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-Allyl-1,14-dihydroxy-12-[2'-(4"-(1-N-allyl-5-indol yl)methylamino-3"-ethoxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-Ethyl-1,14-dihydroxy-12-[ 2'-(4"-(1-N-2-hydroxyethyl-5-indoly l)methylamino-3"-methoxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-Ethyl-1,14-dihydroxy-12-[ 2'-(4"-(1-N-2-hydroxyethyl-5-indoly l)methylamino-3"-hydroxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-Allyl-1,14-dihydroxy-12-[ 2'-(4"-(1-N-2-hydroxyethyl-5-indoly l)methylamino-3"-methoxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-Allyl-1,14-dihydroxy-12-[2'-(4"-(1-N-hydroxyethyl-5-indolyl)methylamino-3"-hydroxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-Ethyl-1,14-dihydroxy-12-[2'-(4"-(1-N-benzyl-5--indolyl)methylamino-3"-methoxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-Ethyl-1,14-dihydroxy-12-[2'-(4"-(1-N-benzyl-5--indolyl)methylamino-3"-hydroxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-Allyl-1,14-dihydroxy-12-[2'-(4"-(1-N-benzyl-5--indolyl)methylamino-3"-methoxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-Allyl-1,14-dihydroxy-12-[2'-(4"-(1-N-benzyl-5--indolyl)methylamino-3"-hydroxycyclohexyl)-1'-methylvinyl]-23,25-dimethoxy-13,19,21,27-tetramethyl-11,28-dioxa-4-azatricyclo[22.3.1.0⁴,⁹]octacos-18 -ene-2,3,10,16-tetraone;

17-Ethyl-1-hydroxy-12-[2'-(4"-(1-N-benzyl-5-indoly l)methylamino-3"-methoxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-Allyl-1-hydroxy-12-[2'-(4"-(1-N-benzyl-5-indoly l)methylamino-3"-methoxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-Ethyl-1,14-dihydroxy-12-[2'-(4''-(1-N-benzyl-5-indolyl)methylamino-3''-ethoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-Allyl-1,14-dihydroxy-12-[2'-(4''-(1-N-benzyl-5-indolyl)methylamino-3''-ethoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-Ethyl-1,14-dihydroxy-12-[2'-(4''-(1-N-cyclopropyl-5-indolyl)methylamino-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-Ethyl-1,14-dihydroxy-12-[2'-(4''-(1-N-cyclopropyl-5-indolyl)methylamino-3''-hydroxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-Allyl-1,14-dihydroxy-12-[2'-(4''-(1-N-cyclopropyl-5-indolyl)methylamino-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-Allyl-1,14-dihydroxy-12-[2'-(4''-(1-N-cyclopropyl-5-indolyl)methylamino-3''-hydroxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-Ethyl-1,14-dihydroxy-12-[2'-(4''-(1-N-cyclopropyl-5-indolyl)methylamino-3''-ethoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-Allyl-1,14-dihydroxy-12-[2'-(4''-(1-N-cyclopropyl-5-indolyl)methylamino-3''-ethoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-Ethyl-1-hydroxy-12-[2'-(4''-(1-N-cyclopropyl-5-indolyl)methylamino-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-Allyl-1-hydroxy-12-[2'-(4''-(1-N-cyclopropyl-5-indolyl)methylamino-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

and pharmaceutically acceptable salts thereof.

8. A compound which is:

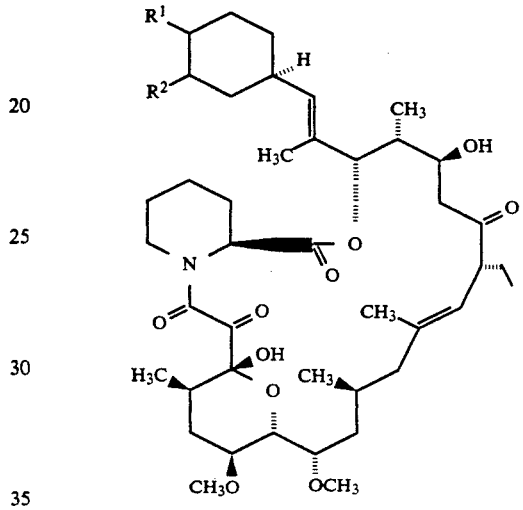

wherein R$^1$ and R$^2$ are selected from the following combinations of substituents:

| | R$^1$ | R$^2$ |
|---|---|---|
| (a) | 1-methyl-1H-indol-5-yl-NH- (CH$_3$ on N) | CH$_3$O |
| (b) | 1-methyl-1H-indol-5-yl-NH- (CH$_3$ on N) | OH |
| (c) | 1-ethyl-1H-indol-5-yl-NH- | CH$_3$O |
| (d) | 1-allyl-1H-indol-5-yl-NH- | CH$_3$O |

-continued
| | R¹ | R² |
|---|---|---|
| (e) |  | CH₃O |
| (f) |  | OH |
| (g) |  | OH |
| (h) |  | OH |
| (i) |  | CH₃O |
| (j) |  | OH |
| (k) |  | CH₃O |

-continued

| | R¹ | R² |
|---|---|---|
| (l) | HOCH₂CH₂-N(indol-1-yl)-5-NH- (1-(2-hydroxyethyl)indol-5-ylamino) | OH |
| (m) | 4-HO-C₆H₄-CH₂-N(indol-1-yl)-5-NH- (1-(4-hydroxybenzyl)indol-5-ylamino) | CH₃O |
| (n) | 4-HO-C₆H₄-CH₂-N(indol-1-yl)-5-NH- (1-(4-hydroxybenzyl)indol-5-ylamino) | OH |
| (o) | OH | 1-methylindol-5-ylamino |
| (p) | OH | 1-ethylindol-5-ylamino |
| (q) | (1H-imidazol-2-yl)methylamino | CH₃O |
| (r) | (4-methyl-1H-imidazol-2-yl)methylamino | CH₃O |
| (s) | (4-phenyl-1H-imidazol-2-yl)methylamino | CH₃O |

-continued

| | R¹ | R² |
|---|---|---|
| (t) | 4-phenyl-1H-imidazol-2-yl-CH₂-NH-⁓ | OH |
| (u) | OH | 4-phenyl-1H-imidazol-2-yl-CH₂-NH-⁓ |
| (v) | 1H-imidazol-2-yl-CH₂-NH-⁓ | OH |
| (w) | 4-methyl-1H-imidazol-2-yl-CH₂-NH-⁓ | OH |
| (x) | 4-phenyl-1-methylimidazol-2-yl-CH₂-NH-⁓ | CH₃O |
| (y) | 4-phenyl-1-methylimidazol-2-yl-CH₂-NH-⁓ | OH |
| (z) | OH | 4-phenyl-1-methylimidazol-2-yl-CH₂-NH-⁓ |
| (aa) | 4-phenyl-5-methyl-1H-imidazol-2-yl-CH₂-NH-⁓ | CH₃O |

-continued

| | R¹ | R² |
|---|---|---|
| (bb) | 4-phenyl-5-(methoxymethyl)-1H-imidazol-2-yl-methylamino- | CH₃O |
| (cc) | 4-phenyl-5-methyl-1H-imidazol-2-yl-methylamino- | OH |
| (dd) | 4-phenyl-5-(methoxymethyl)-1H-imidazol-2-yl-methylamino- | OH |
| (ee) | 4-(4-hydroxyphenyl)-1H-imidazol-2-yl-methylamino- | CH₃O |
| (ff) | 4-(3-hydroxyphenyl)-1H-imidazol-2-yl-methylamino- | CH₃O |
| (gg) | 4-(3,5-difluorophenyl)-1H-imidazol-2-yl-methylamino- | CH₃O |
| (hh) | 4-(4-hydroxyphenyl)-1H-imidazol-2-yl-methylamino- | OH |

-continued

| | R¹ | R² |
|---|---|---|
| (ii) | 3-hydroxyphenyl-imidazol-2-yl-CH₂-NH- | OH |
| (jj) | 3,5-difluorophenyl-imidazol-2-yl-CH₂-NH- | OH |
| (kk) | 4-chlorophenyl-imidazol-2-yl-CH₂-NH- | CH₃O |
| (ll) | 4-chlorophenyl-imidazol-2-yl-CH₂-NH- | OH |
| (mm) | 3,5-dichlorophenyl-imidazol-2-yl-CH₂-NH- | CH₃O |
| (nn) | 3,5-dichlorophenyl-imidazol-2-yl-CH₂-NH- | OH |
| (oo) | 1-benzylimidazol-2-yl-CH₂-NH- | CH₃O |

-continued
| | R¹ | R² |
|---|---|---|
| (pp) | 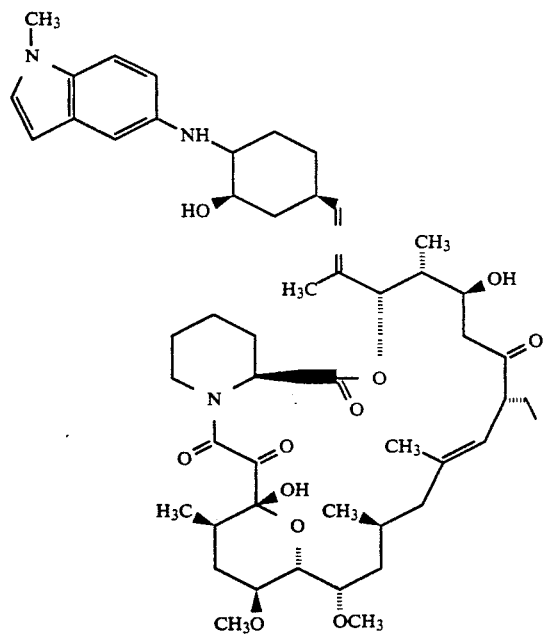 | CH₃O |
| (qq) | | CH₃O |
9. The compound of claim 8 which is:
10. The compound of claim 8 which is:
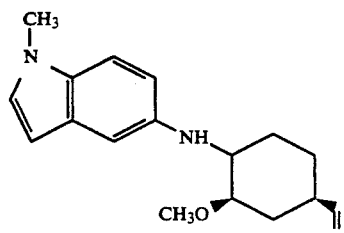
11. The compound of claim 8 which is:
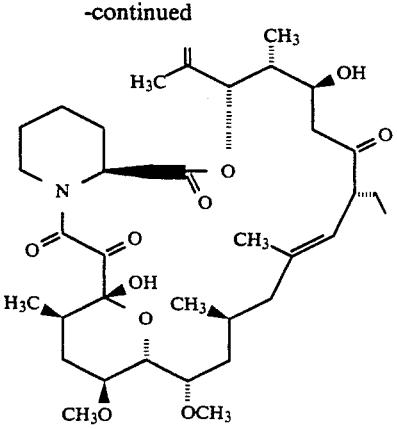
12. The compound of claim 8 which is:
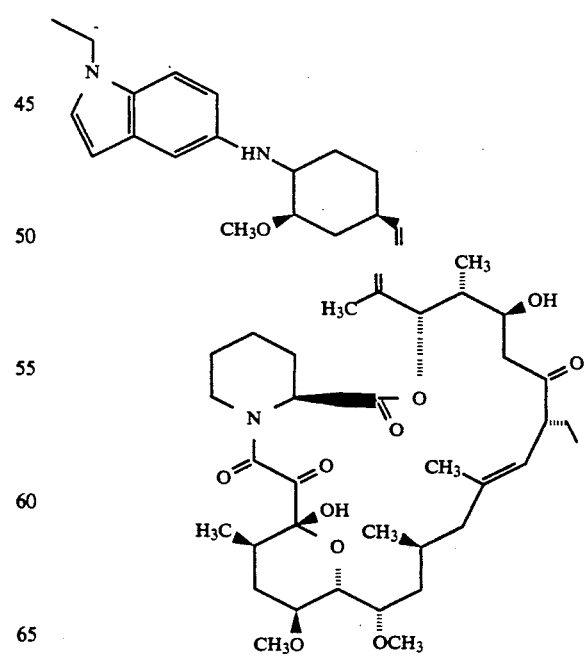

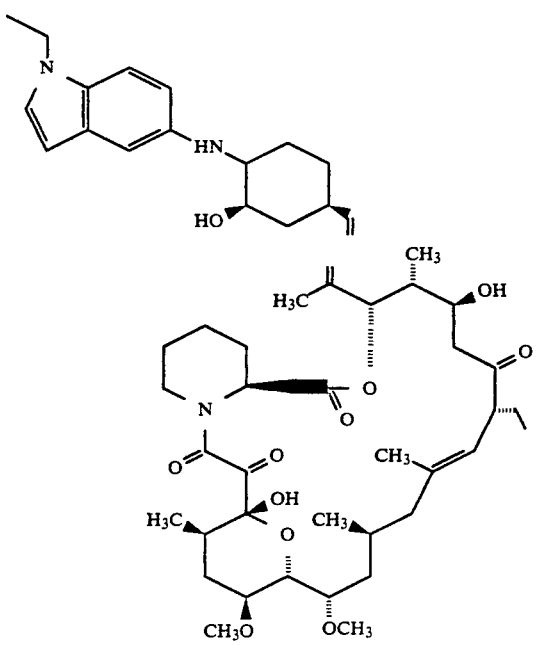
13. The compound of claim 8 which is:
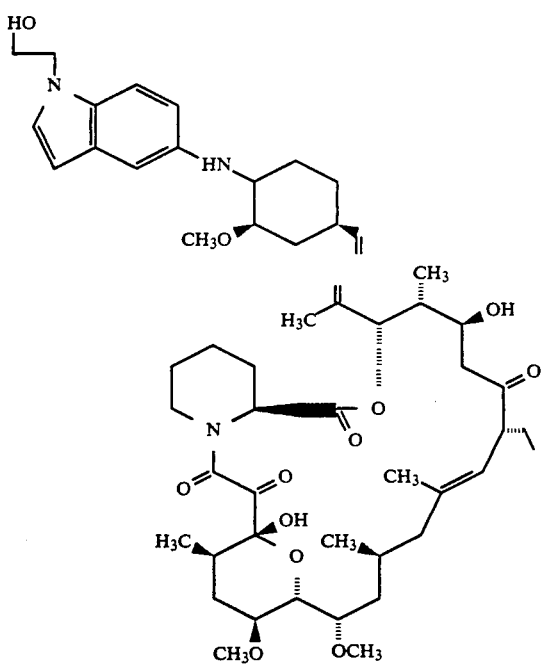
14. The compound of claim 8 which is:
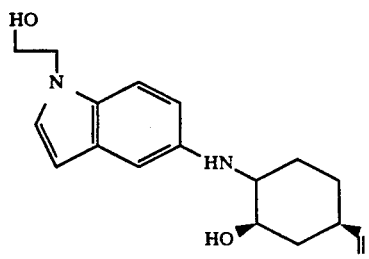
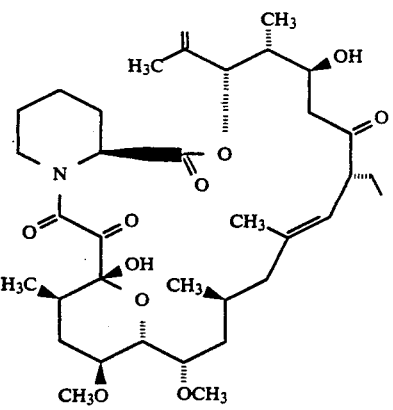
15. The compound of claim 8 which is:
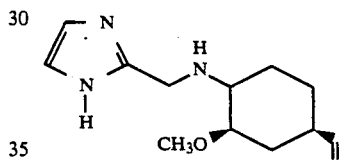
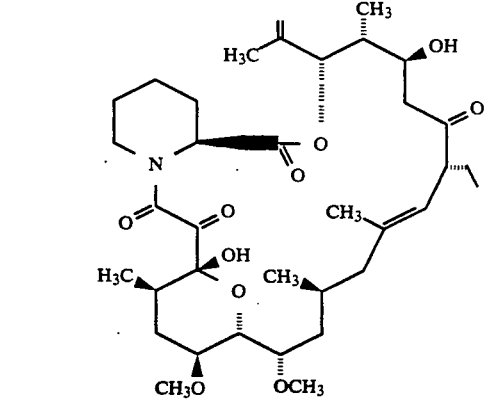
16. The compound of claim 8 which is:
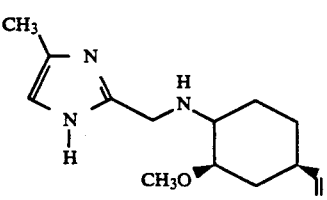

17. The compound of claim 8 which is:
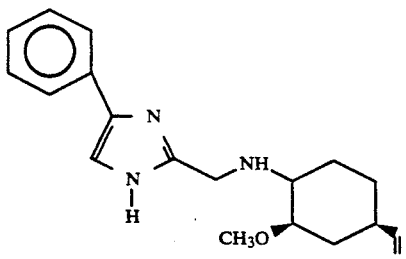
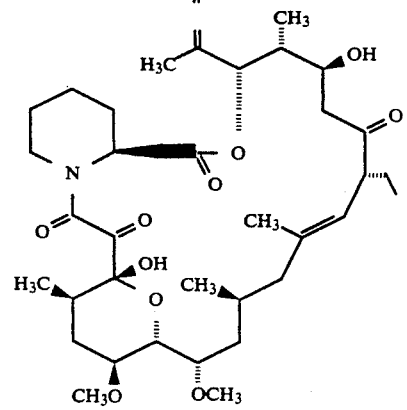
18. The compound of claim 8 which is:
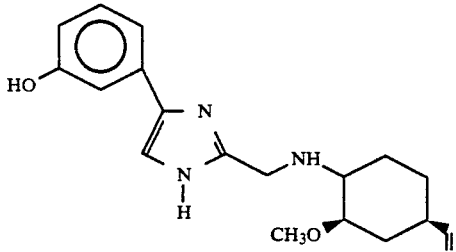
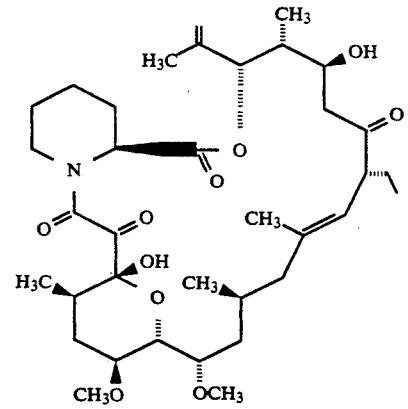
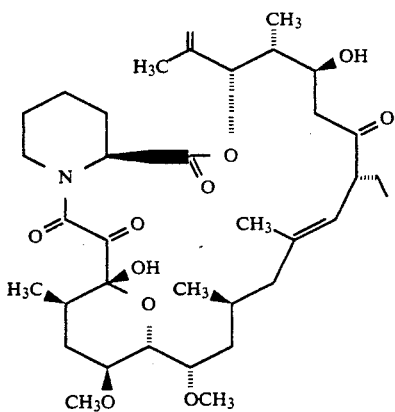
19. The compound of claim 8 which is:

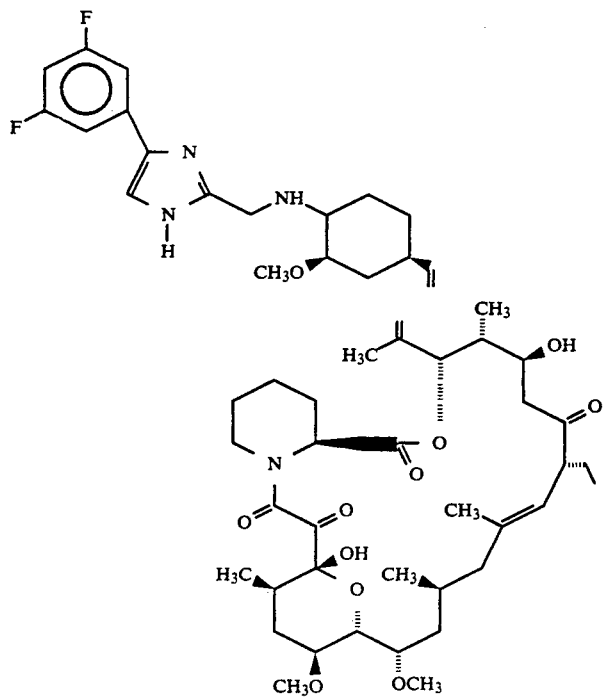
20. The compound of claim 8 which is:
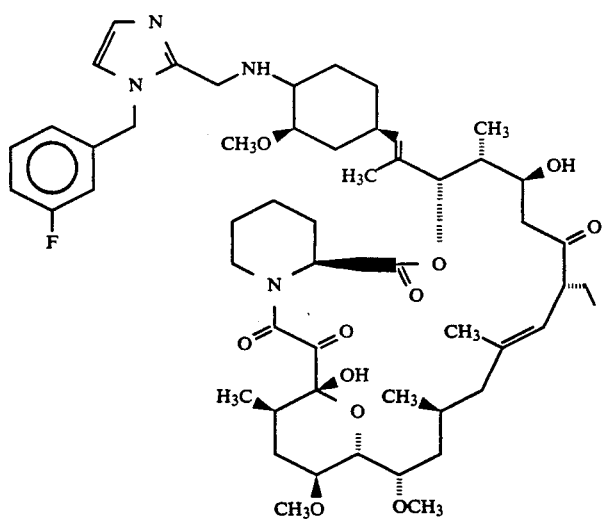
21. The compound of claim 8 which is:

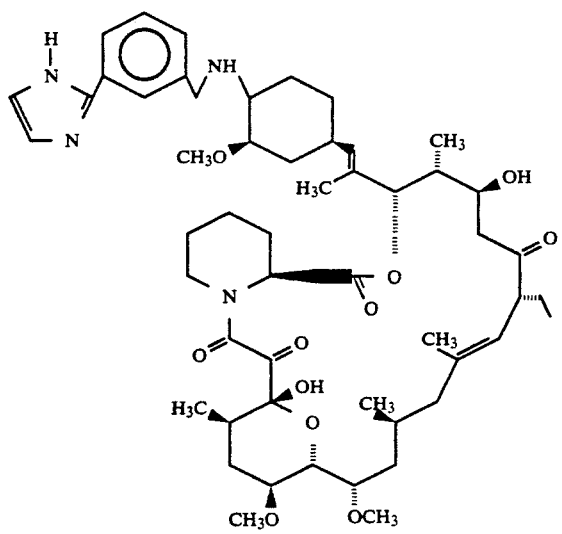

22. A pharmaceutical composition for the treatment of immunoregulatory disorders or diseases comprising a pharmaceutical carrier and a therapeutically effective amount of the compound of claim 1.

23. A pharmaceutical composition for the treatment of resistance to transplantation comprising a pharmaceutical carrier and a therapeutically effective amount of the compound of claim 1.

24. A pharmaceutical composition for the topical treatment of inflammatory and hyperproliferative skin diseases and/or cutaneous manifestations of immunologically-mediated illnesses comprising a pharmaceutical carrier and a therapeutically effective amount of the compound of claim 1.

25. A pharmaceutical composition for the treatment of reversible obstructive airways disease comprising a pharmaceutical carrier and a therapeutically effective amount of the compound of claim 1.

26. A pharmaceutical composition for revitalizing hair comprising a pharmaceutical carrier and a therapeutically effective amount of the compound of claim 1.

27. A method for the treatment of immunoregulatory disorders or diseases comprising the administration to a mammalian species in need of such treatment an effective amount of the compound of claim 1.

28. A method for the treatment of resistance to transplantation comprising the administration to a mammalian species in need of such treatment an effective amount of the compound of claim 1.

29. A method for the topical treatment of inflammatory and hyperproliferative skin diseases and or cutaneous manifestations of immunologically-mediated illnesses comprising the administration to a mammalian species in need of such treatment an effective amount of the compound of claim 1.

30. A method for the treatment of reversible obstructive airways disease comprising the administration to a mammalian species in need of such treatment of an effective amount of the compound claim 1.

31. A method for revitalizing hair comprising h administration to a mammalian species in need of such treatment of an effective amount of the compound of claim 1.

32. A method for the treatment of male pattern alopecia or alopecia senilis comprising the administration to a mammalian species in need of such treatment of an effective amount of the compound claim 1.

* * * * *